US012263298B2

(12) United States Patent
Von Schuckmann

(10) Patent No.: US 12,263,298 B2
(45) Date of Patent: Apr. 1, 2025

(54) DEVICE FOR INHALING POWDER-TYPE SUBSTANCES

(71) Applicant: Alfred Von Schuckmann, Kevelaer (DE)

(72) Inventor: Alfred Von Schuckmann, Kevelaer (DE)

( * ) Notice: Subject to any disclaimer, the term of this patent is extended or adjusted under 35 U.S.C. 154(b) by 932 days.

(21) Appl. No.: 17/422,513

(22) PCT Filed: Jan. 14, 2020

(86) PCT No.: PCT/EP2020/050814
§ 371 (c)(1),
(2) Date: Jul. 13, 2021

(87) PCT Pub. No.: WO2020/148281
PCT Pub. Date: Jul. 23, 2020

(65) Prior Publication Data
US 2022/0096762 A1    Mar. 31, 2022

(30) Foreign Application Priority Data

Jan. 14, 2019  (DE) ................... 10 2019 100 834.4
Jan. 13, 2020  (DE) ................... 10 2020 100 551.2

(51) Int. Cl.
*A61M 15/00*    (2006.01)
(52) U.S. Cl.
CPC ...... *A61M 15/0026* (2014.02); *A61M 15/007* (2014.02); *A61M 2202/064* (2013.01)
(58) Field of Classification Search
CPC .......... A61M 15/0026; A61M 15/0045–0051; A61M 15/0028–0041
See application file for complete search history.

(56) References Cited

U.S. PATENT DOCUMENTS

| 7,571,724 B2 | 8/2009 | Braithwaite |
| 8,511,304 B2 | 8/2013 | Anderson et al. |

(Continued)

FOREIGN PATENT DOCUMENTS

| EP | 0 211 595 A2 | 2/1987 |
| EP | 1 992 376 A1 | 11/2008 |

(Continued)

OTHER PUBLICATIONS

International Search Report of PCT/EP2020/050814, mailed Apr. 21, 2020.

(Continued)

*Primary Examiner* — Joseph D. Boecker
*Assistant Examiner* — Thomas W Greig
(74) *Attorney, Agent, or Firm* — Collard & Roe, P.C.

(57) ABSTRACT

A device for inhaling powder-type substances includes a mouthpiece, an insertion unit having a retaining part with an insertion means for opening a sub-region in a substance container containing the substance, and a discharge channel for the substance leading to the mouthpiece. In order to advantageously further improve a device of this type, it is proposed that two insertion units are provided, having preferably two retaining parts, which are separate from one another, which each have an insertion means, and with which the substance container can be opened in intersecting or opposing insertion directions. The device for inhaling powder-type substances also includes a plurality of substance containers that can be moved successively into an emptying position. The number of emptied or non-emptied substance containers can be displayed via a counter.

20 Claims, 39 Drawing Sheets

(56) References Cited

U.S. PATENT DOCUMENTS

| | | | | |
|---|---|---|---|---|
| 2005/0268909 | A1* | 12/2005 | Bonney | A61M 15/0043 128/203.15 |
| 2006/0254583 | A1* | 11/2006 | Deboeck | A61M 15/0035 128/203.15 |
| 2007/0131225 | A1* | 6/2007 | Rand | A61M 15/0028 128/200.23 |
| 2007/0137645 | A1* | 6/2007 | Eason | A61M 15/0025 128/203.15 |
| 2007/0181123 | A1* | 8/2007 | Houzego | A61M 15/0061 128/203.15 |
| 2008/0105256 | A1* | 5/2008 | Lulla | A61M 15/0028 128/203.21 |
| 2009/0090362 | A1* | 4/2009 | Harmer | A61M 15/0045 128/203.21 |
| 2010/0078021 | A1* | 4/2010 | Thoe | A61P 31/04 128/203.15 |
| 2010/0083962 | A1* | 4/2010 | Von Schuckmann | A61M 15/0048 128/203.15 |
| 2010/0258118 | A1* | 10/2010 | Morton | A61M 15/0078 264/9 |
| 2010/0294278 | A1 | 11/2010 | Mosier et al. | |
| 2018/0214645 | A1 | 8/2018 | Reevell | |

FOREIGN PATENT DOCUMENTS

| | | |
|---|---|---|
| EP | 3 111 978 A1 | 1/2017 |
| WO | 02/053216 A1 | 7/2002 |
| WO | 2003/061743 A1 | 7/2003 |
| WO | 2004/045688 A1 | 6/2004 |
| WO | 2005/049121 A1 | 6/2005 |
| WO | 2018/195086 A1 | 10/2018 |

OTHER PUBLICATIONS

International Search Report of PCT/EP2020/050808, mailed Apr. 20, 2020.

* cited by examiner

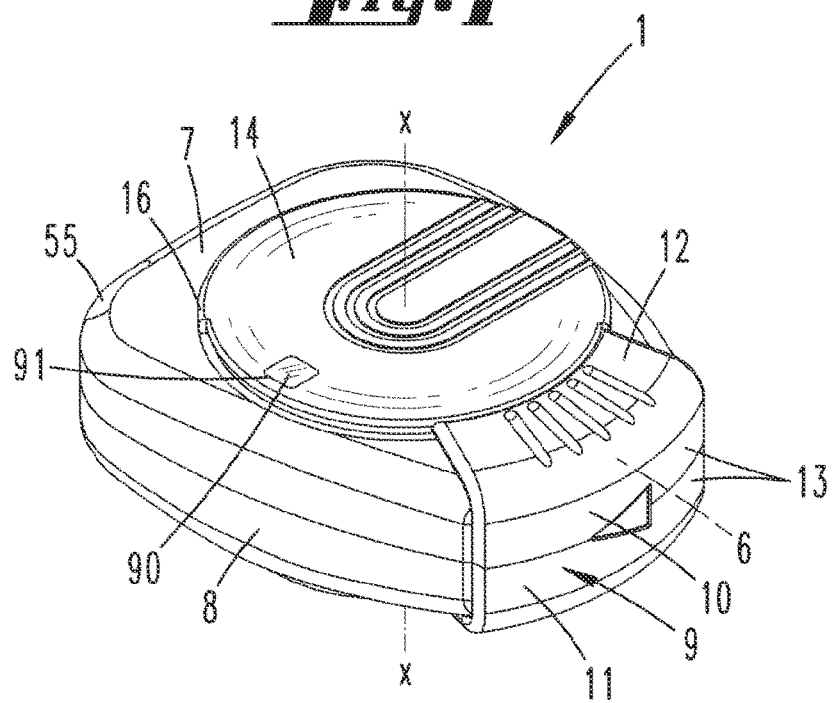
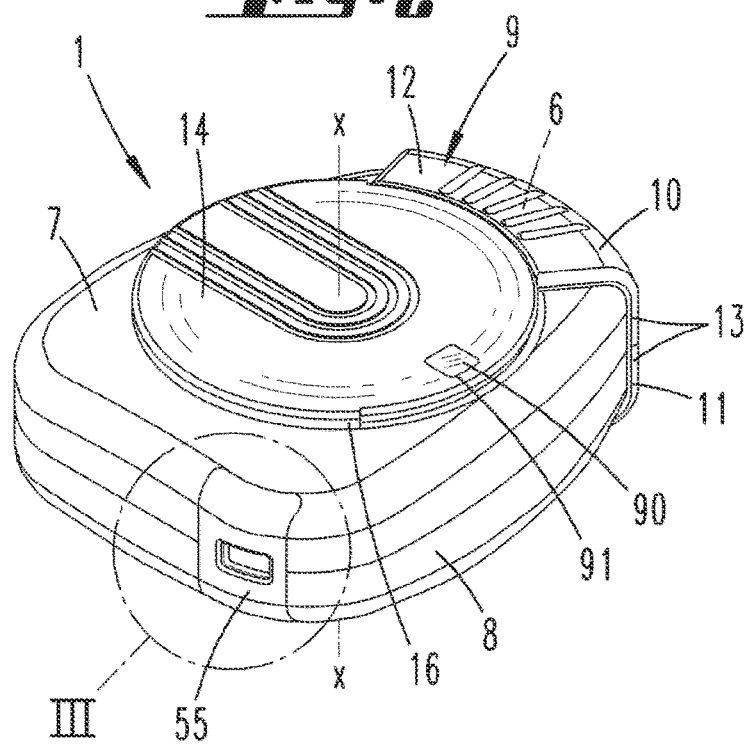

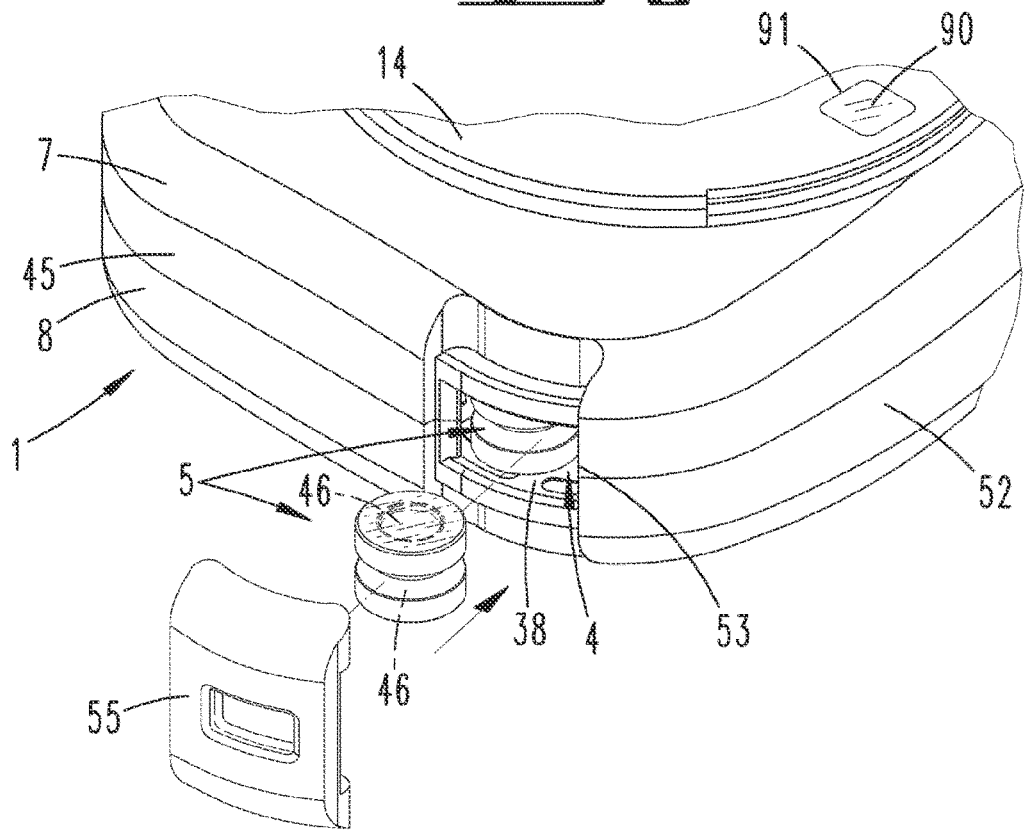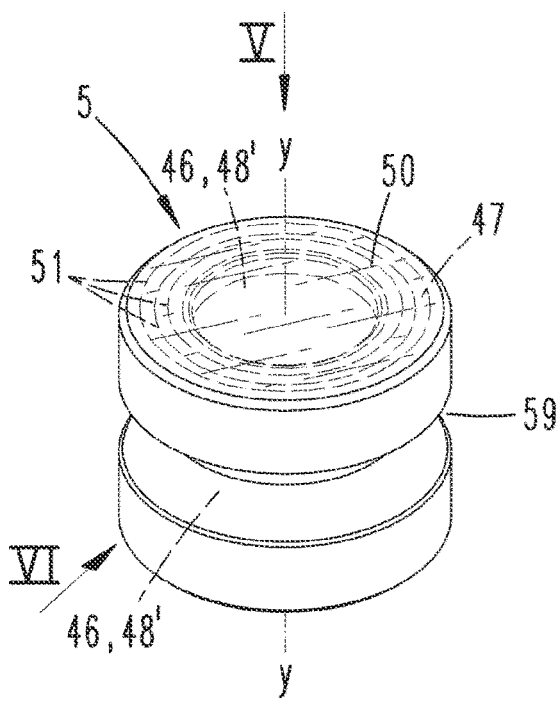

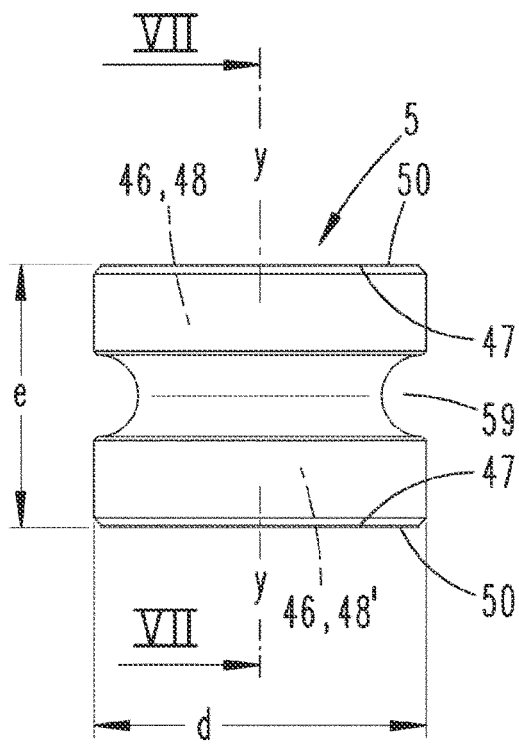
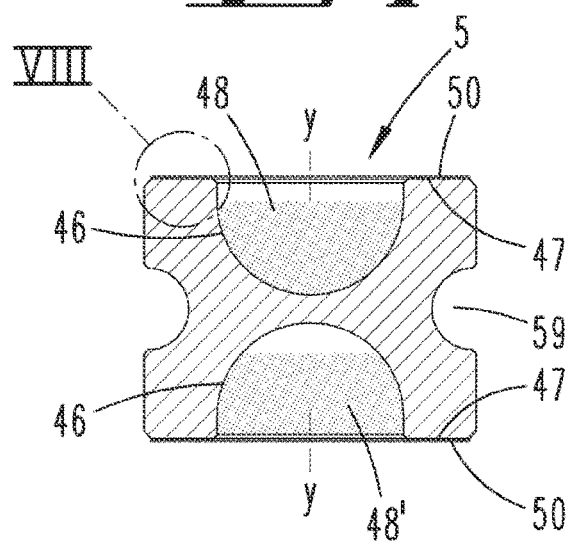
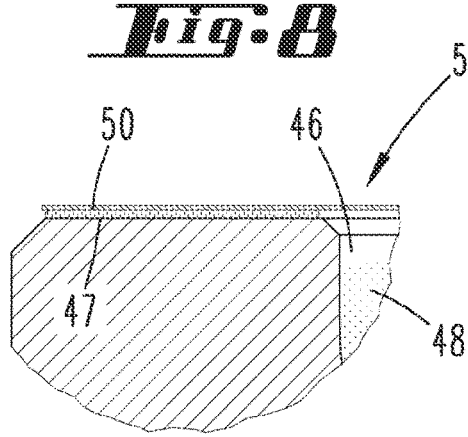
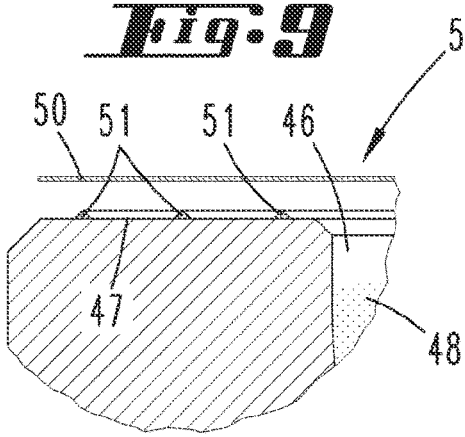
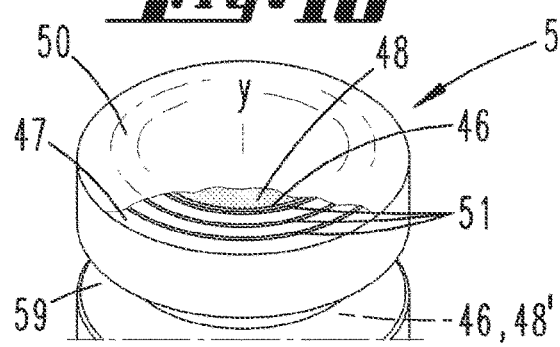

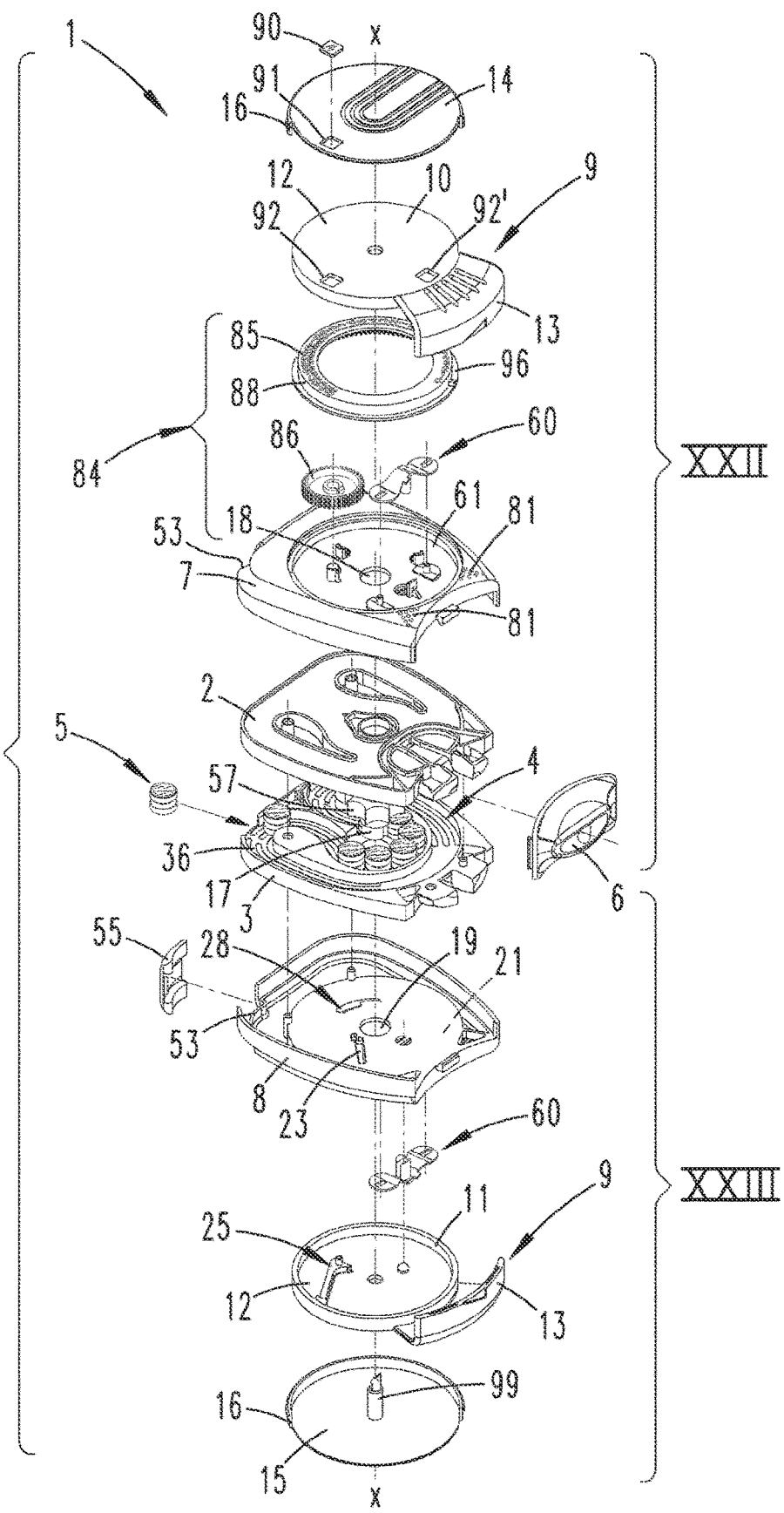

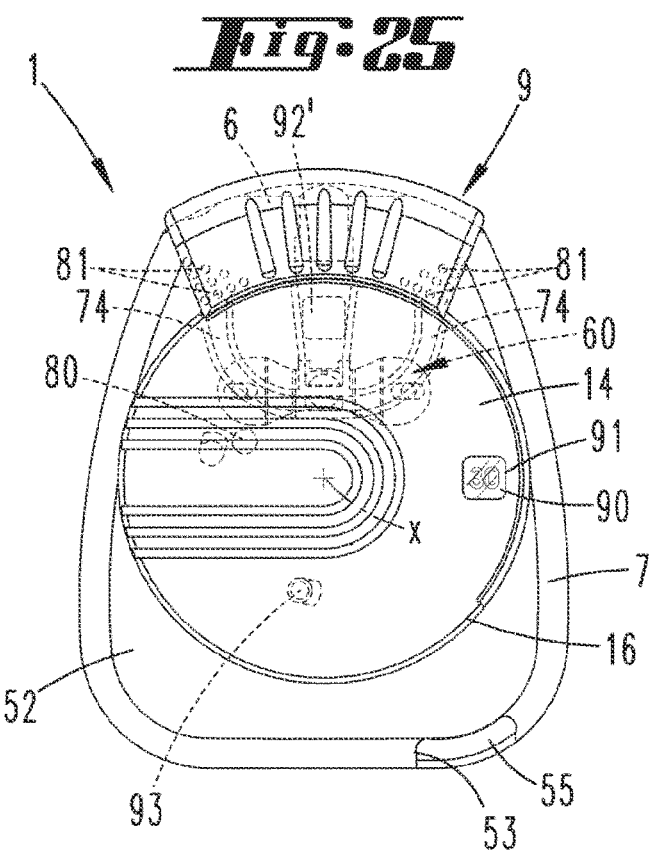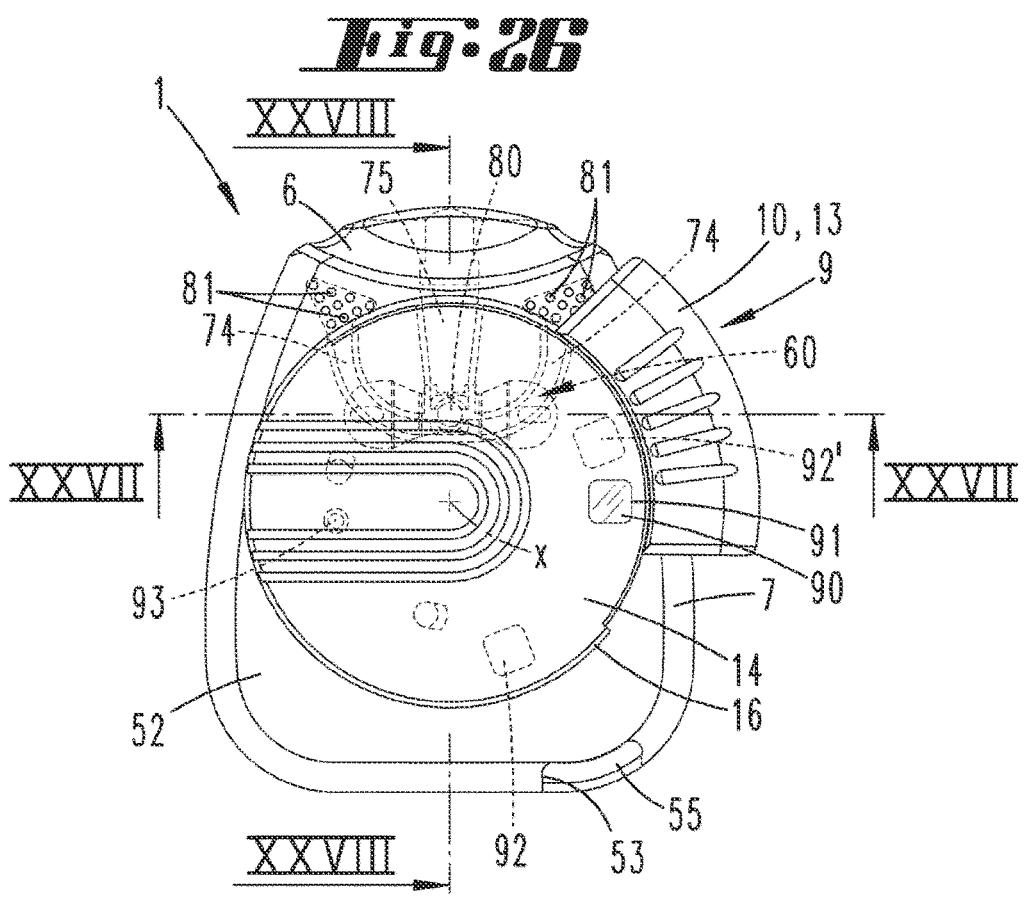

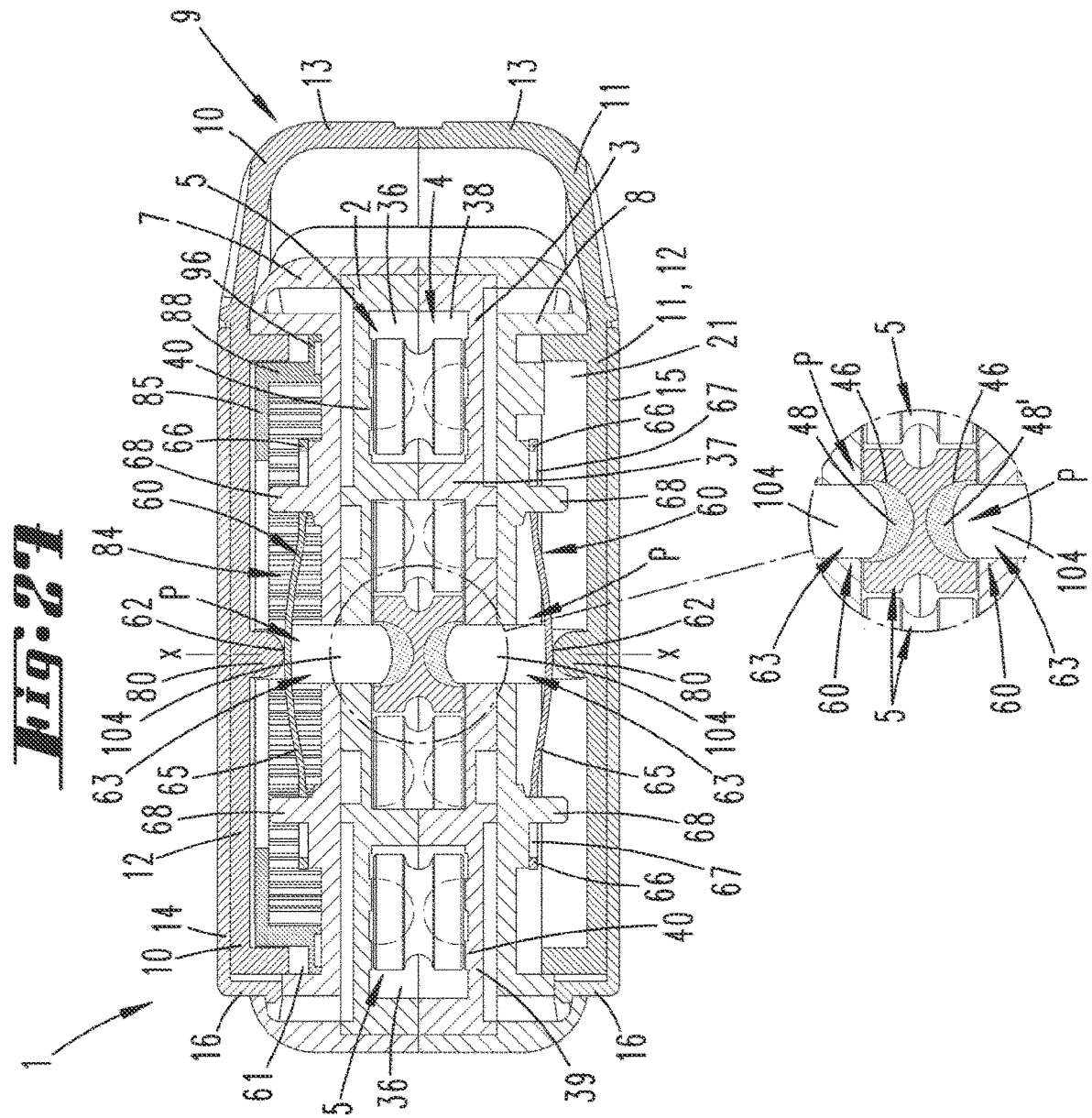

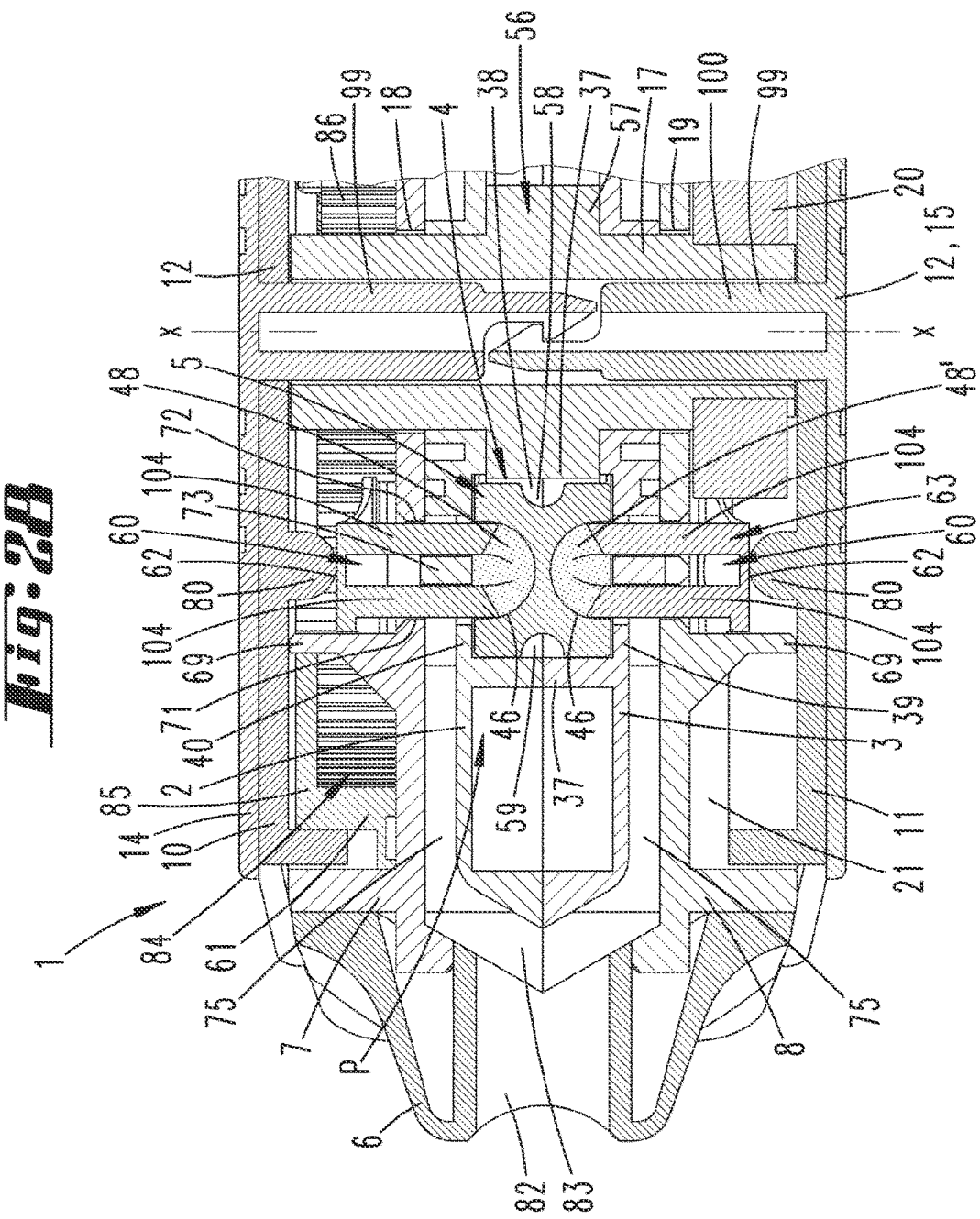

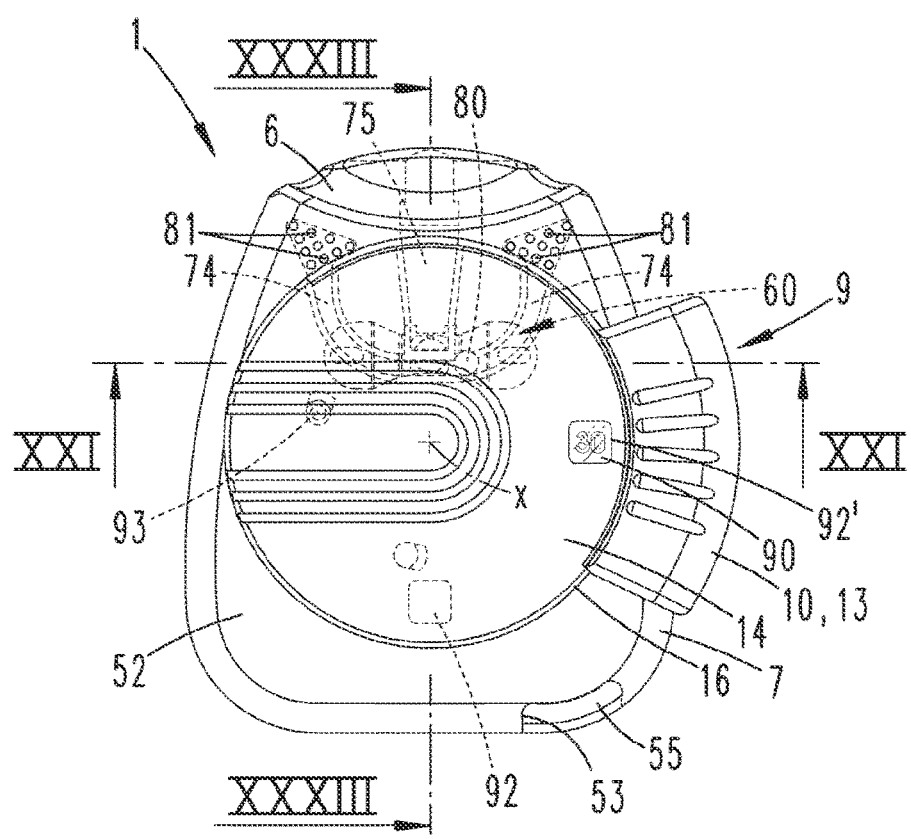

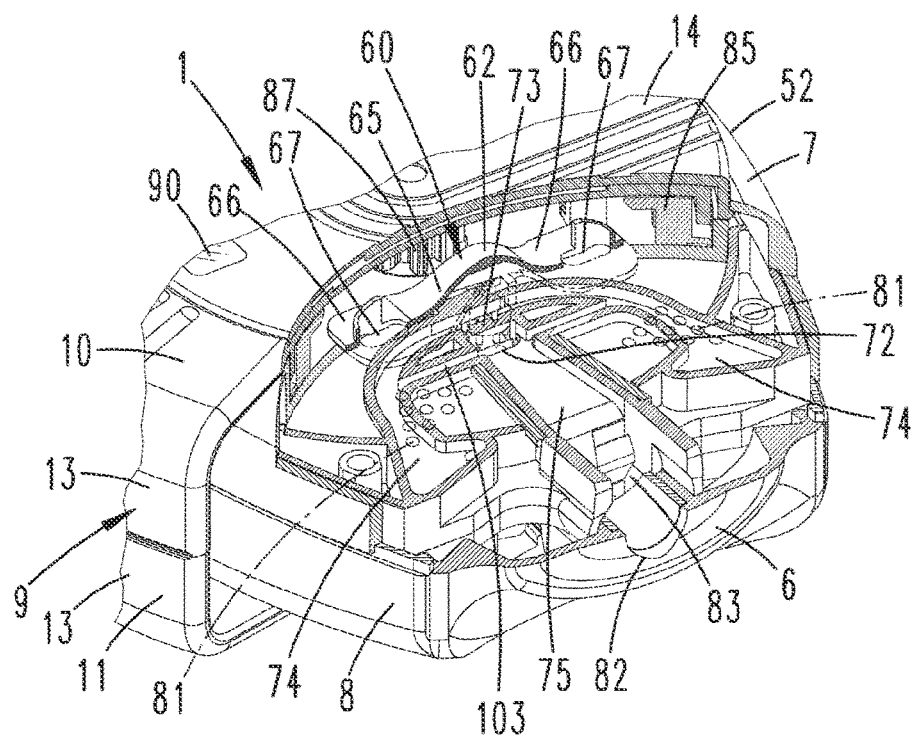

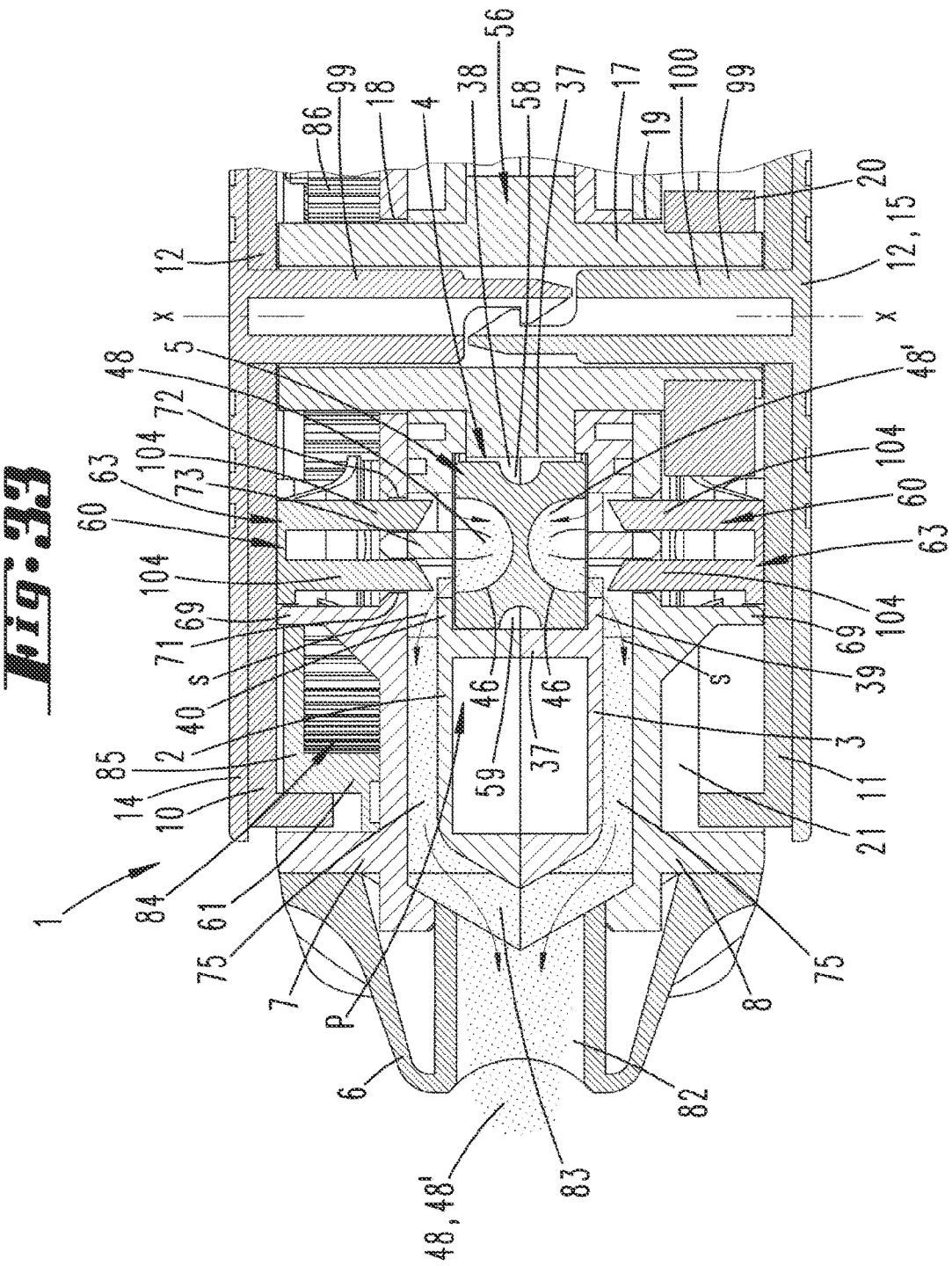

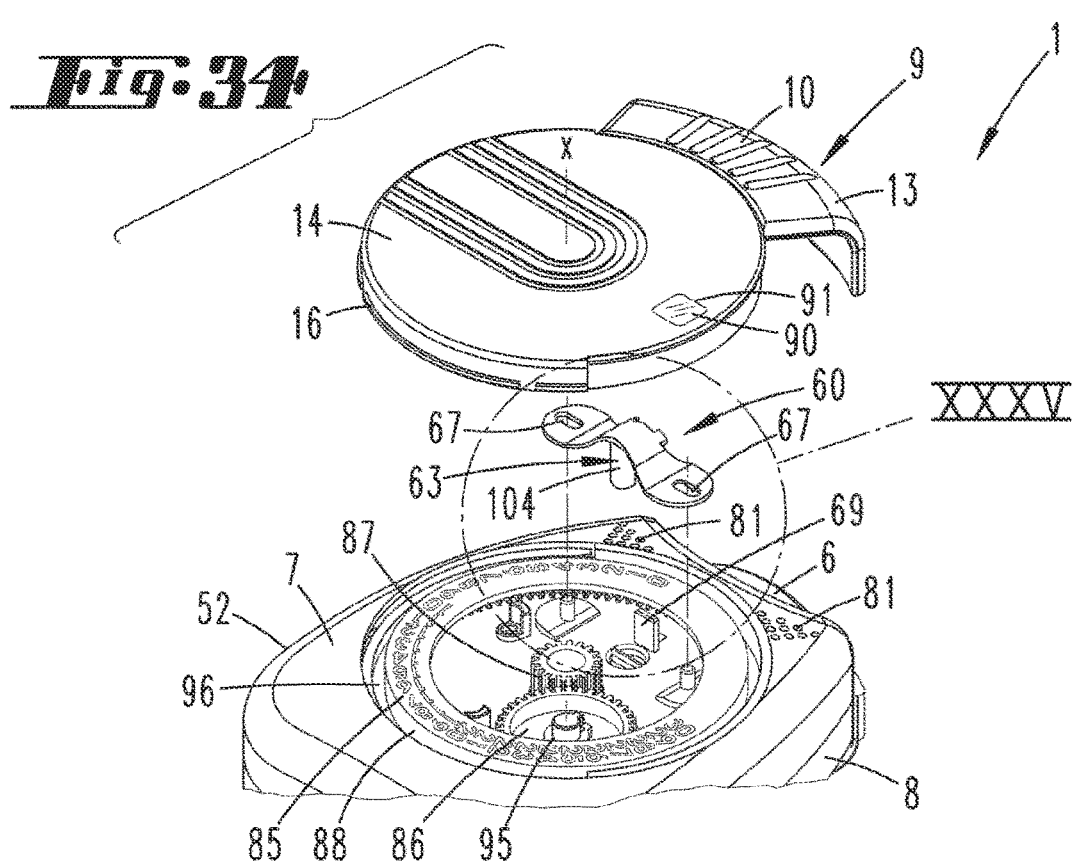
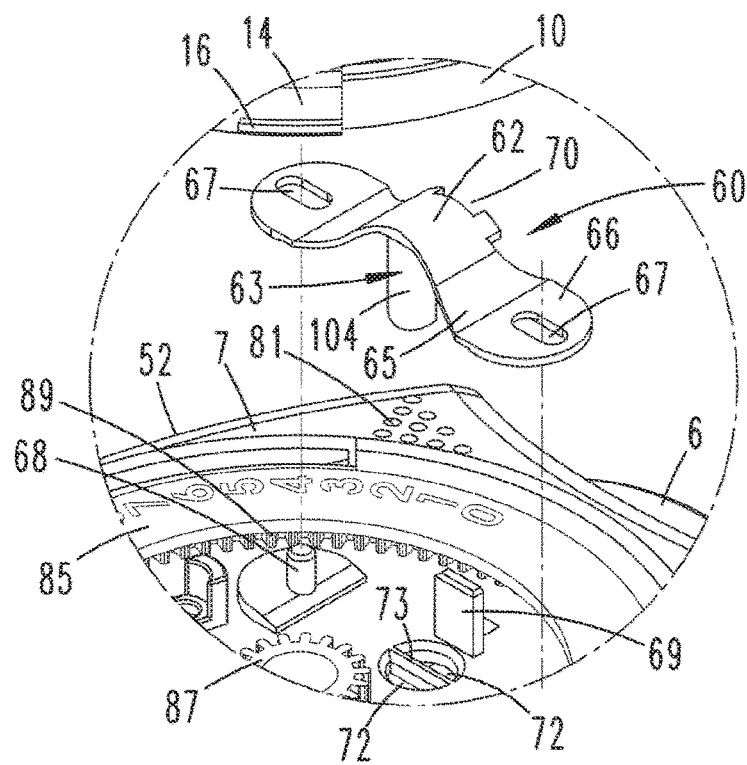

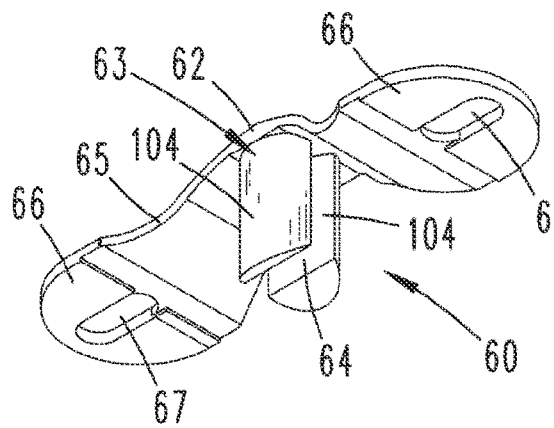
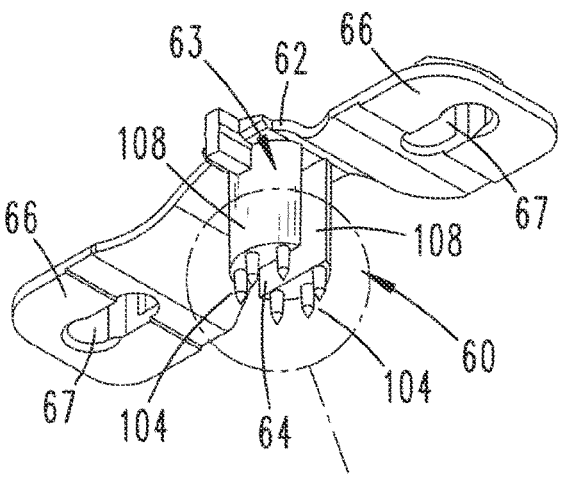
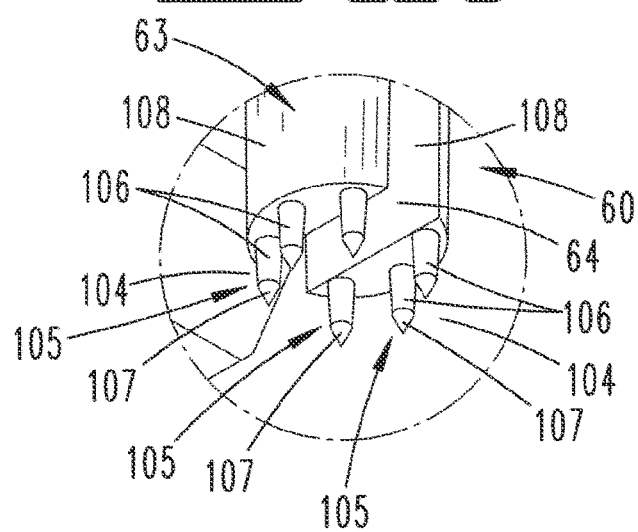
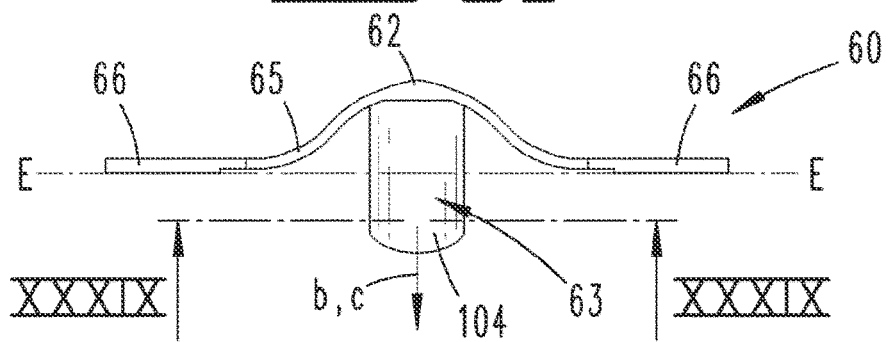

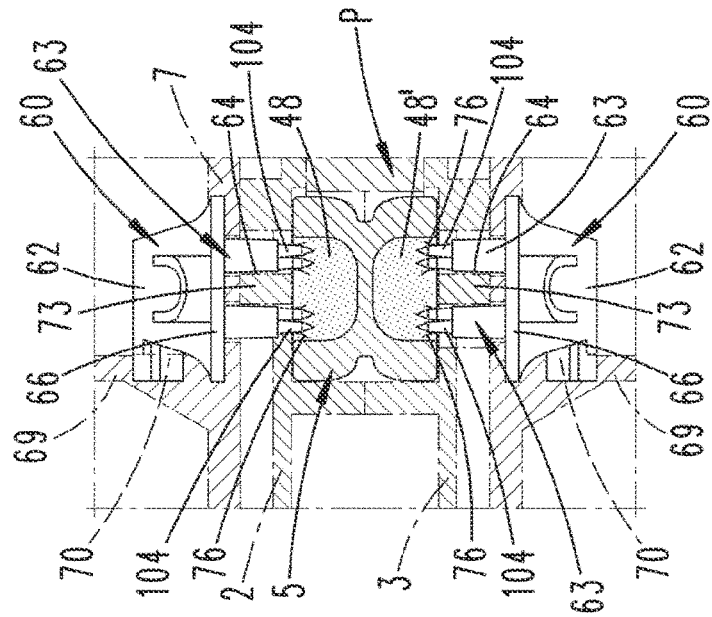
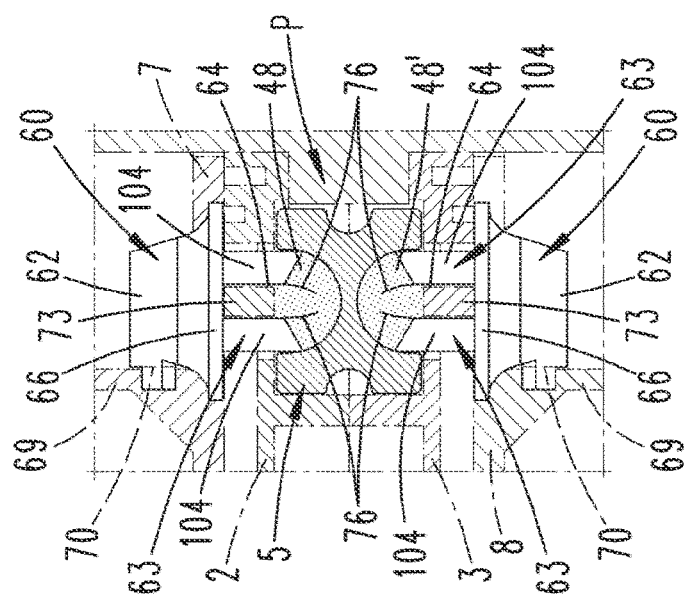

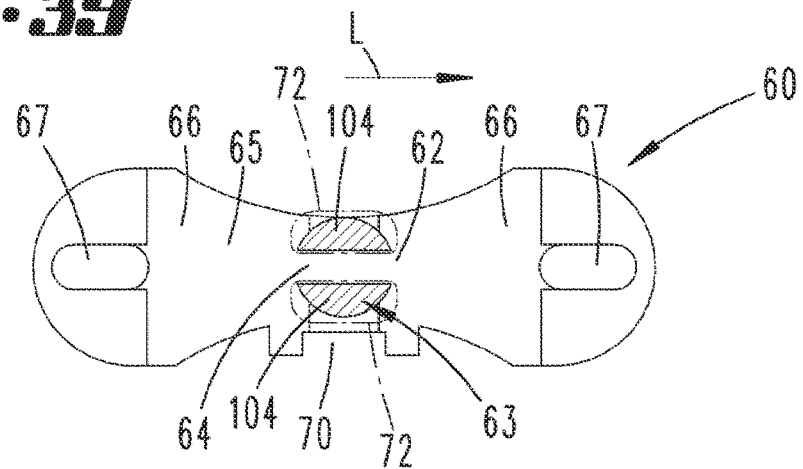
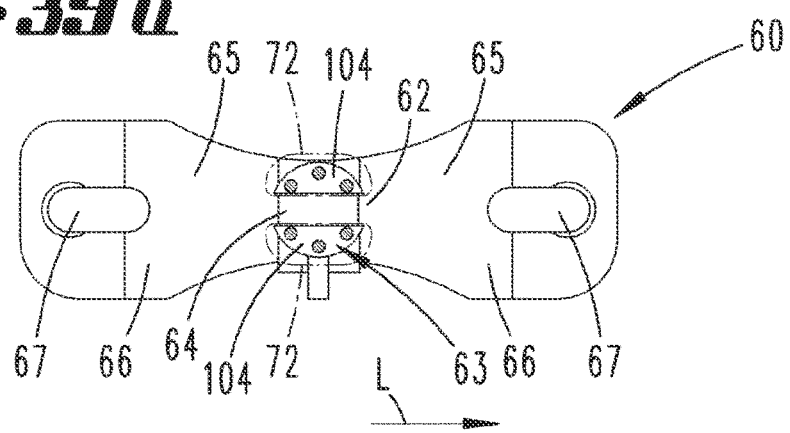
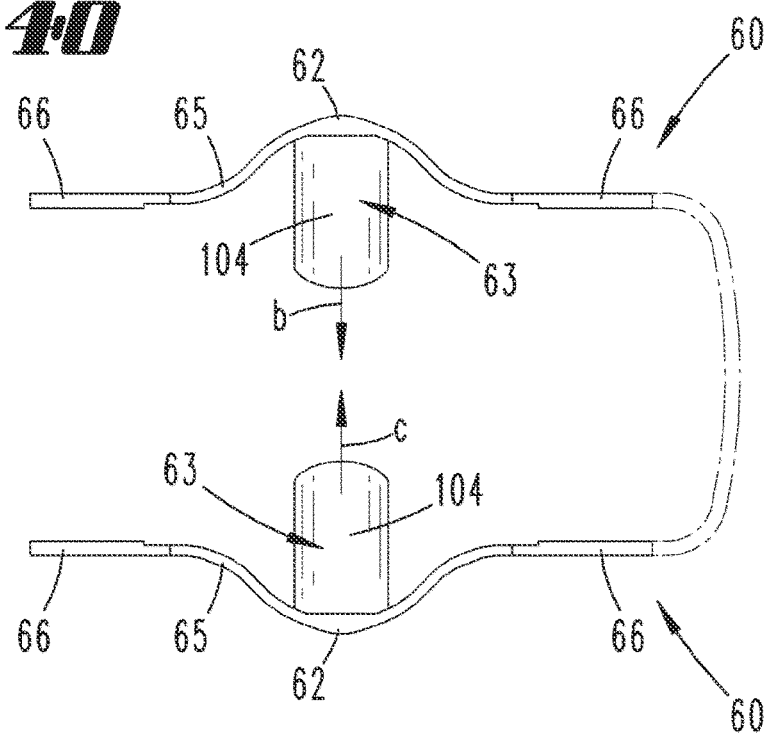

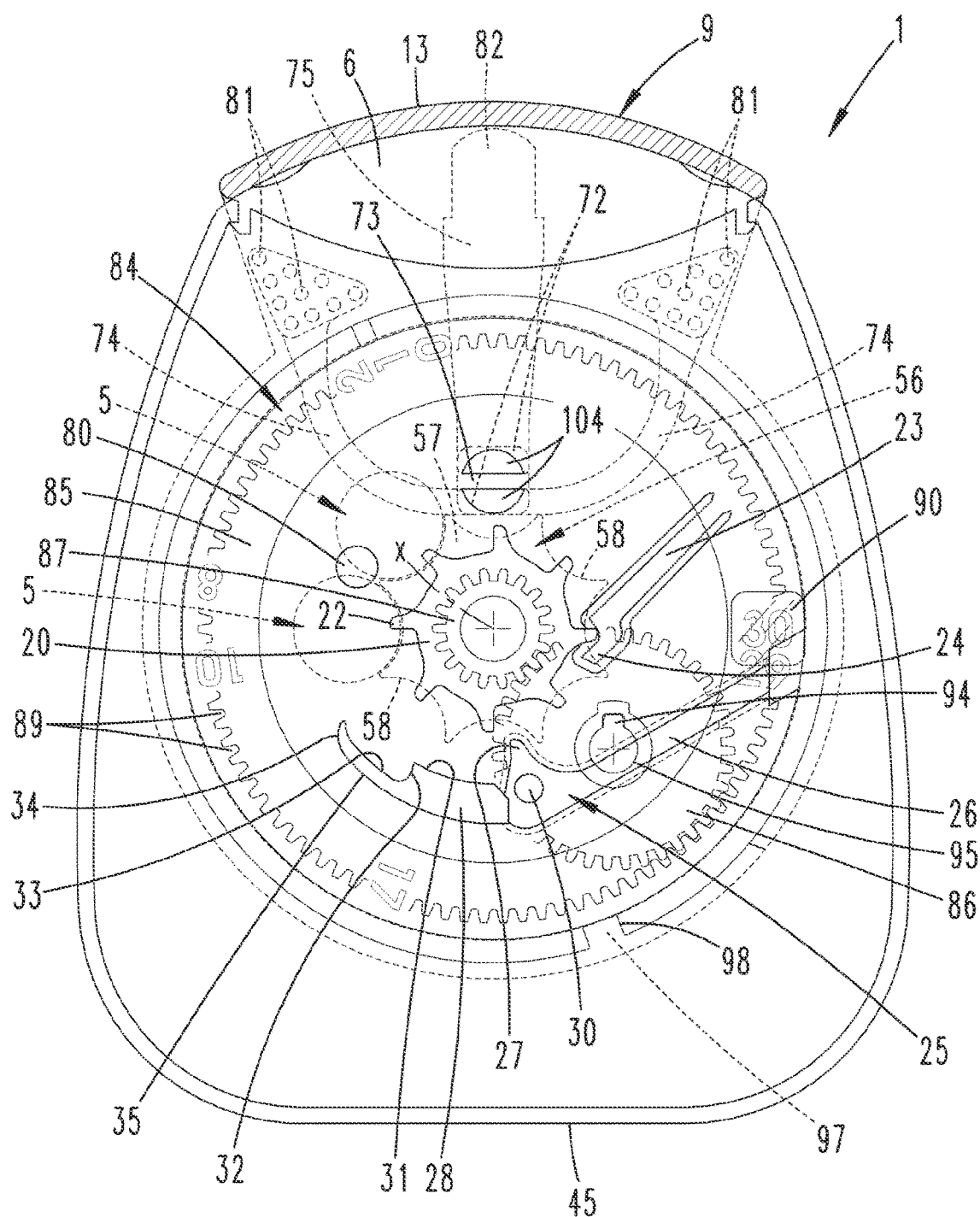

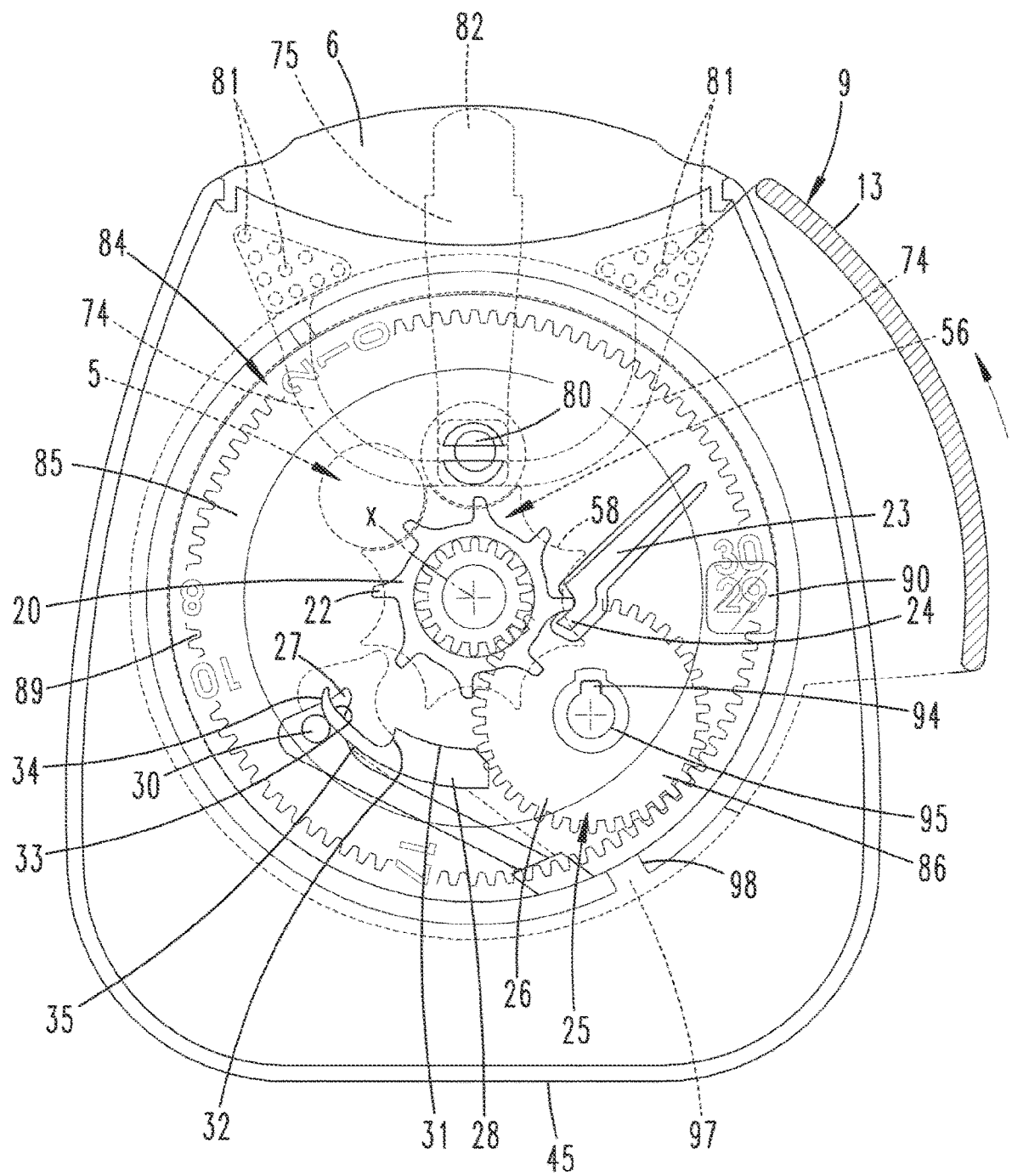

DEVICE FOR INHALING POWDER-TYPE SUBSTANCES

CROSS REFERENCE TO RELATED APPLICATIONS

This application is the National Stage of PCT/EP2020/050814 filed on Jan. 14, 2020, which claims priority under 35 U.S.C. §119 of German Application No. 10 2019 100 834.4 filed on Jan. 14, 2019 and German Application No. 10 2020 100 551.2 filed on Jan. 13, 2020, the disclosures of which are incorporated by reference. The international application under PCT article 21(2) was not published in English.

FIELD OF TECHNOLOGY

The invention initially relates to a device for inhaling powder-type substances, wherein the device has a mouthpiece, an insertion mechanism comprising a retaining part having an insertion means for opening a sub-region in a substance container containing substance, and a discharge channel for substance leading to the mouthpiece.

The invention further relates to a device for inhaling powder-type substances, comprising a plurality of substance containers that can be moved successively into an emptying position.

PRIOR ART

Devices of the discussed type serve for the inhalation, in particular for the inhalation of powder-type substances. The substance to be inhaled is provided in substance containers in portions, for dispensing via an air flow, which is built up in the course of an inhalation by the user. The substance container, which is moved into a dispensing-ready position for this purpose, is preferably opened prior to the build-up of the air flow by means of an insertion mechanism. The substance stored in the container in portions is dispelled via the opening resulting thereby and is transported to the mouthpiece via the discharge channel.

Devices are further known, in the case of which a plurality of substance containers are provided in the device arranged one behind the other in a displacement direction of the substance containers. The substance containers can be connected to one another thereby, for example as a result of the design of the substance containers in the manner of a blister pack or of a blister strip.

The substance containers are displaced successively into the emptying position with each actuation of the device.

A device of the discussed type is further known, for example from WO 2005/049 121 A1 (US 2007/0 131 225 A1), in which a plurality of substance containers are accommodated that are moved successively into an emptying position for emptying purposes.

WO 2003/061 743 A1 (U.S. Pat. No. 8,511,304 B2) discloses a device, in which the substance containers are provided in the device so as to be connected to one another in a chain-like manner in the manner of a strip blister, wherein the substance containers are formed in such a way that they store two optionally, and preferably, different substances in specified dosages. These two substances of a substance container are accommodated in sub-regions of the substance container, which are separated from one another until being emptied.

A device for inhaling powder-type substances is known from WO 2008/195086 A1, in the case of which two opposite insertion mechanisms, which can each be operated by hand, are formed. A corresponding device is further known from EP 3 111 978 A1, in the case of which the insertion mechanisms can likewise be operated by hand. A corresponding device is likewise known from US 2018/0214645 A1, in the case of which an insertion mechanism can be moved by hand, by means of which the substance container can then furthermore also be slid onto a second, stationary insertion mechanism.

A corresponding device is known from US 2010/0294278 A1, in the case of which it is possible to count blister packs accommodated therein. In addition, it is known therefrom to provide a cam disk, by means of which a vibration mechanism and an insertion mechanism can be acted on via connecting elements.

SUMMARY OF THE INVENTION

Based on the prior art according to WO 2018/195086 A1, the invention initially deals with the task of specifying a device for inhaling powder-type substances, which can in particular be handled in an operationally safe manner.

The invention further deals with the task of specifying an advantageous option for counting substance containers.

This object is initially solved in the case of device for inhaling powder-type substances, which focusses on that the device has a pivotable closure cap, and that both insertion mechanisms are simultaneously acted on by pivoting the closure cap.

The object is further solved in that the device has a pivotable closure cap and that both insertion mechanisms can be acted on simultaneously by pivoting the closure cap, wherein an action means stresses the insertion mechanisms in such a way that the retaining part can be displaced into an insertion position against the restoring force of spring arms by means of the insertion means.

The object is furthermore solved in that the device has a pivotable closure cap, and that both insertion mechanisms are acted on simultaneously by pivoting the closure cap, and that each insertion mechanism is moved out of the substance container again at the end of a pivoting movement of the closure cap from a device closed position into a device open position.

The object is finally solved in=that the substance containers can be moved via a drive shaft, which is accessible for a user from the outside, and the drive shaft acts on a counting wheel of a counter for displaying a number of emptied or non-emptied substance containers or of performed inhalations.

Due to the arrangement of two insertion mechanisms, which are preferably also separate from one another in relation to the retaining parts, the substance container can be opened in two regions, which are optionally distanced from one another. The openings, which can thus be reached at the substance container, can be formed so as to be distanced from one another. The regions can be formed so as to be capable of being reached from different directions.

The insertion mechanisms can also be provided in different planes, so that they are not necessarily aligned with one another—albeit running linearly, for example oppositely. Each insertion mechanism can have a separate retaining part, at which an insertion means can in each case be arranged. The insertion mechanisms can be designed differently, in particular in relation to the retaining parts and/or the insertion means, so that for example different opening cross sections can be attained in the substance container.

The insertion directions of the two insertion mechanisms can be essentially directed towards one another, but in relation to a top view or in a cross section, in which the insertion directions each present themselves in a line-like manner, can in addition optionally also draw an acute angle of, for example, a few angular degrees, such as further for example 5 or 10 degrees, up to approximately 90 degrees, but in additionally optionally also an obtuse angle of up to approximately 180, to one another. The lines of the insertion directions can thereby meet inside the substance container, but alternatively can also essentially run outside of the latter or also offset in height, without meeting, that is, in a skewed manner.

As a result of this design, the stored substance can be discharged in an improved manner through the two openings of the substance container. A favorable evaluation of the container results. As a result of the proposed design, a substance container, which has several, for example two cavities with substance, can in addition also be opened in a favorable manner. The two cavities can preferably have different powder-type medicaments, which, more preferably, can be combined in the discharge channel and/or in the mouthpiece only when performing the inhalation. Each cavity of the substance container is to therefore be opened in the emptying position. This is effected by means of the two insertion mechanisms, which are separate from one another.

With regard to the counter, the latter indirectly or directly provides the user with information on how many inhalations said user can still perform by means of the present device. This can be attained by counting the emptied substance containers or by counting the performed inhalations, respectively.

Such a counter can lend itself in particular in the case of devices, in the case of which the substance containers are accommodated without being connected to one another in a guide mechanism, which is attached to the device, for direct contact with one another, and can be moved by contact pressure propagating among the substance containers.

According to a possible design, an insertion means can has two insertion regions, which are separate from one another, which, for opening the substance container, can therefore each act separately thereon. They can thus form separate openings or separate opening regions in the substance container, if an insertion region in detail comprising several insertion protrusions is formed, see also the below-described several insertion tips. With regard to their insertion geometries, the insertion regions can be designed differently, even though an identical, in particular folding symmetrical design of the geometries of the insertion regions is preferred.

A free space, which extends in the transport direction of the substance containers, can thereby be provided between the insertion regions. A spacing of the insertion regions transversely to the transport direction of the substance containers can therefore result, in which resulting spacing region no perforation or no opening, respectively, of the substance container preferably takes place. This can be reflected in the opened substance container, for example in the form of a web or bridge section appearing between two opening regions. According to a possible design, a defined inflow opening and a defined outflow opening can thus result at the substance container, assigned to an insertion means, which openings are distanced from one another, for example by means of a web.

In a further possible design, an insertion region can have a connected, optionally integral insertion tip. In the alternative, however, two or more insertion tips can also be formed at an insertion region, assigned to the substance container, so that a multiple point-like perforation can result after an insertion process. For example, three or more, further for example four or five, up to ten insertion tips, can thus be provided for each insertion region.

An insertion tip can be formed, for example, in a mandrel-like manner, comprising a tip region adjacent to a cylindrical region. The largest diameter dimension of the tip region can correspond to the diameter dimension of the cylindrical region, which, in turn, preferably determines with its diameter dimension the free opening dimension of an opening in the substance container caused by the insertion tip.

According to a possible design, the displacement of the insertion mechanisms, in particular of the retaining parts, which in each case have the insertion means, into the insertion position for opening the substance container, can take place against the force of a spring, which restores the insertion mechanism. A conventional metal spring, in the form of a pressure spring or of a leaf spring, can be provided in this regard. A combined formation of the retaining part with a plastic spring is preferred in this regard. The retaining part, when the latter is formed as, for example, plastic injection-molded part, can be molded integrally and preferably of the same material as the plastic spring.

The plastic spring can thereby form two spring arms, which are directed oppositely. Via these spring arms, the retaining part can support itself on a device section, for example housing section, which is stationary relative to the retaining part.

In a preferred, unstressed basic position of each insertion mechanism, out of which basic position a displacement in particular of the retaining part with the insertion means arranged thereon for opening the substance container takes place, the plastic spring acting on the retaining part can essentially be relaxed, so that a restoring force of the plastic spring can result, which acts on the retaining part and which can be identical to or approximately identical to zero.

The spring arms of the plastic spring can simultaneously serve to guide the retaining part in response to an insertion process. For this purpose, the spring arms can interact with sections of the device, which are preferably stationary relative to the retaining parts. A reproducible insertion process can be carried out via this.

Starting at their free ends, the spring arms can have a guide recess, which interacts with a journal attached to the housing. The guide recess can be designed, for example, in a slit-like manner, into which the journal, which is attached to the housing, plunges. A securing of the spring arms and, via this, of the entire insertion mechanism, for example to the device housing, can also be attained via this journal.

In a side view, in which an insertion direction presents itself in a line-shaped manner and both spring arms are displayed in their longitudinal extension, the spring arms can be formed concavely, with the retaining part assigned to a longitudinal center of the combined spring arms. The plastic spring, which as a whole, is essentially comprised of the two spring arms, can therefore extend in a bridge-like or arch-like manner, optionally in each case comprising end-side foundation-type fastening and/or guide sections, wherein the retaining part can be arranged essentially in the arch zenith of the plastic spring between the two spring arms. The retaining part, with the insertion means thereof, can thereby, and preferably, plunge into the arch space formed by the concavely arranged spring arms.

In response to a corresponding displacement of the retaining part with the insertion means in the direction of the substance container, an even, bilateral guidance of the retaining part can thus be provided via the spring arms, wherein this displacement can take place against the restoring force of the spring arms, which builds up. Upon elimination of a stress, which effects this displacement of the retaining part into the insertion position, the retaining part can be moved back into the basic position with the insertion means and thus the entire insertion mechanism via the restoring force of the spring.

In a preferred design, both insertion mechanisms are designed identically.

Two discharge channels can also be provided, for example in each case assigned to an insertion mechanism and/or in each case assigned to a cavity of the substance container, when forming, for example, two cavities for each substance container. These discharge channels can be merged upstream of or also directly in the transition to the mouthpiece, viewed in the flow direction. Two partial flows with optionally different substance can thus be created from the cavity of the respective substance container, which meet in the region of the mouthpiece. A deflection baffle or the like can thereby further be provided in the mouthpiece or in the respective partial discharge channel, in order to attain an improved distribution and/or crumbling of substance. Such a swirling mechanism or the like can also be provided within the mouthpiece channel.

In further design, two suction channels can be provided—preferably assigned to one insertion region. In the course of, for example, an inhalation process, air, in particular ambient air, is thereby sucked in via both suction channels. In relation to their length in the flow direction and preferably also in relation to their cross sectional design, viewed transversely to the flow direction, the suction channels can be formed at least approximately identical. Both suction channels preferably lead directly to the substance container, which is in the emptying position.

In a flow direction upstream of the substance container, one or both suction channels can be connected to the discharge channel via a bypass. The bypass thereby provides a connecting channel of the two suction channels to one another, which preferably leads directly into the discharge channel, therefore by bypassing the preferably opened substance container. If only a limited air throughput volume can be guided via the flow path through the substance container, for example due to the given channel and container cross sections, an (excess) portion of the intake air can be guided through the bypass in the course of a conventional application by means of suction via the suction channels.

A plurality of substance containers can also be capable of being accommodated simultaneously in the device. This can be a row of substance containers, which is preferably not interrupted in the device, wherein the substance containers can be moved gradually into an emptying position for each individual inhalation process. The substance containers can be unconnected to one another and can be accommodated in a guide mechanism, which is attached to the device, for direct contact with one another, wherein the movement of the substance containers can be provided by a contact pressure propagating among the substance containers.

This movement of the substance containers can be capable of being attained via a drive shaft, which is accessible for the user from the outside.

Such a drive shaft can have a drivable drive pinion for the counter, which drive pinion can in addition act on a counting wheel via a transfer gear. The counting wheel can bear symbols, optionally, and preferably, numbers, which can be recognized from the outside, for example through a viewing window in the device housing.

Drive pinion, transfer gear, and counting wheel can interact in a gear-like manner, a step-down or also step-up ratio from the drive shaft to the counting wheel can therefore result.

For a proper arrangement in particular of the counting wheel, further in particular a proper alignment of the counting wheel in a basic position, in which, for example, the number of the emptied substance containers is zero, or the number of the non-emptied substance containers corresponds to the maximum number of substance containers in the device, it can be provided that alignment moldings for the transfer gear and the counting wheel are provided at the housing and/or between the transfer gear and the counting wheel, which provide for an assembly of the transfer gear and of the counting wheel (only) in a specified angular alignment. Assembly aids for inserting or attaching the transfer gear and of the counting wheel, respectively, are thus provided. The installation position is specified thereby. For this purpose, counter moldings formed at the transfer gear and/or at the counting wheel can be capable of being assigned to the housing-side alignment moldings. According to a preferred design, the transfer gear can thus be inserted into the housing only in a specified rotational position relative to the drive shaft, and the counting wheel only in a relative rotational position to the transfer gear and/or the drive shaft. Upon actuation of the device and preferred inhalation, the counting wheel is further moved out of these rotational positions via the drive shaft and the transfer gear.

The rotational position specified during the insertion, however, is preferably not yet a use initial position. The latter can optionally only be reached after the otherwise operational device has been equipped with the substance containers. In the course of this equipment, for example with each insertion of a substance container, the counting wheel is rotated further by one step in the direction of the use initial position thereof, which can only be reached with insertion of the last substance container into the device.

The device can have a pivotable closure cap. The mouthpiece can be covered, for example, in the non-use position of the device via said closure cap. The closure cap can thereby be displaced about a geometric pivot axis from a device closed position into a device open position, which geometric pivot axis can correspond to the geometric pivot axis of the drive shaft.

By pivoting the closure cap, the drive shaft can be acted on, via which drive shaft a displacement of a substance container into the emptying position can optionally be carried out indirectly or directly. The gradual displacement of the counting wheel can in addition also take place via the drive shaft.

In a possible design, both insertion mechanisms can also be acted on simultaneously by pivoting the closure cap. In this context, an influencing means can stress the insertion mechanism via the pivoting movement in such a way that the retaining part thereof is displaced in the insertion position with the insertion means against the restoring force of the spring arms. Both insertion mechanisms are thereby preferably displaced in the direction of the substance container in the same way. The rotational movement of the closure cap can thereby be transferred into an essentially linear movement of the insertion mechanisms, in particular in a linear movement of the insertion means. This linear movement of the insertion means can thereby be at hand essentially in the direction of the geometric pivot axis of the closure cap.

According to a further preferred design, each insertion mechanism can be moved out of the substance container again at the end of the pivoting movement of the closure cap from the device closed position into the device open position, which can additionally be stop-limited. This can be attained as a result of elimination of the stress acting on the insertion mechanisms via the closure cap. For this purpose, the arrangement and formation of the actuating means, which stresses the respective insertion mechanism and which is moved over the closure cap, can be provided constructively in such a way that this means leaves the insertion mechanisms even prior to reaching the closure cap pivot end position, so that they retract their insertion means out of the substance containers due to the spring restoring forces, and displace in the direction of the basic position thereof.

This closure cap pivot end position can, and preferably, correspond to the inhalation-ready position. By sucking on the mouthpiece, an air flow is built up, which evacuates the substance container or a plurality of cavities in the substance container. The discharged substance is transported via the one discharge channel or via the several discharge channels to the mouthpiece and is inhaled via the latter.

BRIEF DESCRIPTION OF THE DRAWINGS

The invention is described below on the basis of the enclosed drawing, which, however, only represents exemplary embodiments. A part, which is described only based on one of the exemplary embodiments and which is not replaced by a different part in the case of a further exemplary embodiment due to the special feature emphasized there, is thus also described for this further exemplary embodiment as at least possible part, which is present. In the drawing:

FIG. 1 shows a device for inhaling powder-type substances in perspective illustration, relating to the closed non-use position;

FIG. 2 shows the device according to FIG. 1 in a further perspective illustration;

FIG. 3 shows the enlargement of the region III prior to closing a housing-side insertion opening by means of a closure part;

FIG. 4 shows a substance container for the device in perspective individual illustration;

FIG. 5 shows the top view according to arrow V in FIG. 4;

FIG. 6 shows the view according to arrow VI in FIG. 4 against the substance container;

FIG. 7 shows the section according to line VII-VII in FIG. 6;

FIG. 8 shows the enlargement of the region VIII in FIG. 7, when the cover is fixed to the substance container;

FIG. 9 shows a detailed sectional illustration essentially corresponding to FIG. 8, but relating to a situation prior to fixing the cover to the substance container;

FIG. 10 shows a perspective detailed illustration of the substance container, partially cut, relating to the situation according to FIG. 9;

FIG. 11 shows an exploded perspective illustration of the device;

FIG. 24 shows a further illustration corresponding to

FIG. 24, relating to a situation in the course of a filling of the device with substance containers;

FIG. 25 shows a top view illustration of the device, essentially corresponding to FIG. 19;

FIG. 26 shows an illustration corresponding to FIG. 25, but in the course of a pivoting movement of a closure cap in the direction of an open position;

FIG. 27 shows the section according to the line XXVII-XXVII in FIG. 26;

FIG. 28 shows the section according to the line XXVIII-XXVIII in FIG. 26;

FIG. 29 shows a follow-up illustration for FIG. 26, relating to the closure cap open position;

FIG. 32*a* shows an illustration corresponding to FIG. 32, relating to an alternative embodiment;

FIG. 33 shows the section according to the line XXXIII-XXXIII in FIG. 29;

FIG. 34 shows a partially exploded perspective illustration of the device, relating to the region of an insertion mechanism;

FIG. 35 shows the enlarged illustration of the region XXXV in FIG. 34;

FIG. 36 shows the insertion mechanism in a perspective individual illustration;

FIG. 36*a* shows the insertion direction in a second embodiment;

FIG. 36*b* shows the enlargement of the region XXXVIb in FIG. 36*a;*

FIG. 37 shows the insertion mechanism in a side view;

FIG. 38 shows a sectional illustration relating to the arrangement of two insertion mechanisms in the device for puncturing two covers of a substance container;

FIG. 38*a* shows a sectional illustration according to FIG. 38, but relating to the embodiment according to FIG. 36*a;*

FIG. 39 shows the section according to the line XXXIX-XXXIX in FIG. 37;

FIG. 39a shows the sectional illustration according to FIG. 39, relating to the second embodiment;

FIG. 40 shows a side view illustration essentially corresponding to FIG. 37, but relating to the arrangement of two insertion mechanisms;

FIG. 41a shows an illustration corresponding to FIG. 41, but in the case of covers, which are pierced by an insertion direction according to FIG. 36a;

FIG. 42 shows an essentially schematic top view illustration onto the device, relating to the gear-like interaction of the counter and of the drive element for moving a substance container into an emptying position as well as the application of the insertion mechanism as a function of the pivoting displacement of the closure cap, relating to the cap closed position;

FIG. 48a shows an illustration corresponding to FIG. 48, but relating to the embodiment according to FIG. 32a;

FIG. 49 shows an intermediate position in the course of the pivoting of the closure cap from the open position in the direction of the closed position;

DESCRIPTION OF THE EMBODIMENTS

Figure 12:
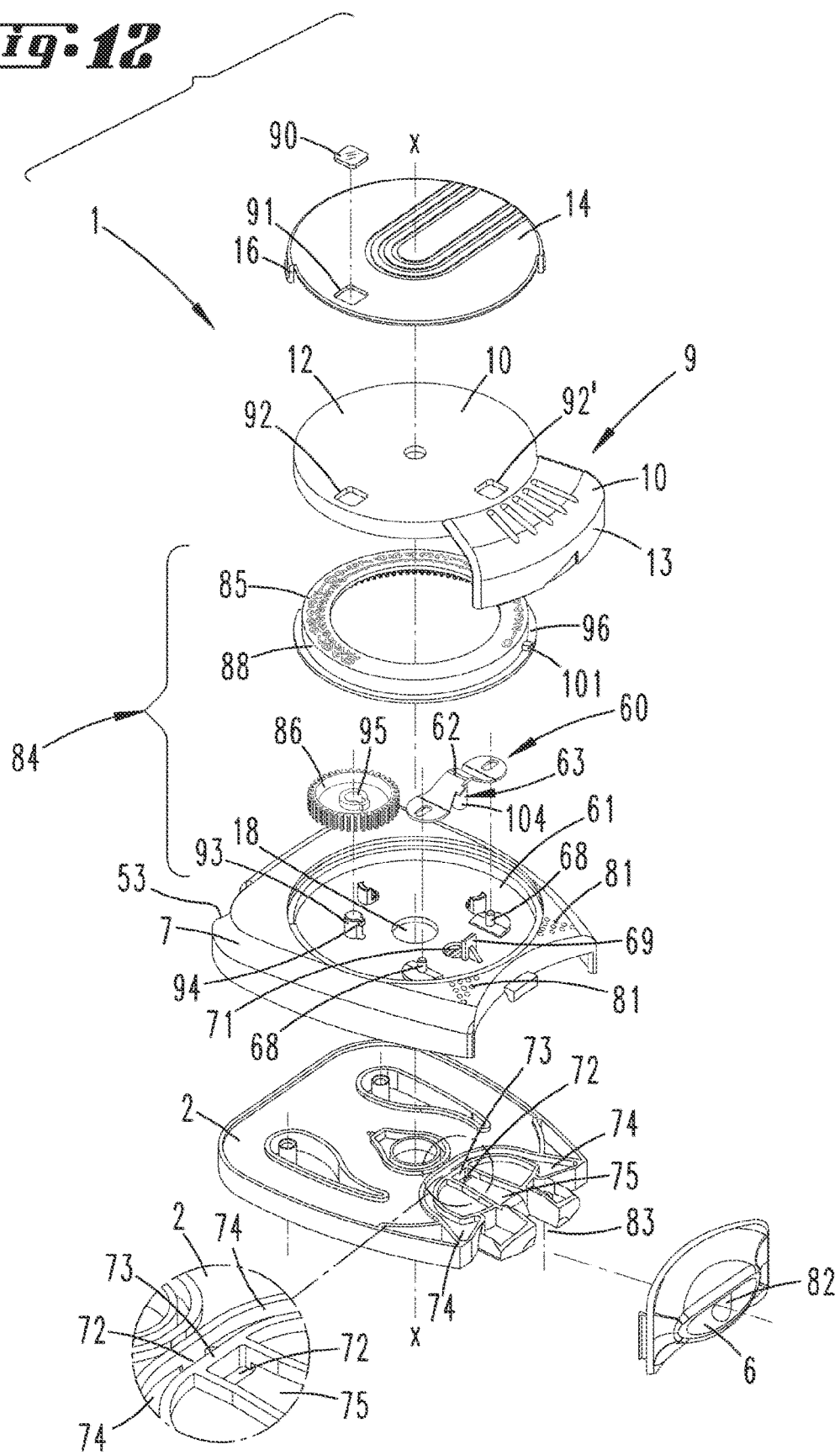
FIG. 12 shows an enlarged exploded perspective illustration of the region XII in FIG. 11.
Figure 13:
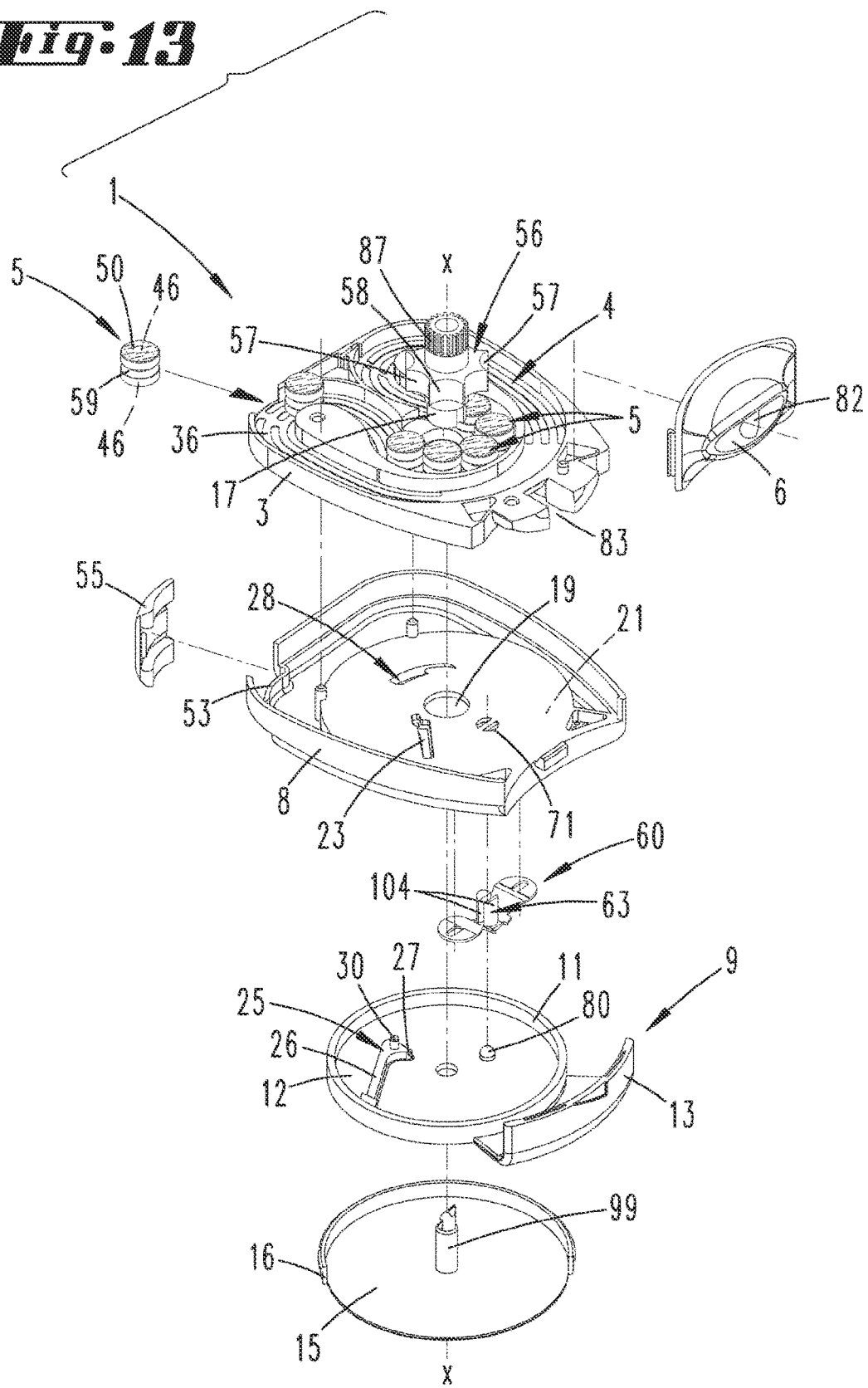
FIG. 13 shows the enlarged exploded perspective illustration of the region XIII in FIG. 11.
Figure 14:
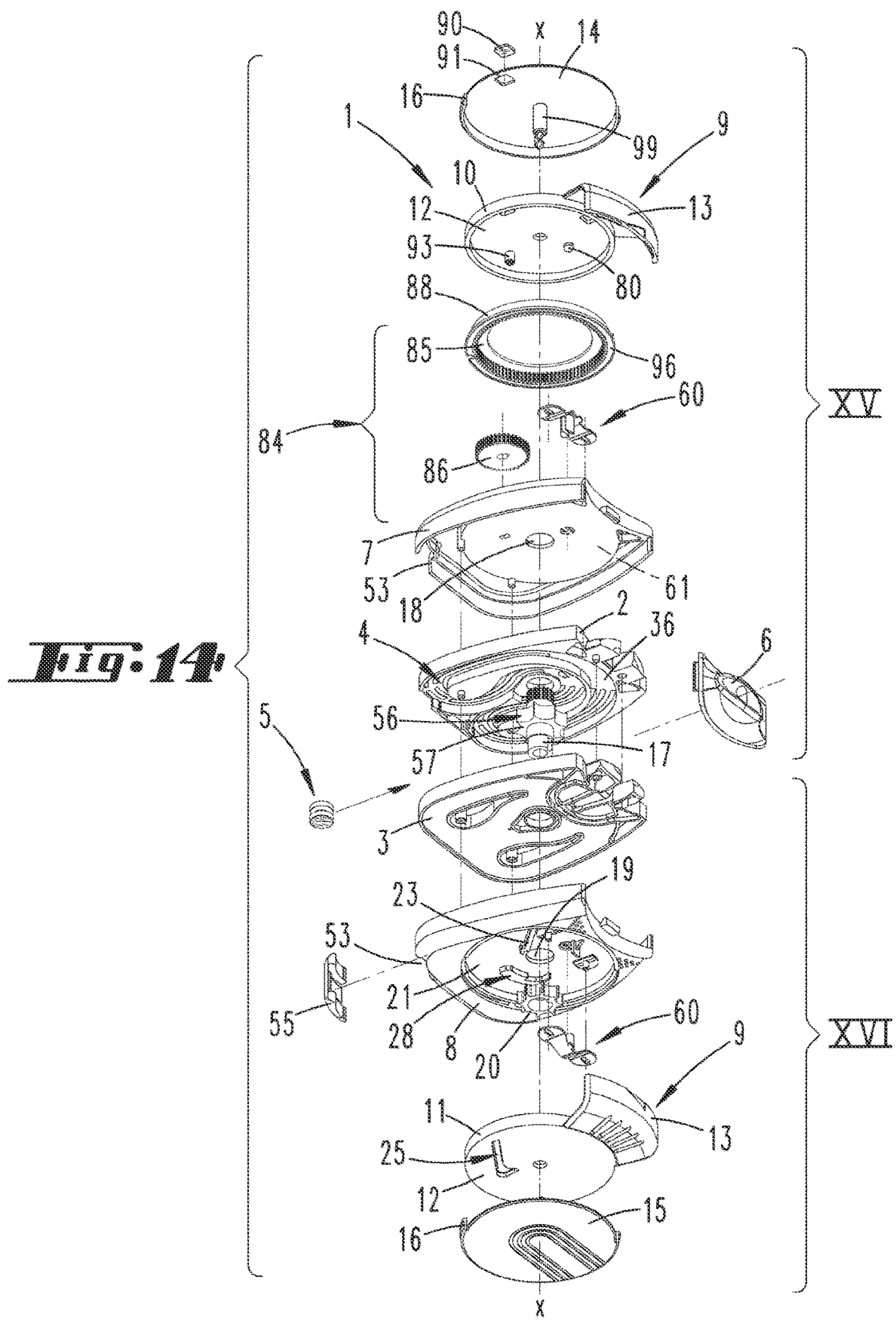
FIG. 14 shows the device in a further exploded perspective illustration.
Figure 15:
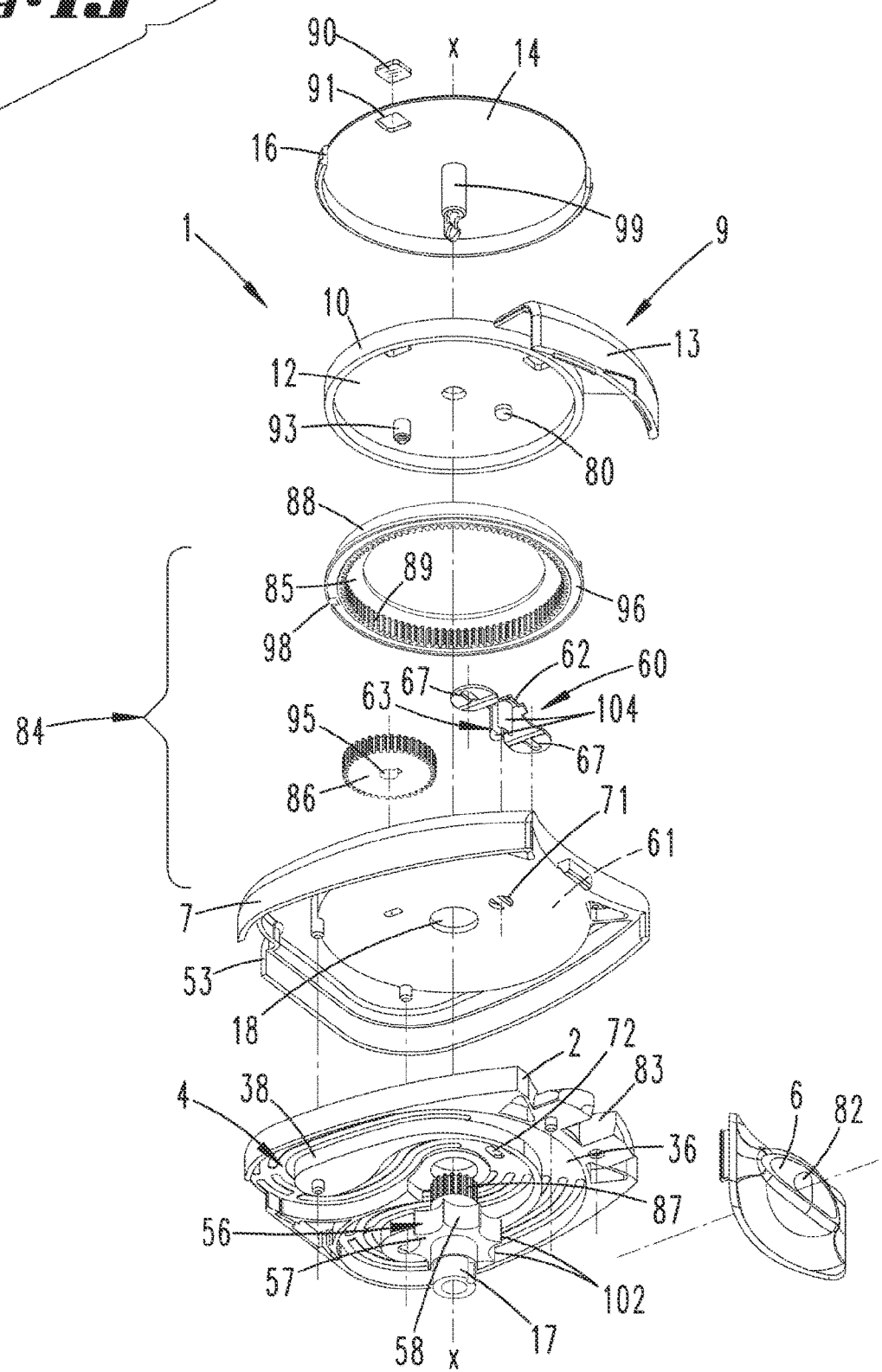
FIG. 15 shows an enlarged exploded perspective illustration of the region XV in FIG. 14.
Figure 16:
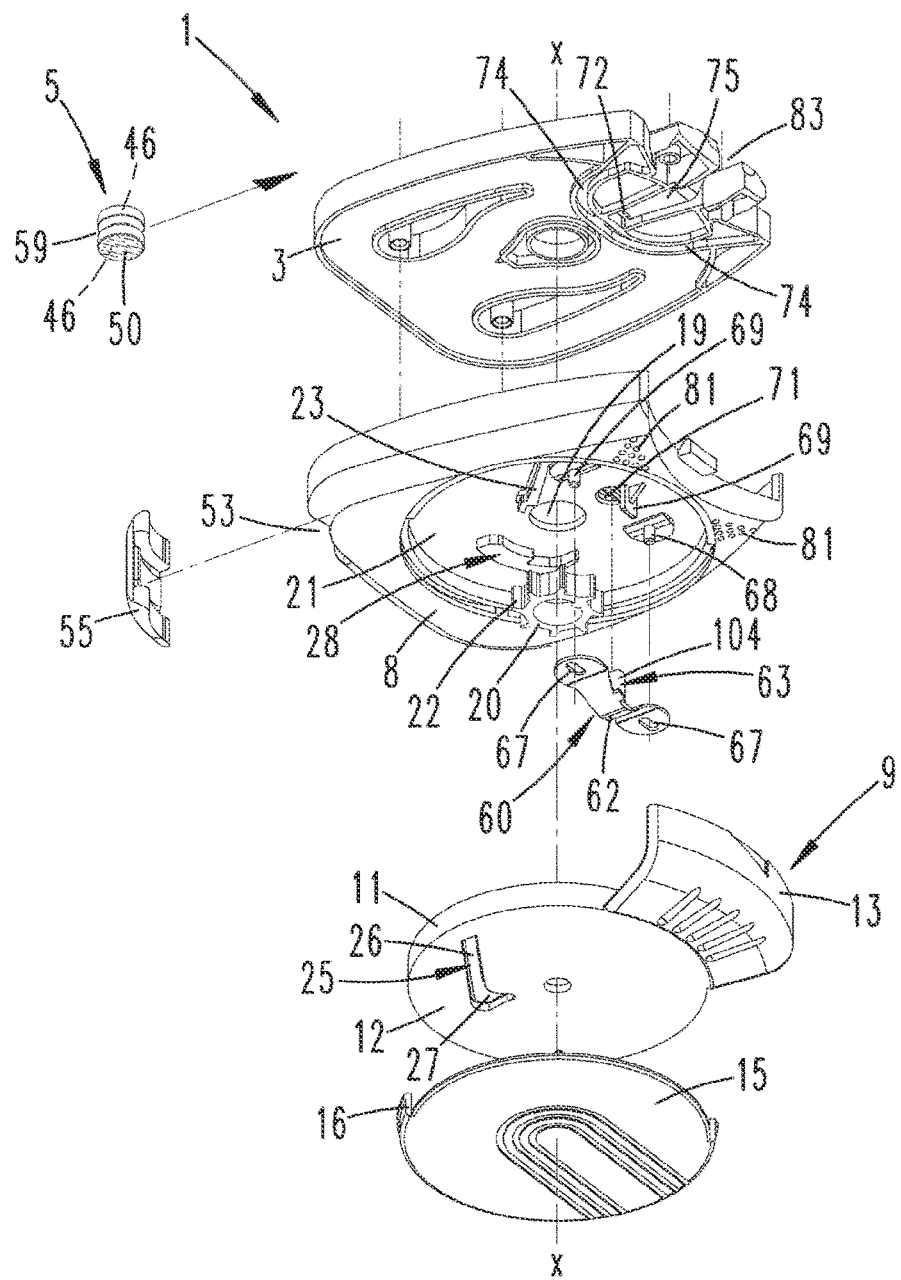
FIG. 16 shows an exploded perspective illustration of the region XVI in FIG. 14.

What is illustrated and described, initially with reference to FIGS. 1 and 2, is a device 1 for inhaling powder-type substances 48, 48'. The device 1 preferably has a mouthpiece 6, further an insertion mechanism 60 comprising insertion means 63, for opening a substance container 5, wherein preferably a plurality of substance containers 5 that can be moved successively into an emptying position P are provided, which are accommodated so as not to be connected to one another in direct contact with one another in a guide mechanism 4 attached to the device. A counter 84 is provided for counting and displaying the performed or still remaining inhalation processes.

The essential parts of the device 1 listed below can, and preferably, consist of a plastic, in particular hard plastic, such as polypropylene or polyethylene.

As can in particular be seen from the exploded perspective illustrations in FIGS. 12 to 17, the device 1 can initially essentially consist of a housing inner top part 2 and a housing inner bottom part 3, which, in direct contact with one another, leave the guide mechanism 4 for the substance containers 5 between them.

A mouthpiece 6, via which the inhalation process can be performed as a result of breathing in, is arranged at these housing inner parts 2 and 3.

A housing shell top part 7 as well as a housing shell bottom part 8, which, in direct contact with one another, accommodate the housing inner parts between them, essentially along outer edges facing one another, is further part of the device 1.

Together with the mouthpiece 6, housing shell top part 7 and housing shell bottom part 8 essentially form the outer contour of the device 1.

A closure cap 9 for the mouthpiece 6 is also essentially part of the device 1. The closure cap 9 is essentially formed from two closure cap parts, which are in each case assigned to the housing shell top part 7 and the housing shell bottom part 8, namely a closure cap top part 10 and a closure cap bottom part 11.

Each closure cap part thereby has a plate-like cover section 12 and a cap section 13, which protrudes outwards from this cover section 12 and which is formed in an L-shaped manner in a cross section.

Along the free outer edges of the L-shaped cap sections 13, which face one another, they can be connected to one another, for example as a result of an adhesion or welding, so that a cap with an essentially U-shaped cross section for covering the mouthpiece 6 results as a whole.

The ceiling sections 12 are provided in parallel alignment to one another and can be pivotably displaced around a geometric pivot axis x relative to the housing inner parts and the housing shell parts.

In addition, the closure cap top part 10 can be covered by a plate-like cover part 14, and the closure cap bottom part 11 can be underpinned by a likewise preferably plate-like base part 15.

The terms "top" and "bottom" or "base" or "cover", respectively, used with regard to the above-described housing refer solely to the graphic illustrations for example in FIGS. 12 to 17. In the case of the proposed device 1, a preferred alignment of the device for attaining a correct handling preferably does not result. For example, the top side can thus in fact also form the bottom side of the device 1 during the use.

Base part 15 and cover part 14 can, and as is illustrated, in each case have a collar 16, which partially revolves around the pivot axis x. The free front edges thereof, which point in the circumferential direction, can in each case provide a pivot stop for the closure cap 9 in the closure cap closed position and in the closure cap open position. The pivot angle of the closure cap 9 is therefore limited, thus for example to a pivot angle of approximately 50 to 70 degrees, preferably approximately 60 degrees.

Aligned along the geometric pivot axis x, a drive shaft 17 is provided in the device 1. Said drive shaft can, and also preferably, be pivotably or rotatably displaceable, respectively, relative to the closure cap 9 and the housing 52. The drive shaft 17 can experience a guidance in the region of adapted bores 18, 19 in the housing inner top part 2 and housing inner bottom part 3 or in the housing shell top part 7 and the housing shell bottom part 8, respectively.

The drive shaft 17 can also be accommodated on an axle body 100, which is stationary relative to the drive shaft 17. The axle body 100 can thereby be formed from hollow journals 99, which are in each case centrally molded to the cover part 14 and to the base part 15 and which face one another. The hollow journals 99 can, and preferably, be interlocked in such a way that the housing 52, which is tightly locked thereby as a whole, can preferably no longer be opened without destruction.

The drive shaft 17 can be driven in a ratchet-like manner via the closure cap 9 in such a way that, as a result of a pivoting displacement of the closure cap 9, in particular from a basic position, which closes the mouthpiece 6, into an open position, the drive shaft 17 is rotationally displaced by a specified angular dimension. A return pivoting displacement of the closure cap 9 from the open position into the closed position preferably does not effect a rotary entrainment of the drive shaft 17.

For this purpose, the drive shaft 17 is connected in a rotationally fixed manner to an actuating wheel 20. In the illustrated exemplary embodiment, said actuating wheel sits in a trough-like depression 21 of the housing shell bottom part 8 between this shell bottom part and the closure cap bottom part 11.

The actuating wheel 20 can, and as is illustrated, have essentially radially protruding entrainment protrusions 22. In the illustrated exemplary embodiment, eight such entertainment protrusions 22 are provided so as to be distributed evenly over the circumference, wherein each entrainment protrusion 22, deviating from a strict radial to the geometric pivot axis x, can draw an acute angle of approximately 20 to 30 degrees, so that an imaginary center line in relation to a top view, for example according to FIG. 42, can intersect the actuating wheel 20 in a secant-like manner by means of an entrainment protrusion 22.

In the region of the depression 21, the actuating wheel 20 interacts with a non-return device 23. The latter can, and as is illustrated, be formed as resilient section of the housing shell bottom part 8, integrally with the latter.

The non-return device 23 is provided with a locking lug 24, for interaction with the entrainment protrusions 22 of the actuating wheel 20, wherein the locking lug 24 can further be formed in such a way that it can be overrun by the entrainment protrusions 22 only in the specified direction of rotation a of the actuating wheel 20. In response to such an overrunning, the locking lug 24 rebounds accordingly.

Such an overrunning is not possible against the direction of rotation a. On the contrary, the locking lug 24 of the non-return device 23 blocks a rotation of the actuating wheel 20 in this direction.

The actuating wheel 20 and via the latter, the drive shaft 17, is rotationally movable as a result of the impact of a drive part 25 on one of the entrainment protrusions 22 of the actuating wheel 20. The drive part 25 can, and preferably, be part of the closure cap 9, in particular part of the closure cap bottom part 11.

The drive part 25 can thereby be formed integrally and of the same material as the corresponding closure cap bottom part 11. The drive part 25 can thereby further have a spring arm 26, which is rooted on the cover section 12 and which forms a protrusion-like entrainment lug 27 on the end side. This entrainment lug 27 is suitable for interacting with an entrainment protrusion 22 of the actuating wheel 20.

As a result of the arrangement of the entrainment lug 27 on a spring arm 26, the entrainment lug 27 is designed so as to be resiliently deflectable essentially transversely to the longitudinal extension of the spring arm 26.

In a basic position of the drive part 25, which corresponds to the mouthpiece closed position of the closure cap 9, for example according to FIG. 42, the drive part 25 is inserted in an unstressed manner and preferably without spring deflection in the depression 21. A controlled displacement of the drive part 25 against a restoring force appearing thereby in the region of the spring arm 26 only takes place with the pivoting of the closure cap 9 from the closed position in the direction of the open position.

This control is reached via a slotted guide 28, which is stationary relative to the drive part 25 and the actuating wheel 20. Said slotted guide can, and as is illustrated, be provided on the base side of the depression 21. In addition, the slotted guide 28 can be formed as a rib, which runs essentially concentrically to the pivot axis x and which is stepped in the circumferential direction, wherein said rib initially has a control surface 29 for interacting with a control journal 30, which is molded to the drive part 25 in the region of the entrainment lug 27.

Figure 43:
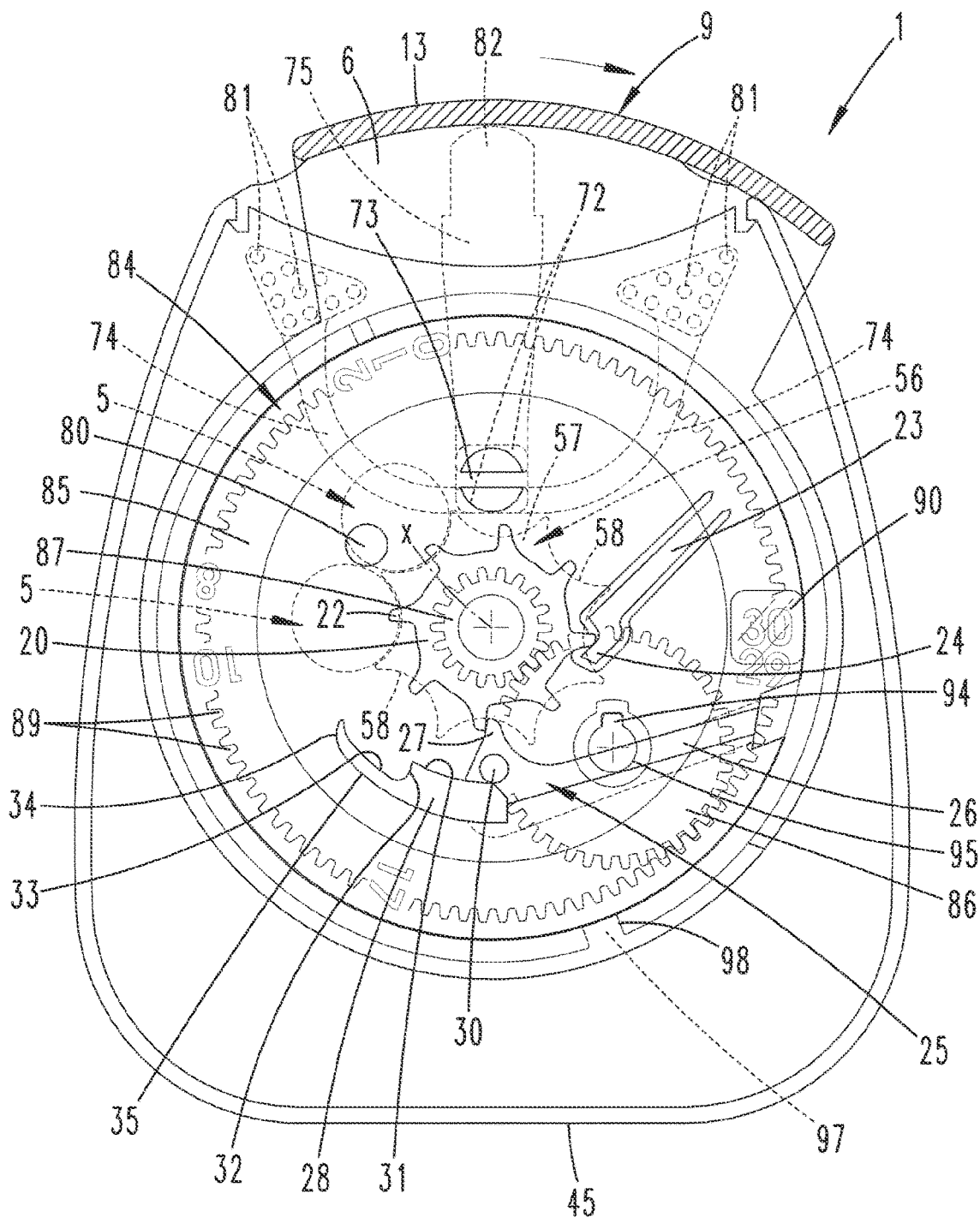
FIG. 43 shows a follow-up illustration for FIG. 42, in the course of the pivoting movement of the closure cap in the direction of the open position.
Figure 44:
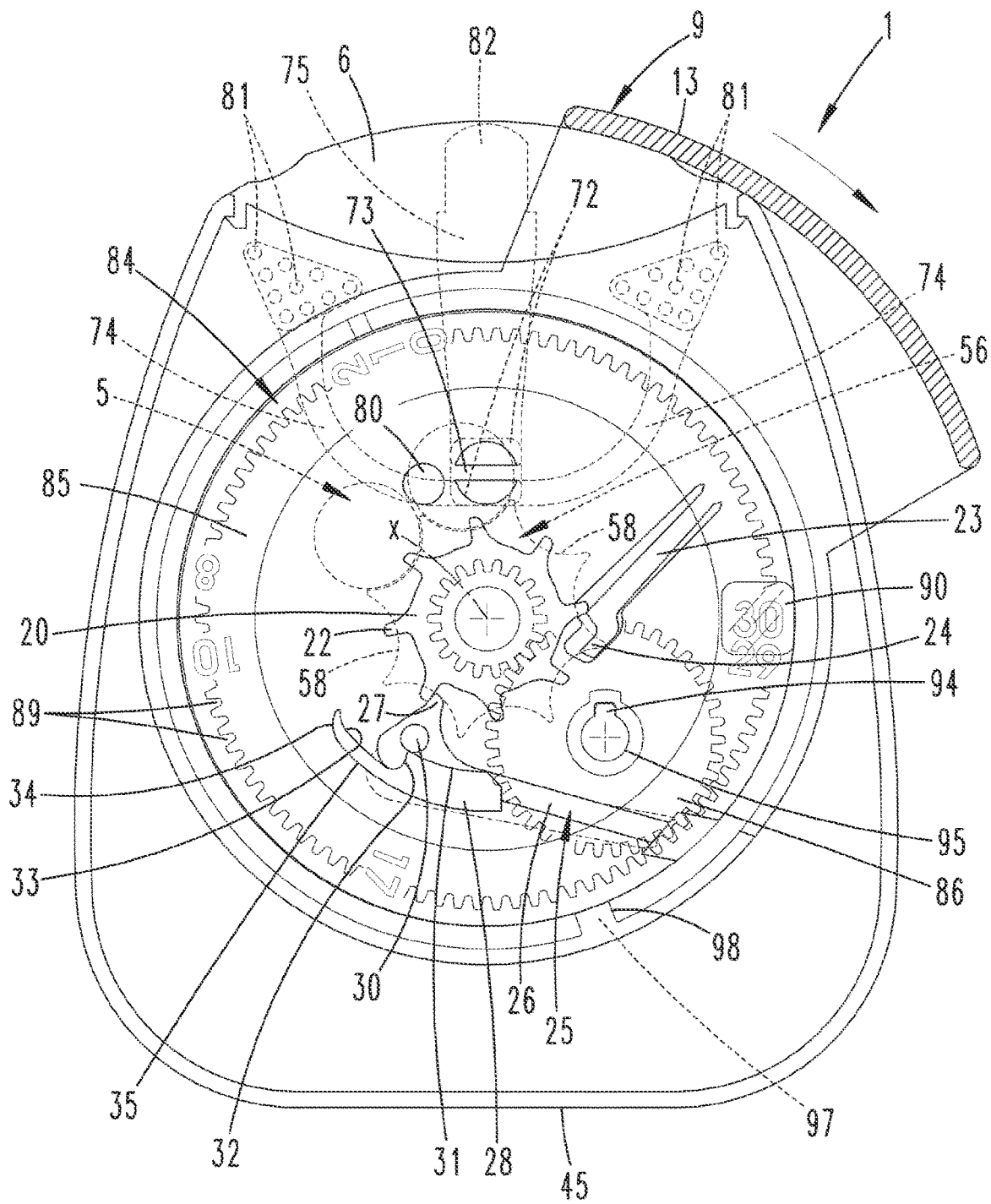
FIG. 44 shows a follow-up illustration for FIG. 43.
Figure 45:
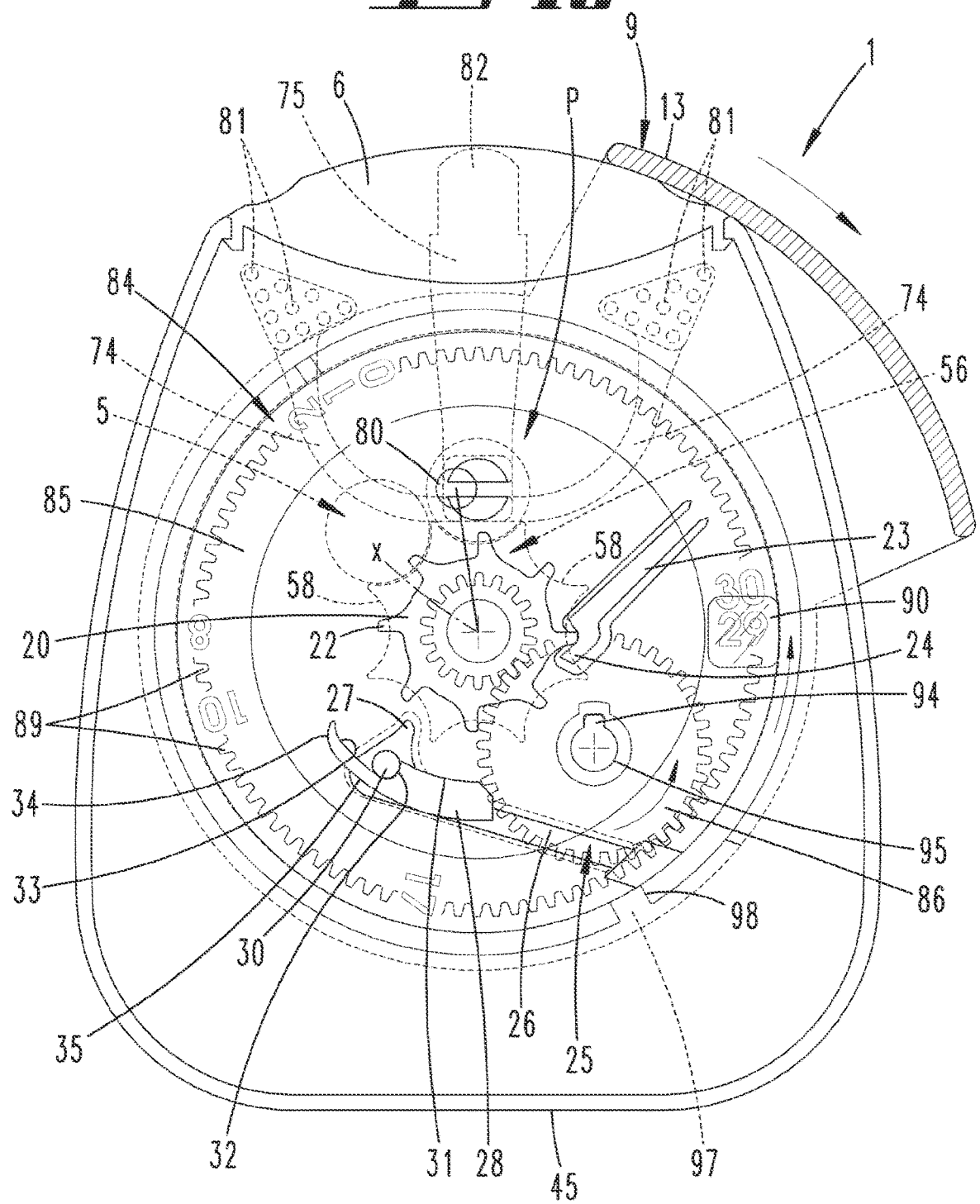
FIG. 45 shows a follow-up illustration for FIG. 44, relating to an intermediate position, in which the substance container has reached the emptying position.
Figure 46:
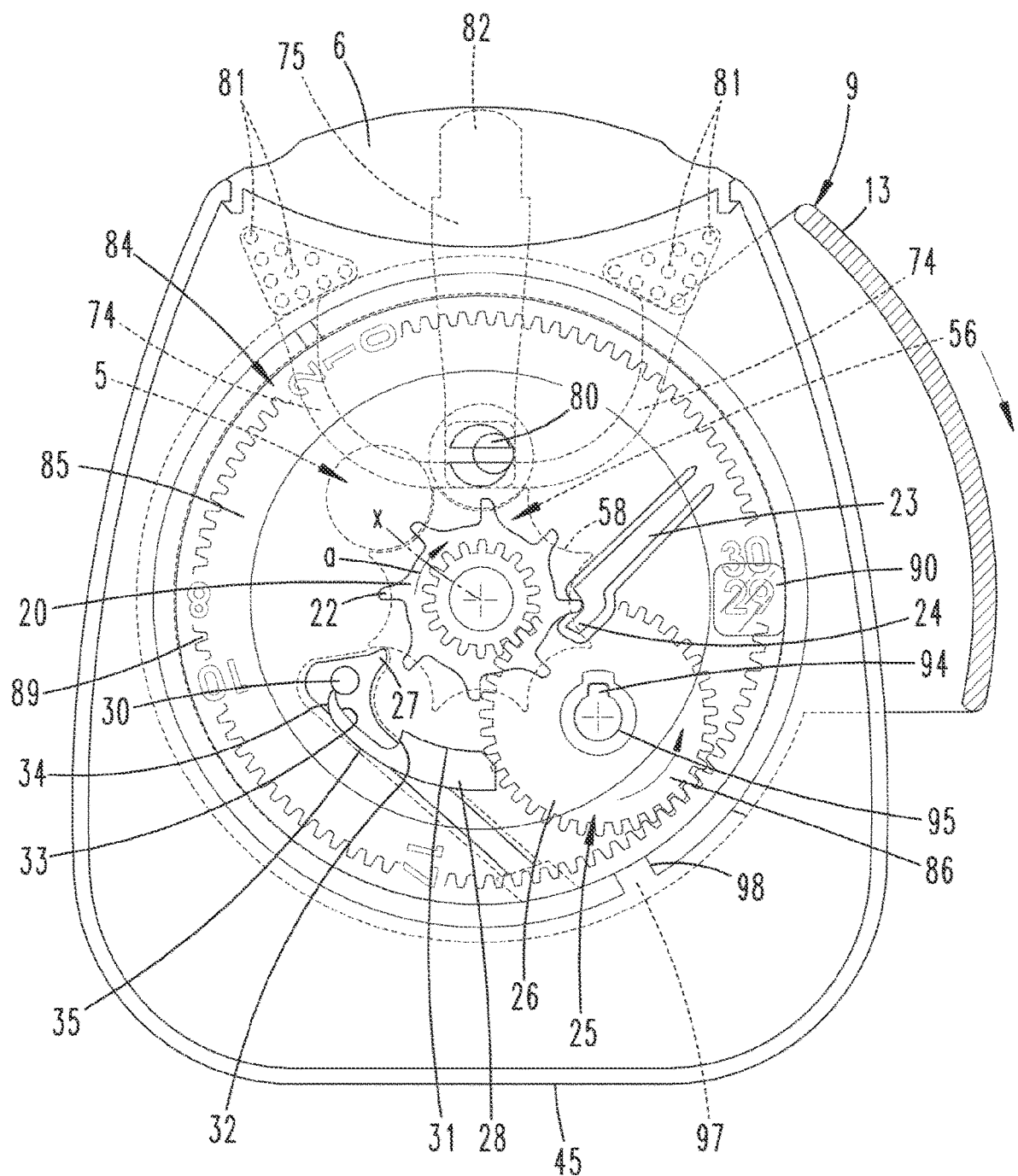
FIG. 46 shows a further follow-up illustration in the course of the pivoting of the closure cap into the open position, relating to the application situation of the insertion means.

Upon pivoting the closure cap 9 out of the closed position according to FIG. 42, the control journal 30 initially moves against the control surface 29, wherein the control journal 30, and via the latter the entrainment lug 27, is controlled radially to the inside in relation to the pivot axis x under further pivoting displacement of the closure cap 9, by building up a restoring force in the spring arm 26 (see FIG. 43).

The entrainment lug 27 moves into a gap circumferentially between two entrainment protrusions 22 of the actuating wheel 20.

The entrainment lug 27, which, in the course of the further pivoting displacement of the closure cap 9, is guided in the direction of the open position along a first contact surface 31 that runs concentrically to the pivot axis x, in contact with an entertainment protrusion 22, entrains the actuating wheel 20 in the direction of rotation a, via a predetermined angular range, which makes it possible to move a substance container 5 into an emptying position P.

The angle of rotation of the actuating wheel 20 effected via the drive part 25 is preferably smaller than the possible, stop-limited pivot angle of the closure cap 9.

The entrainment lug 27, which is entrained in the course of this further pivoting displacement of the closure cap 9 via the spring arm 26, falls via a step-like recess 32 in the slotted guide 28 onto a second contact surface 33, which is radially offset to the outside relative to the pivot axis x with respect to the first contact surface 31. This drop of the entrainment lug 27 is supported by the restoring force of the spring arm 26. The entrainment lug 27 leaves the interaction region with the entrainment protrusion 22 of the actuating wheel 20, so that the further pivoting displacement of the closure cap 9 does not effect a further rotational influence on the actuating wheel 20.

Figure 47:
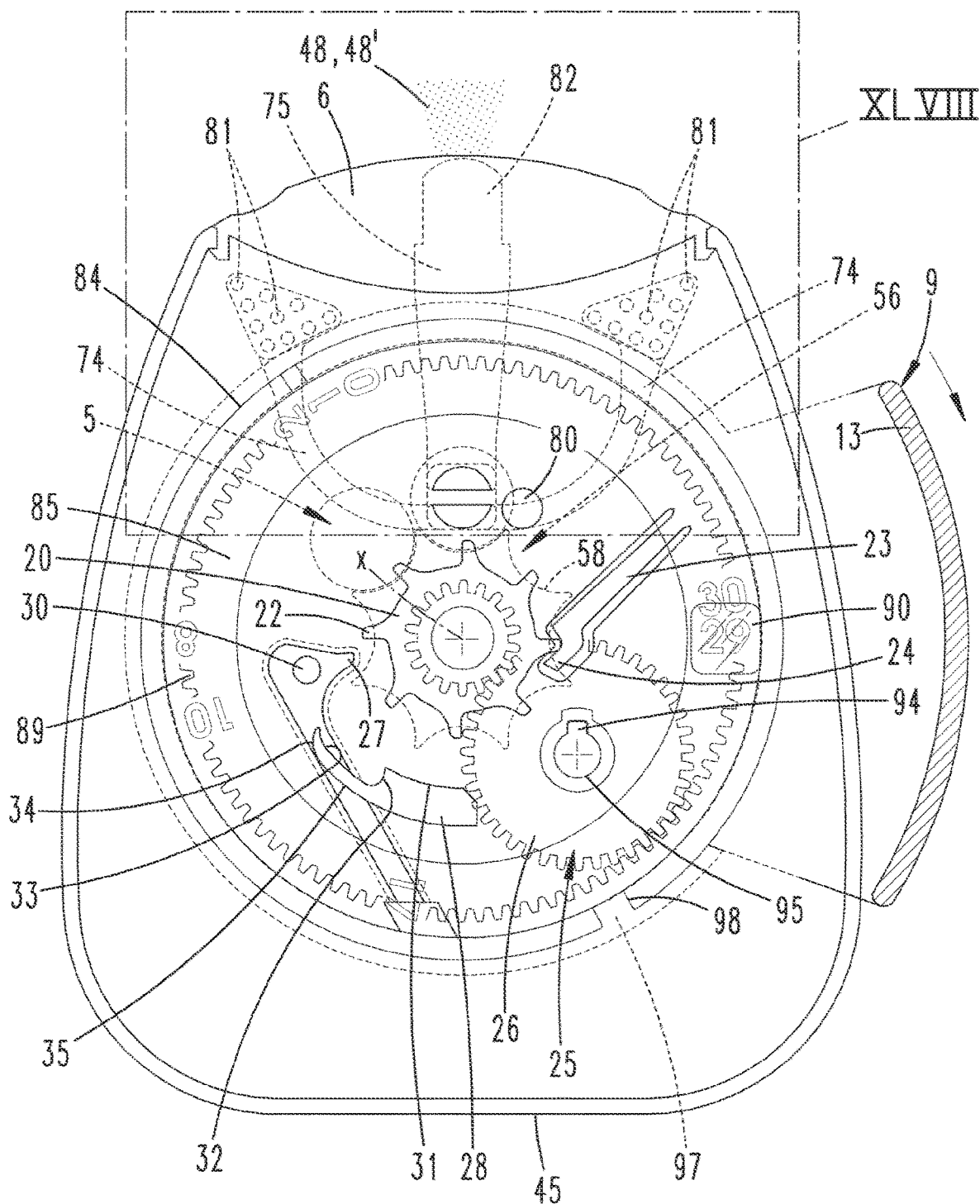
FIG. 47 shows a further follow-up illustration when reaching the closure cap open position.

Upon reaching the closure cap open position according to FIG. 47, the control journal 30 leaves the slotted guide 28, whereafter the drive part 25 can assume a position again, which is relaxed with respect to the spring forces.

The step-like design of the slotted guide 28 further effects that, after a complete rotational displacement of the actuating wheel 20 by the specified angle of rotation, and thus after displacement of a substance container 5 into the emptying position P, the further displacement of the closure cap 9 has to necessarily take place in the direction of the preferably stop-limited open position. A backward displacement of the closure cap 9 can only take place after the slotted guide 28 was left upon reaching the cap open position (according to the position in FIG. 47).

Out of this closure cap open position, the control journal 30 of the drive part 25 is moved—preferably after a previously performed inhalation process—as a result of displacement of the closure cap 9 in the direction of the basic position or in the direction of the mouthpiece closure position according to FIG. 42, respectively, against an end-side further control surface 34, which effects a rebounding displacement of the control journal 30 and thus of the entrainment lug 27 in relation to the pivot axis x radially to the outside, so that, in the course of the further pivoting displacement of the closure cap 9, the control journal 30 is moved in the direction of the mouthpiece closed position along a third contact surface 35, which is radially spaced apart to the outside with respect to the first and the second contact surface 31, 33, once again with respect to the pivot axis x. This results in a spring restoring force, which acts in the opposite direction with respect to the forward displacement of the drive part 25 in the region of the spring arm 26, until the control journal 30 leaves the slotted guide 28 just before reaching the closure cap end position, and assumes the position according to FIG. 42, which is not spring-loaded.

The guide mechanism 4 formed between or through the housing inner top and bottom parts 2, 3, respectively, forms a storage chamber 36 for a plurality of substance containers 5, which are not connected to one another. Housing inner top part 2 and housing inner bottom part 3 each form approximately half of the guide mechanism 4 or the storage chamber 36, respectively, viewed in the direction of extension of the pivot axis x. A U-shaped section can thereby result for each housing inner part in relation to a cross section, in which the pivot axis x presents itself as line, wherein the U-openings point towards one another, and the side walls 37, which limit these U-openings, bear against one another at the front surfaces.

A guideway 38 thus results, which is limited on the top and bottom side as well as laterally by means of the side walls 37 in relation to the pivot axis x, and in the case of which the side walls 37 are spaced apart from one another transversely to the longitudinal extension of the guideway 38, preferably adapted to an outer diameter d of the substance containers 5 to one another.

Figure 22:
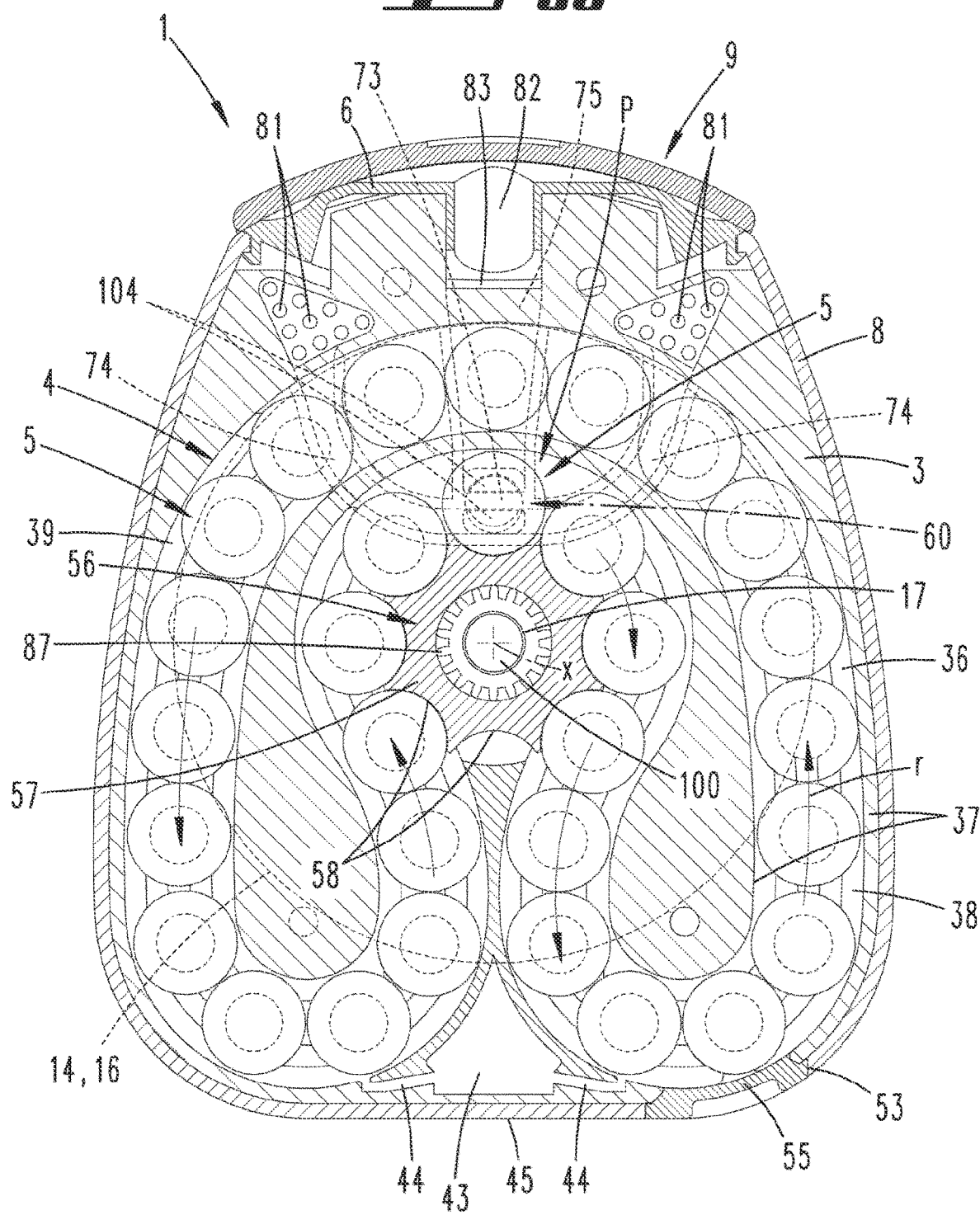
FIG. 22 shows the section according to the line XXII-XXII in FIG. 20.

As can be seen, for example from FIG. 22, the guideway 38 is provided in a meander-shaped manner in the manner of a continuous web in the device 1, thereby forming a loop, which runs concentrically to the pivot axis x, in the region of the pivot axis x.

Starting at this loop, the guideway 38 initially extends on both sides of the loop in the direction of a rear side of the device 1 facing away from the mouthpiece 6, in order to thereafter in each case extend back in the direction of the front region of the device 1 having the mouthpiece 6 over an arc, which is directed to the outside. An arc, which encompasses the loop and which optionally runs concentrically to the pivot axis x, connects the web sections to form a continuously curved continuous web, which preferably does not have any sections that run in a stretched-out straight manner.

Longitudinal grooves 41 can, and preferably, be provided over the entire or a majority of the guideway 38 in the region of the web base 39 and/or of the web ceiling 40. For example, two or three longitudinal grooves 41 can thus be provided in this regard, which extend in the longitudinal direction of extension of the guideway 38 and which are thereby spaced apart from one another transversely to the longitudinal extension.

These longitudinal grooves 41 can also be connected via transverse grooves 42 in some regions.

Figure 23:
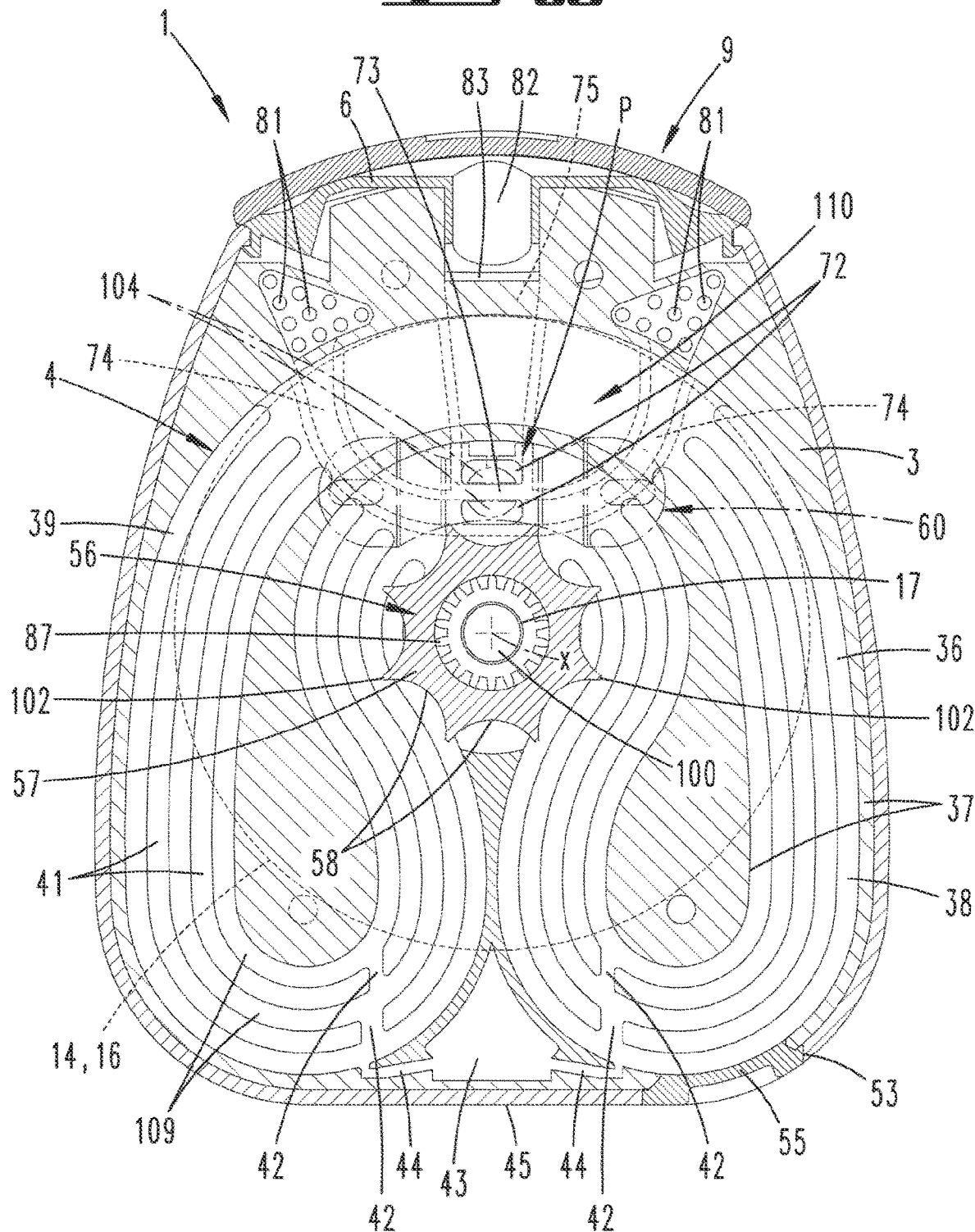
FIG. 23 shows an illustration corresponding to FIG. 22, but without substance containers, which can be accommodated in the device.

According to the illustration in FIG. 23, for example, longitudinal webs 109, which likewise extend in the longitudinal direction, can separate the longitudinal grooves 41 from one another in the longitudinal direction. In a zenith region 110 of the guide mechanism 4, which is assigned to the mouthpiece 6, the longitudinal webs 109 can be formed so as not to be continuous or so as to taper off beforehand, respectively. In this region, the longitudinal grooves 41 can therefore run freely into the web base 39 over the entire width, viewed transversely to the longitudinal extension of the longitudinal grooves 41. Distinctive longitudinal grooves are thus not present in this region.

Figure 23A:
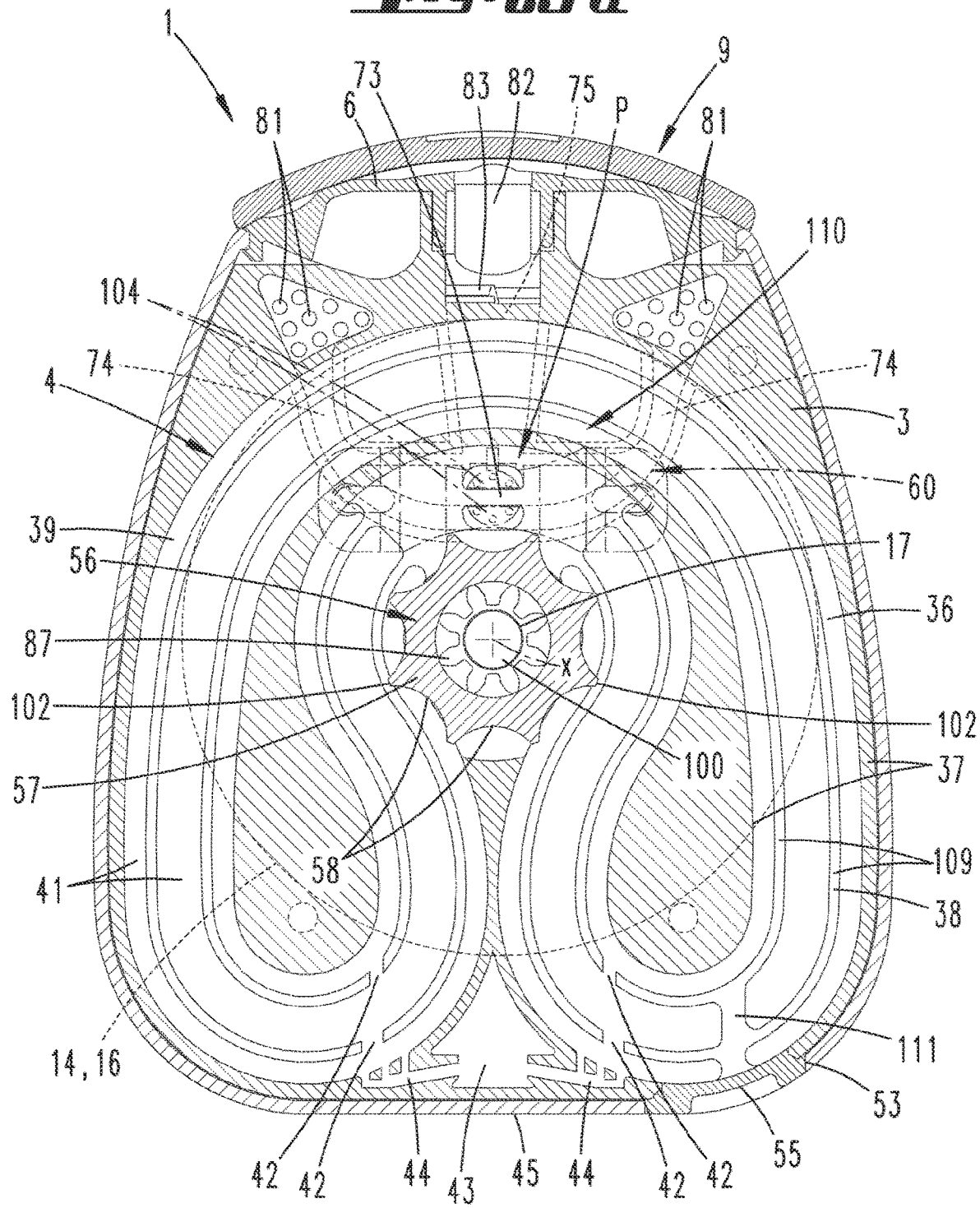
FIG. 23*a* shows an illustration corresponding to FIG. 23, but relating to an alternative embodiment.

In the case of the exemplary embodiment shown in FIG. 23a, in contrast, the zenith region 110 is also permeated with longitudinal webs 109 separating the longitudinal grooves 41.

According to FIG. 23a, the longitudinal webs 109 can also be connected to one another via a bridge section 111, preferably in the region of an insertion or housing opening 53, respectively, in the transverse direction to the longitudinal extension of the webs.

Substance 48, 48', in particular powder-type substance 48, 48', which optionally escapes from a substance container 5, can be guided via this groove structure in the base and/or ceiling region of the guideway 38 in a favorable manner into the intermediate spaces formed by the grooves, and optionally via said intermediate spaces into a collection chamber 43, which is further provided. This collection chamber 43 can result in a gusset region on the rear side in relation to the mouthpiece 6 between the turning regions of the guideway 38.

In this case, the collection chamber 43 is preferably connected via branches 44 to the sections of the guideway 38 facing one another.

The corresponding rear side of the device 1 can provide a floor space 45 for the device 1, so that the collection chamber 43 is arranged in a lowermost region of the device in this case, and the substance, which optionally accumulates in the grooves 41 and 42, reaches in the direction of the collection chamber 43 due to the force of gravity.

The substance container 5, which is in particular illustrated in FIGS. 4 to 10 as well as 41, can initially and essentially be formed in a circular cylindrical manner, having a cylinder axis y, which is aligned in the same direction to the geometric pivot axis y or the axis of rotation of the drive shaft 17, respectively, in the accommodating position of the substance container 5 in the device 1 or in the guide mechanism 4, respectively.

As illustrated, the outer diameter d can be selected to be larger than the height extension of the substance container 5 viewed in the axial direction. The diameter d can thus correspond approximately to 1.2-times to 1.5-times the axial height e (see FIG. 6).

Figure 41:
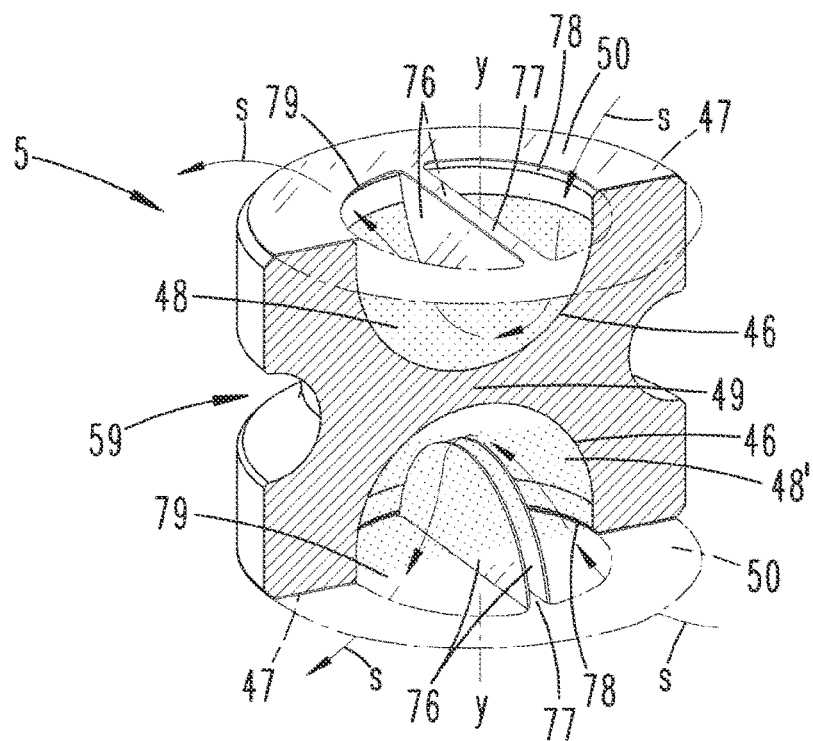
FIG. 41 shows a perspective sectional illustration through a substance container, in the case of covers, which are punctured by means of an insertion mechanism according to FIG. 36.

The substance container 5 is preferably also made of a hard plastic, for example polypropylene or polyethylene. It has two sub-regions 46 or cavities, respectively, which are located opposite one another in the direction of extension of the cylinder axis y and which are aligned concentrically to the cylinder axis y. As illustrated in FIG. 41, for example, they can essentially be formed approximately as hemispherical depressions. The respective opening results in the respective front surface, which is aligned transversely to the axis y. Each cavity can be designed to accommodate an amount of substance of, for example, 2 to 250 µg, further for example 10 to 100 µg.

Figure 41A:
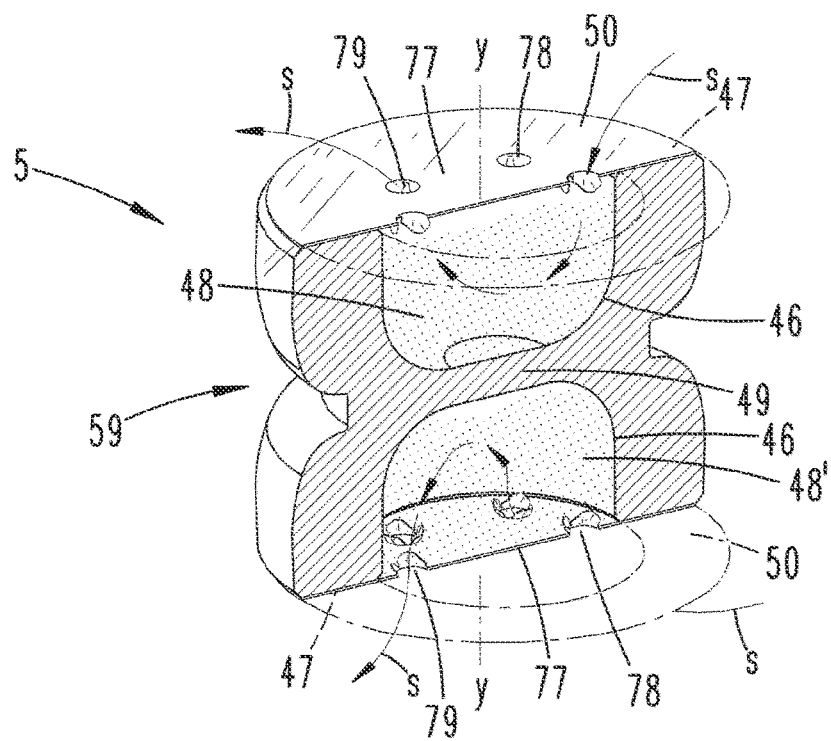

According to the illustrations in FIGS. 38a and 41a, a sub-region 46 of the substance container 5 can also be formed as essentially pot-like depression, comprising a cylindrical pot wall essentially relative to the cylinder axis y, and a pot base running transversely to the axis y. The transition from pot wall into the pot base is rounded. A favorable evacuation of the cavity can also be attained by means of this cross sectional geometry according to FIG. 41a. The pot base has a region, which extends in a planar manner transversely to the axis y or is formed so as to run in a curved manner with a radius, which is much larger compared to the transition from the pot wall into the pot base.

The sub-regions 46 are formed to accommodate a substance 48, 48' each.

Different substances 48, 48' can be accommodated in the sub-regions 46 by means of the separation of the sub-regions from one another by including a base 49, which is preferably positioned in the center in relation to the height e.

The cavities or sub-regions 46, respectively, are in each case covered with an openable or pierceable cover 50, respectively. These covers 50 seal the respective sub-region 46 and the substance 48, 48' accommodated therein.

The cover 50 can, and preferably, be a foil, for example an aluminum foil. This foil is preferably welded to the front edge 47 of the substance container 5.

For this purpose, the front edge 47 can furthermore have ribs 51, which protrude circumferentially in the axial direction and which, after placement of the foil-like cover in the course of the welding process, in particular ultrasonic welding process, melt and generate the adhesion of the cover 50 by equalization in the surface.

A plurality of such substance containers 5, which are preferably identical with respect to the setup and the dimensions, is accommodated in the guide mechanism 4, which is attached to the device. The respective accommodated substance in the substance containers 5, however, can be different, for example with respect to the composition and/or amount and/or dosage.

According to the illustrated exemplary embodiment, thirty such substance containers 5 can be accommodated in the continuous guideway 38, wherein the substance containers 5 come essentially in direct contact with one another, viewed in the longitudinal extension of the guideway 38. The substance containers 5 are thereby in each case guided laterally through the side walls 37 of the guide mechanism 4.

Figure 20:
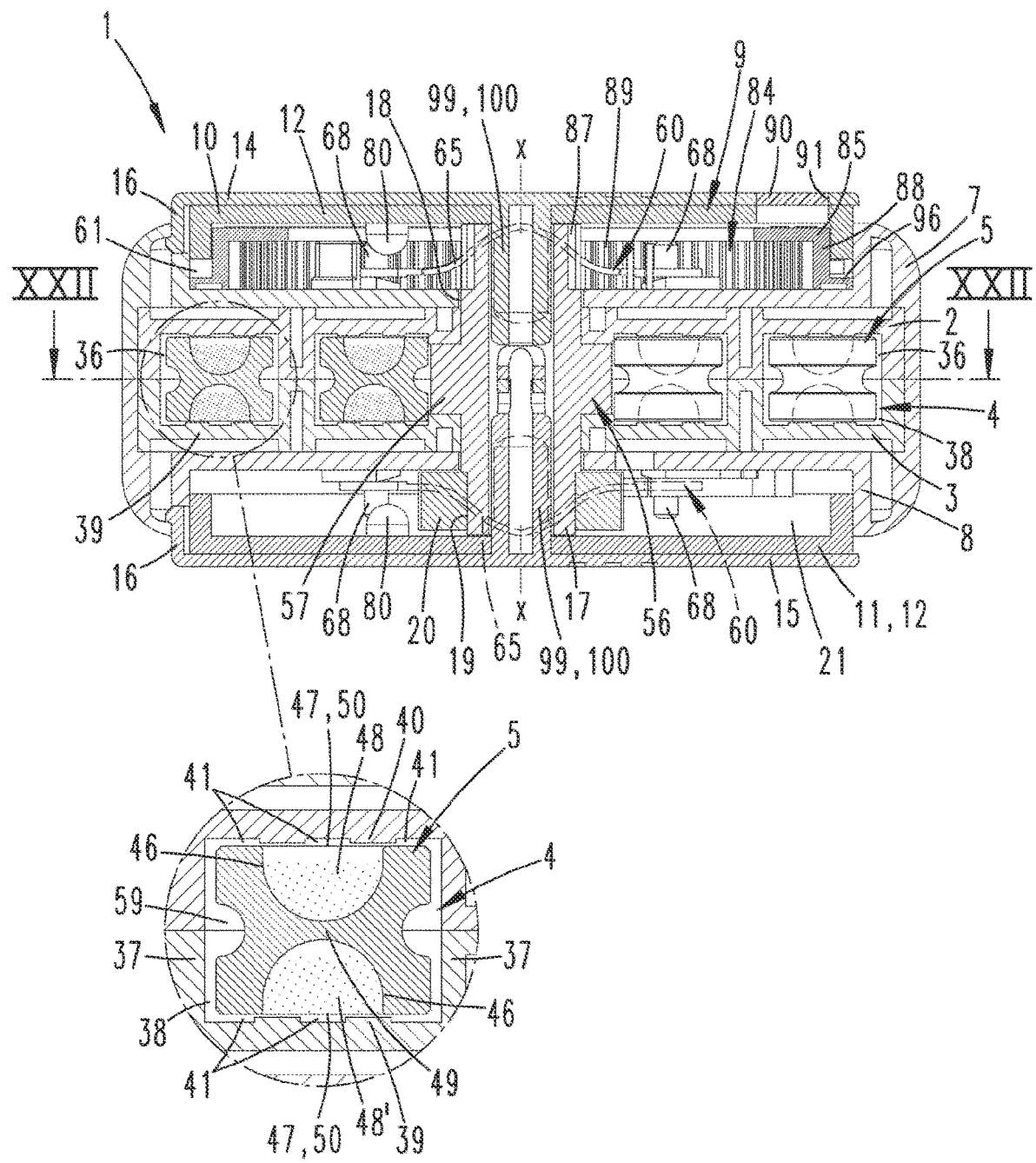
FIG. 20 shows the section according to the line XX-XX in FIG. 19.
Figure 21:
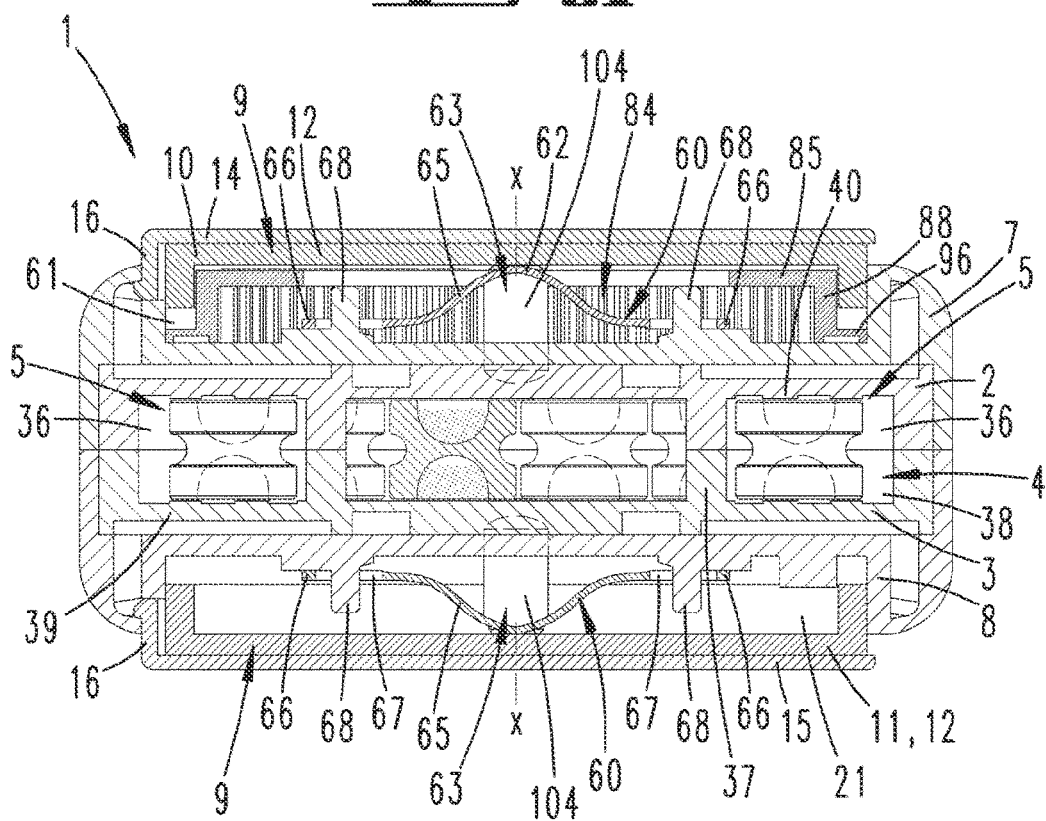
FIG. 21 shows the section according to the line XXI-XXI in FIG. 19.

Via their front edges 47, the substance containers 5 in each case experience a support on the bearing surfaces of web base 39 and web ceiling 40, which are raised with respect to the longitudinal and transverse grooves 41 and 42 (see FIG. 20, in particular the corresponding enlarged illustration).

Figure 24:
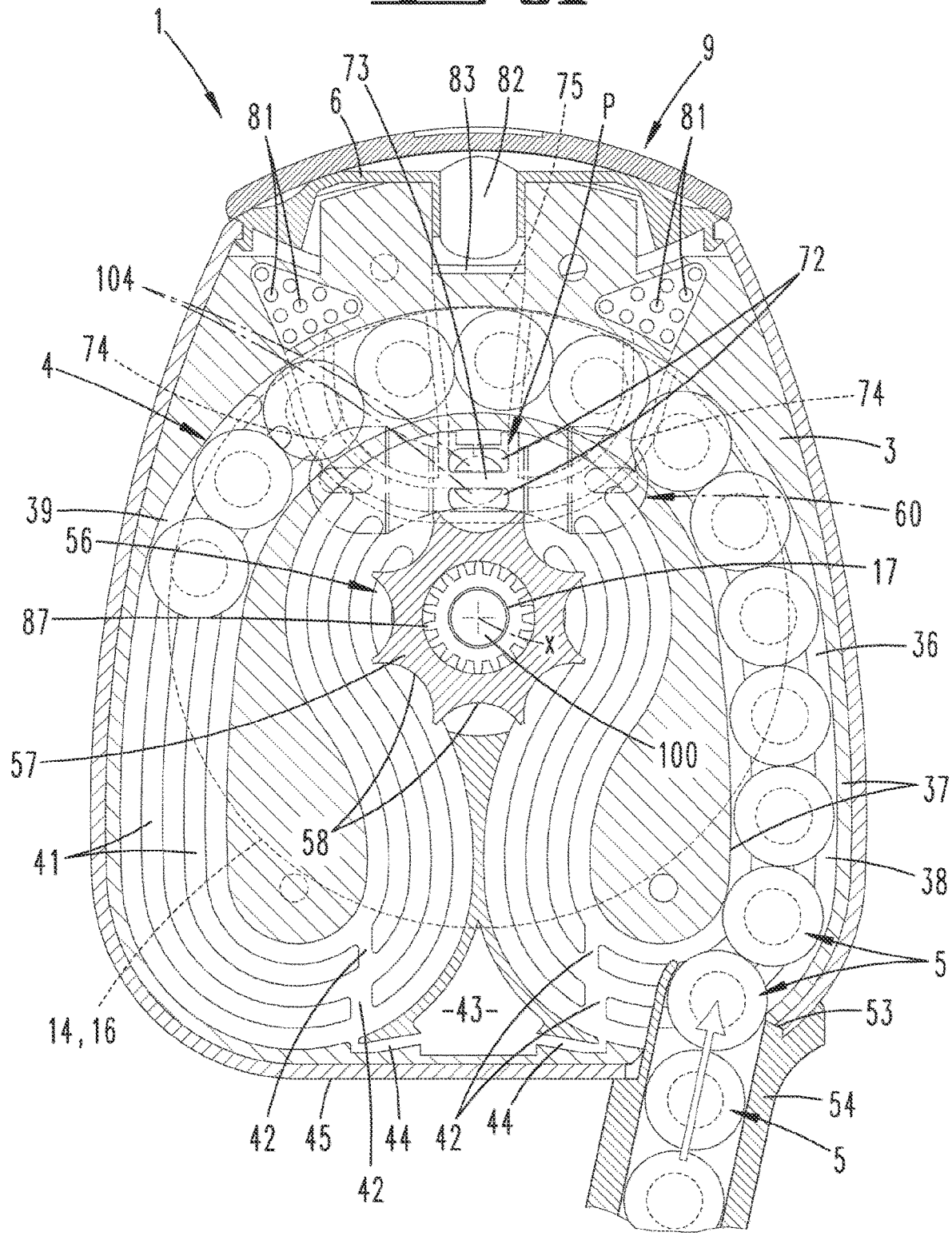
Figure 30:
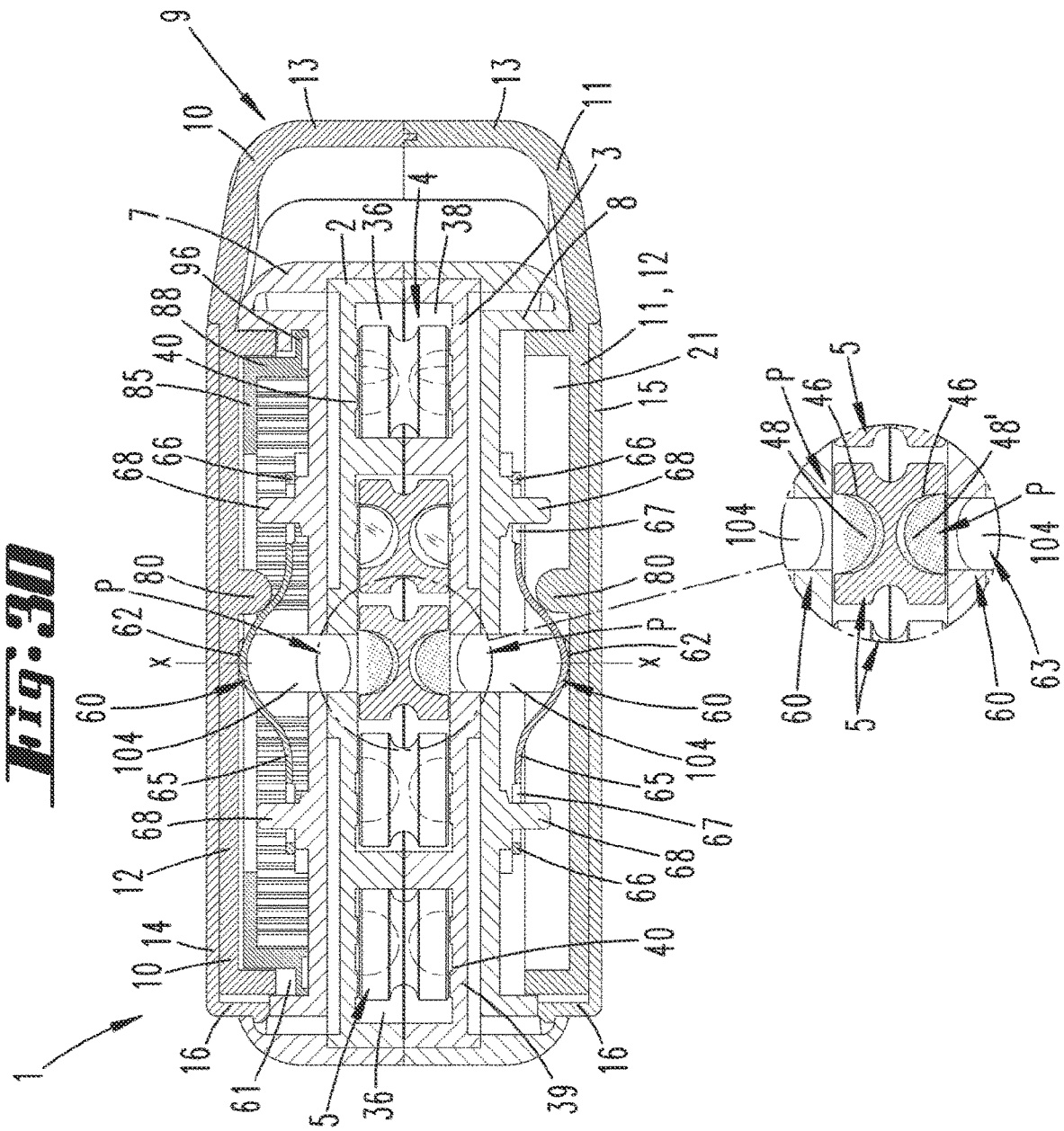
FIG. 30 shows the section according to the line XXX-XXX in FIG. 29.
Figure 31:
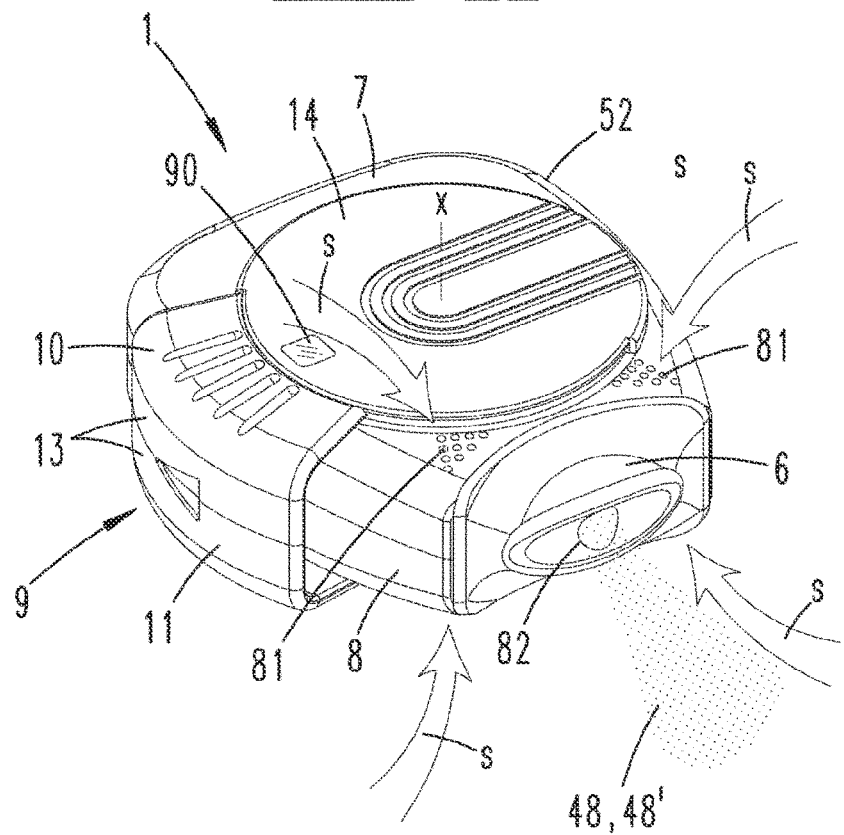
FIG. 31 shows the device in perspective illustration, relating to the closure cap open position and thus the inhalation-ready position.

As can be seen from the illustration in FIG. 24, the substance containers 5 can also be inserted into the guide mechanism 4 or into the guideway 38, respectively, only after essentially complete and operable assembly of the device 1. For this purpose, an insertion or housing opening 53, respectively, is provided at the housing 52 of the device 1, for instance assigned to the floor space 45 and thus more preferably assigned to a rearward turning section of the guideway 38.

An insertion aid, for example in the form of an insertion rail 54, can be attached to this opening 53, via which insertion aid the substance containers 5, which are accommodated in the rail so as to be arranged one behind the other, can be moved into the guideway 38 solely by means of the pressure propagating among the substance containers 5. The number of the substance containers 5 initially accommodated in the insertion rail 54 preferably corresponds to the number of substance containers 5, which can be maximally accommodated in the guideway 38 or the guide mechanism 4, respectively.

A continuous chain of substance containers 5, which is not connected to one another, in the guide mechanism 4 is closed by means of the last inserted substance container 5. The last inserted substance container 5 acts in the manner of a capstone in the continuous chain.

The run-in direction of the substance containers 5 in the course of the equipment of the device 1 by using, for example, such an insertion rail 54 corresponds to the displacement direction r of the substance containers 5 within the device 1 during conventional use of the device 1.

The insertion or housing opening 53, respectively, is final, that is, it is closed by means of a closure part 55 after complete equipment of the device 1 with the specified number of substance containers 5. The closure part 55 can be, for example, adhered or welded to the circumferential housing edge. A locking connection is optionally also possible in this regard. It is essential thereby that the closure part 55 can preferably no longer be removed without destruction after a corresponding closure.

In the closed position, the closure part 55 forms a part of the guideway 38 or of the side wall 37, respectively, on the wall inner side.

The substance containers 5 are moved in the guide mechanism 4 or the guideway 38, respectively, via a drive element 56 in the longitudinal direction of extension of the guideway 38 in such a way that an emptied substance container is displaced out of the emptying position P, and an immediately following substance container 5, which stores substance 48 and 48' in its sub-regions 46, moves up into this emptying position P.

In the illustrated exemplary embodiment, the emptying position P is reached in the zenith of the loop of the guideway 38, which engages around the pivot axis x.

The drive element 56 can, and as is illustrated, be a star wheel-like drive wheel 57, which can be driven in a rotationally fixed manner on the drive shaft 17 via the actuating wheel 20. Only one such drive element 56 or drive wheel 57, respectively, is preferably provided in the device 1.

The drive wheel 57 is provided with radially open accommodating moldings 58, which, viewed over the circumference, are limited on both sides by means of radially protruding drive teeth 102 and which are spaced apart from one another by means of the drive teeth 102. As illustrated in the exemplary embodiment, eight such accommodating moldings 58 can be provided so as to be distributed evenly over the circumference. They are preferably designed identically in the form of concave edge recesses, in particular edge recesses in the shape of the segment of a circle, the radius of which is preferably adapted to the outer diameter d of a substance container 5.

The drive element 56 seizes the substance containers 5 in the region of the guideway loop by means of the accommodating moldings 58. For example seven such substance containers 5 are seized thereby or are guided by means of the drive wheel 57, respectively, and are guided in the guideway 38 as a result of rotational displacement of the drive wheel 57. Due to the contact pressure propagating in the continuous chain among the substance containers 5, all substance containers 5 are thereby moved further in response to corresponding rotation of the drive wheel 57.

The angle of rotation of the drive wheel 57 for changing the substance containers 5 in the emptying position P is a function of the number of accommodation moldings 58, among others. A corresponding angle of rotation of preferably approximately 45 degrees results in the case of eight accommodation moldings 58.

As mentioned, the pivot angle of the closure cap 9, via which pivoting displacement the drive wheel 57 is also influenced via the drive shaft 17, is selected to be larger than the permitted angle of rotation of the drive wheel 57. Due to the above-described slotted guide 28, the drive part 25 becomes disengaged from the actuating wheel 20 after performing a 45 degrees rotation of the drive wheel 57.

It is thus ensured that a displacement of the substance container chain only by one container in the displacement direction r is performed with each opening movement of the closure cap 9.

As can further be seen in particular from the illustrations in FIGS. 6, 7, and 41, the substance container 5 can have an outer circumferential groove 59, which is aligned transversely to the cylinder axis y, approximately in the center, based on the cylinder axis y. With respect to a cross section, in which the cylinder axis y presents itself as line, this groove 59 can have a hemispherical contour, which opens to the outside (see FIG. 7 or 41).

In alternative design, the groove base of the groove 59, which is directed radially to the inside, can be formed as a circular cylindrical wall section, starting at which the groove walls extend radially to the outside, in each case along a curved line, in a cross section according to FIG. 41a in such a way that a funnel-like widening of the groove 59 all the way into the container wall results.

The radial depth of the groove 59 or a corresponding radius of the circumferential hemispherical depression, respectively, can preferably be selected in such a way that as a whole, approximately an equalization of the wall thickness of the substance container 5 results, further in particular with respect to the wall, which revolves concentrically to the cylinder axis y.

So-called incidence phenomena, as they can appear in the case of excessive wall thicknesses in the case of hard plastic products, is counteracted by means of the given tapering of the substance container 5. In addition, material savings and, via the latter, weight savings also results thereby.

The groove 59 can furthermore also be used for guiding the substance containers 5 in the device 1, in particular in the guide mechanism 4, for the purpose of which one or both side walls 37 of the guideway 38 can have, centrally in its height viewed in the direction of extension of the pivot axis x, a rib or the like pointing in the direction of the opposite side wall, which engages with the groove 59 of the substance container 5 in a guiding manner. Via this, the guidance of the substance containers 5 in the guide mechanism 4 can thus optionally take place solely via these ribs, which engage with the grooves 59. The front edges 47 of the substance containers 5 can thereby be spaced apart from the web base 39 and/or from the web ceiling 40.

Assigned to the emptying position P of a substance container 5, an insertion mechanism 60 is provided for the controlled systematic opening of the cover 50 on the substance container side.

According to the formation of two sub-regions 46 in the substance container 5, each having substances 48, 48', two insertion mechanisms 60 are preferably also provided. They are located opposite one another in the direction of extension of the pivot axis x.

One mechanism 60 can thereby be arranged in the depression 21 of the housing shell bottom part 8, and the further insertion mechanism 60 can be arranged in such a depression 61 in the housing shell top part 7.

An insertion mechanism 60 is illustrated in an exemplary manner in FIGS. 36 to 39.

Each insertion mechanism 60 initially has a retaining part 62, to which an insertion means 63 is fastened. Assigned to one insertion means 63, two separate insertion regions 104 are preferably provided, which can be designed, for example, in the shape of the segment of a circle in relation to a cross section according to the illustration in FIG. 39.

As can be seen, for example, from FIGS. 36a and 36b, each insertion region 104 can alternatively have two or more—here for example three—insertion tips 105. They can be arranged on the front side on pedestals 108 in the shape of the segment of a circle. The insertion tips 104 preferably protrude freely beyond a front surface of the pedestal 108.

In relation to a longitudinal extension L of an insertion mechanism 60 as a whole, the insertion regions 104 are spaced apart from one another transversely to this longitudinal extension L, wherein the flat sides of the segments of a circle face one another in the case of a formation of the insertion regions 104 in the shape of the segment of a circle. A slit-like free space 64 therefore results between the insertion regions 104, which preferably extends over the entire length of extension of the insertion regions 104, perpendicular to the longitudinal extension L, all the way to the retaining part 62.

The free end regions of the insertion regions 104 facing away from the retaining part 62 can be formed so as to be pointed in a blade-like manner, comprising a blade tip preferably in each case in the zenith region of the segments of a circular.

In case of formation of insertion tips 105, a mandrel-like formation is preferred, comprising a preferably cylindrical region 106, via which the insertion tip 105 is connected to the pedestal 108, and an adjacent tip region 107. Starting at the cylindrical region 106, the tip region 107 can be formed so as to taper conically towards the free end.

Each insertion mechanism 60 preferably has a separate retaining part 62, As illustrated in an exemplary manner in FIG. 40 on the basis of the dash-dotted line, however, both insertion mechanisms 60 can also have a common retaining part 62.

In addition, the retaining part 62 of an insertion mechanism 60 can, and preferably, be formed in combination with a plastic spring 65. This plastic spring 65 has two spring arms 66, which are directed oppositely in the longitudinal extension L. In the respective end region, the spring arms 66 thereby preferably extend approximately within a common bearing plane E, which is aligned transversely to the direction of extension of the insertion means 63, in relation to the longitudinal extension L. In a side view according to FIG. 37, in which an insertion direction b or c, respectively, presents itself in a line-shaped manner and both spring arms 66 are displayed in their longitudinal extension, the central connecting region of the spring arms 66, viewed in the longitudinal extension L, extends in a concavely curved manner, wherein the retaining part 62 is preferably arranged in the center of the longitudinal extension L between the spring arms 66. The insertion means 63 are preferably arranged on the underside of the arched ceiling, which is provided by means of the concave design in the region of the retaining part 62, and preferably permeate the above-described common bearing plane E of the two spring arms 66 (see FIG. 37).

Starting at their free ends, in each case in the regions, which provide the bearing plane E, the spring arms 66 can have elongated hole-like guide recesses 67, which can in each case interact with the journal 68, which is connected to the housing. A fixing of the insertion mechanism 60 to the respective housing part (housing shell top part 7 or housing shell bottom part 8) can be attained via these journals 68. In addition, a guidance of the retaining part 62 in response to an insertion process can simultaneously also be provided via this.

Such a guidance can also be provided by interaction between a housing-side guide appendage 69 and an edge-side guide notch 70 provided in the region of the retaining part 62.

An exact guidance in particular of the insertion regions 104 is in each case provided at least in the insertion direction b or c, respectively, of the respective insertion mechanism 60, so that the insertion direction b, c directed towards one another is preferably directed perpendicular to the bearing plane E over the entire displacement path.

In response to being acted on accordingly against the restoring force of the plastic spring 65, each insertion mechanism 60 is pushed in the direction of the pivot axis x through the respective cover 50 of the substance container 5 for opening the sub-regions 46. For this purpose, guide apertures 71, through which the insertion regions 104 can plunge, are provided in the respective depression base of the housing shell top part 7, which supports the insertion mechanism 60 and of the housing shell bottom part 8.

Corresponding apertures 72 are also formed in the housing inner top part 2 and the housing inner bottom part 3. They are initially provided in a bore-like manner, adapted to the outer diameter of the insertion means 63, thereby having a web 73, which separates the bore into two sub-sections centrally along a diameter line. With regard to its width viewed transversely to the diameter dimension, the web 73 is adapted to the corresponding clearance of the insertion regions 104 in the region of the slit-like guide 64 relative to one another. Such a web can also be provided in the housing shell parts in the region of the guide apertures 71.

The web 73 initially provides for a stabilization and guidance of the insertion regions 104, in particular in the course of the insertion process. In addition, the web 73 simultaneously provides for a separation between suction channels 74 and a discharge channel 75.

Suction channels 74 and a discharge channel 75 are in each case assigned separately to each cavity or each sub-region 46, respectively, of the sustenance container 5, which is in the emptying position P, via the respective webs 73.

As a result of the above-described arrangement and design of the insertion mechanism 60, the insertion means 63 or the insertion regions 104, respectively, preferably act in opposite insertion directions b and c, each directed along the pivot axis x. In response to corresponding stress for breaking through the covers 50, the insertion means 63 preferably act in directions that point towards one another.

Due to the insertion regions 104, two punching sections 76 in the shape of the segment of a circle can result in each cover 50 of the substance container 5, which is in the emptying position P, in the case of a formation of the insertion regions 104, for example according to the illustration in FIG. 36 or 39, which punching sections fold in inwards into the respective sub-region 46, preferably centrally along a diameter line of the substance container 5 or of the cover 50, respectively, over a remaining cover web 77 (see in particular FIG. 41).

As illustrated on the basis of FIGS. 38a and 41a, the insertion tips 105 of the insertion mechanism 60 according to FIG. 36a, for example, effect a hole-like punching of the container-side cover 50. The punched holes (openings 78 and 79), which thus result, can in each case have a diameter dimension, which can be selected to be smaller than, for example, 2 mm, more preferably smaller than 1.5 mm, thus optionally up to 0.5 mm or less. Pin-sized openings 78 and 79 preferably result.

A non-permeated or non-punched, central over web 77, respectively, also results here between two groups of punched holes, which groups consist of openings 78 on the one hand, and of openings 79 on the other hand.

Further assigned to each sub-region 46, an opening 78 for entrance of the air flow s from the suction channels 74, and an opening 79 for escape of the air flow s, which is mixed with substance 48 or 48', respectively, from the sub-region 46, can result thereby.

The web, which separates the suction channels 74 to the discharge channel 75, in the aperture 72 preferably bears on the cover 50 or the cover web 77, respectively, which results after opening the cover 50, so as to form a seal, so that a positive guidance of the air flow s through the opening 78 and through the sub-region 46 is provided.

The molding of the sub-region 46 as optionally hemispherical depression supports the evacuating effect via the air flow s. No dead zones appear in terms flow. Due to the punching sections 76, which fold in in the direction of the sub-region base, the air flow s is guided through the sub-region 46 close to the base, which supports the complete evacuation of the sub-region 46.

Both insertion mechanisms 60 are preferably stressed and relieved simultaneously. An optional stressing of the one or of both insertion mechanisms 60 can also be carried out in this respect.

An embodiment, in the case of which the movement of both insertion mechanisms 60 takes place synchronously as a result of pivoting displacement of the closure cap 9, is illustrated in the graphic illustrations.

For this purpose, a cam 80 can be molded on the bottom side of the closure cap top part 10 and of the closure cap bottom part 11, in each case directed in the direction of the respective facing depression 21 or 61, respectively, which cam push down the insertion means 63 against the restoring force of the plastic spring 65 in the insertion direction b and c in the course of the pivoting movement of the closure caps 9, preferably downstream from a forward displacement of the substance container 5 into the emptying position P.

The above-described forward motion of the substance container 5 to reach the emptying position P is already reached, for example, with a pivoting displacement of the closure cap 9 by approximately 45 degrees. By eliminating the entrainment movement between closure cap 9 and actuating wheel 20, the closure cap 9 can then pivot freely further in the direction of the complete open position, wherein the cams 80 run over the retaining parts 62 of the insertion mechanisms 60, by acting on them, in the course of the this pivoting movement. As a result of the forward motion of the substance container 5, it is ensured thereby that a new, non-evacuated substance container 5 is present in the above-described emptying position P. A systematic puncturing of the covers 50 takes place only thereafter.

At the end of the pivoting movement of the closure cap 9, the cams 80 leave the influence region on the insertion mechanisms 60, which move back into their initial position again as a result of the restoring force of the plastic springs 65. The insertion means 63 or insertion regions 104, respectively, thereby move out of the sub-regions 46 of the substance container 5 again, for correspondingly releasing the openings 78 and 79 or for connecting these openings to the suction and discharge channels 74, 75 in terms of flow, respectively.

Figure 32:
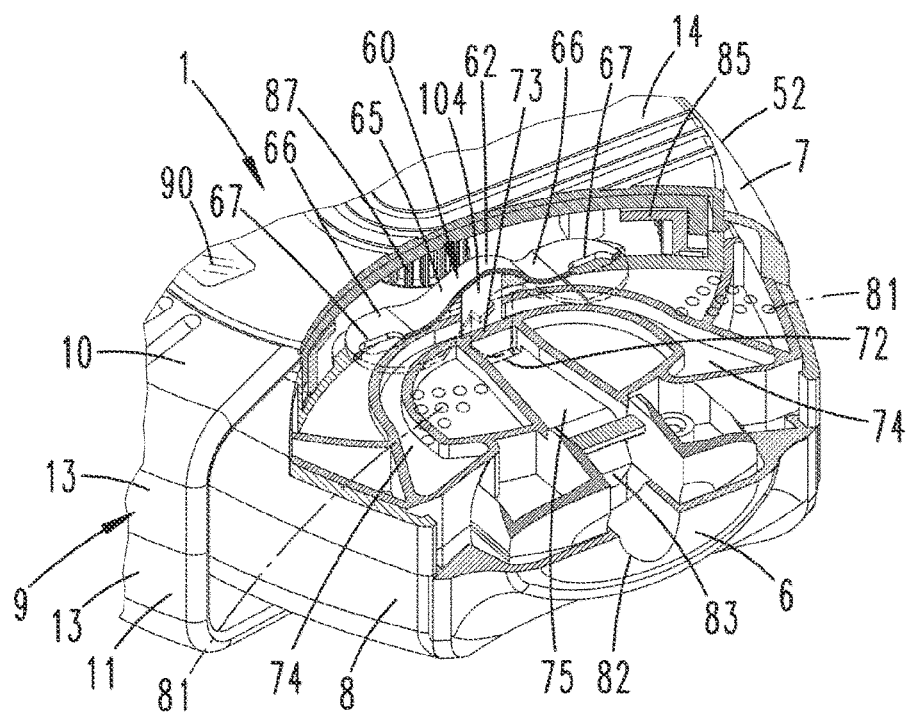
FIG. 32 shows an illustration essentially corresponding to FIG. 31, but partially broken open.

Two suction channels 74 are assigned to each sub-region 46 of the substance container 5, which is in the emptying position. The suction openings 81 thereof are formed on both sides of the mouthpiece 6 in the respective housing shell top part 7 or the housing shell bottom part 8, respectively, while the suction channels 74 can extend essentially in the housing inner top part 2 or the housing inner bottom part 3, respectively, in a molding manner (see, for example FIGS. 32 and 48).

A total of four suction channels 74 comprising four suction openings 81 thus result in the device 1, which suction openings 81 are positioned on both sides next to the mouthpiece 6 in such a way that they are exposed only after the closure cap 9 pivots upwards in the direction of the open position. In the closed basic position of the device 1, the suction openings 81 lie concealed under the closure cap 9 so as to be protected.

Figure 48:
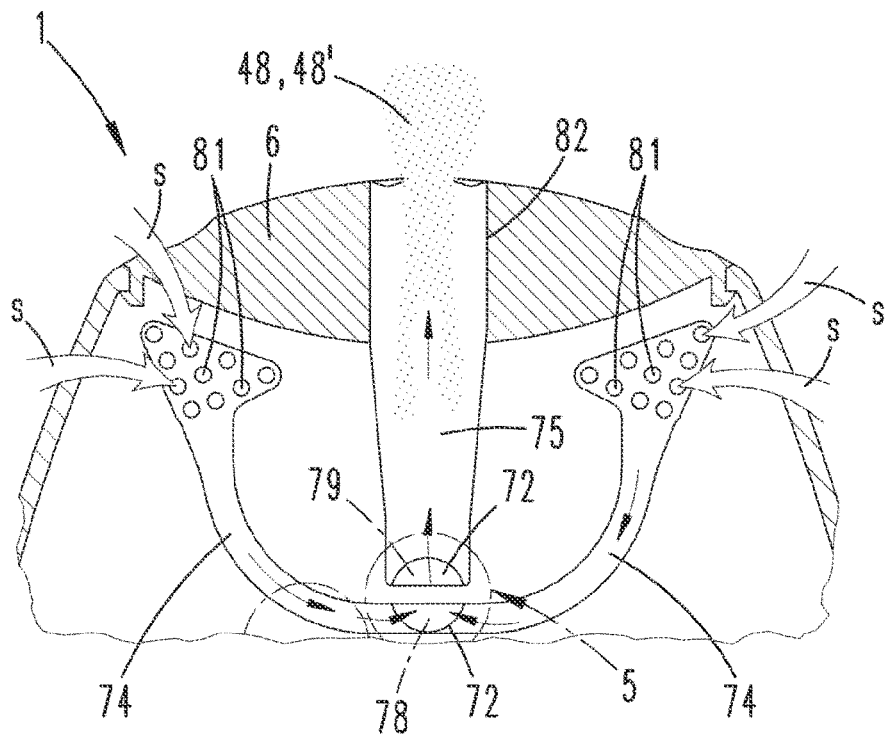
FIG. 48 shows the region of the air channels according to XLVIII in FIG. 47 in schematic illustration.

The two suction channels 74 of a cavity preferably meet directly in the region of the aperture 72, which is separated by means of the web 73 (see also FIG. 48).

Figure 48A:
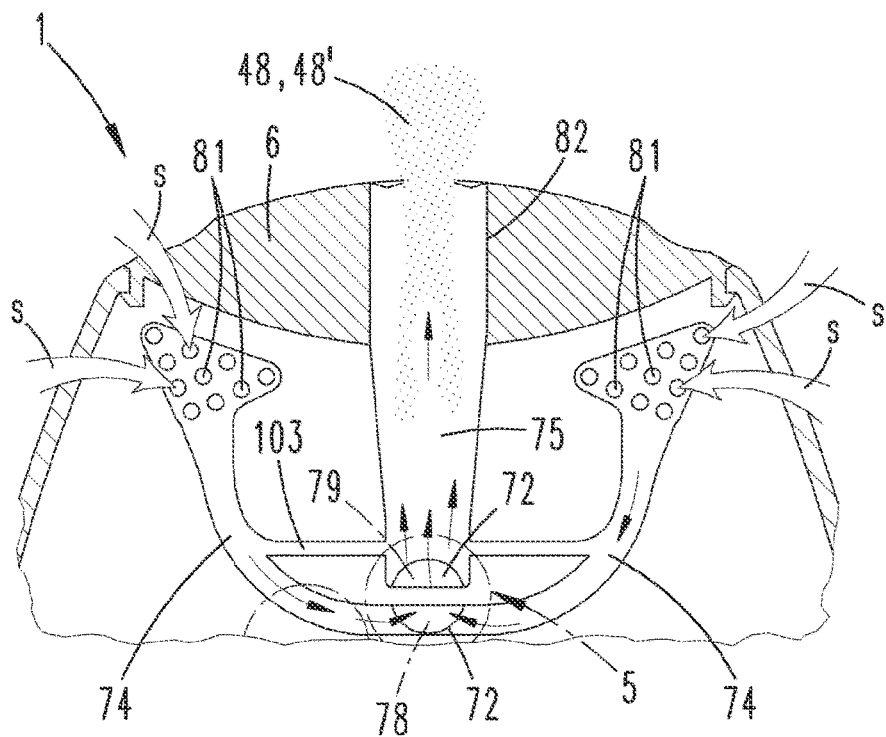

In alternative design, in particular and preferably in connection with the use of an insertion mechanism 60 comprising insertion tips 105 according to FIGS. 36a, 36b, and 39a, a bypass 103 can be provided, which connects the suction channels 74 in the air flow direction s upstream of the substance container 5 or upstream of the emptying position P, respectively (see FIGS. 32a and 48a). A portion of the drawn-in air can flow through this transverse channel (bypass 103) directly and without permeating the cavities of the substance container 5 into the discharge channel 75 in the course of an inhalation process. Such a bypass 103 can, and preferably, be assigned to each pair of the suction channels 74.

A discharge channel 75 is further assigned to each cavity or to each sub-region 46, respectively, of a substance container 5, which is in the emptying position. A total of two discharge channels 75 therefore result in the device 1, which, initially starting at the assigned aperture opening, are guided separately from one another in the direction of the mouthpiece 6, in particular in a direction approximately perpendicular to the above-described rearward floor space 45.

The two discharge channels 75 are merged directly in the transition to the mouthpiece channel 82 (see, for example, FIG. 33). A swirling element or the like can optionally be provided in this merging region 83.

According to the above-described design and separation of the discharge channels 75, the substances 48 and 48' are evacuated separately from the respective sub-regions 46 and are merged only immediately before passing into the breathing region of the user, in particular in the merging region 83 in the root region of the mouthpiece 6, and are mixed or swirled, respectively, in the course of an inhalation process after opening the covers 50 by means of the insertion mechanisms 60 and build-up of an air flow s as a result of aspiration or breathing in, respectively, via the mouthpiece 6.

The device 1 is further designed and formed to count the performed or still remaining emptying processes or inhalation processes, respectively. A counter 84 is provided for this purpose.

Figure 17:
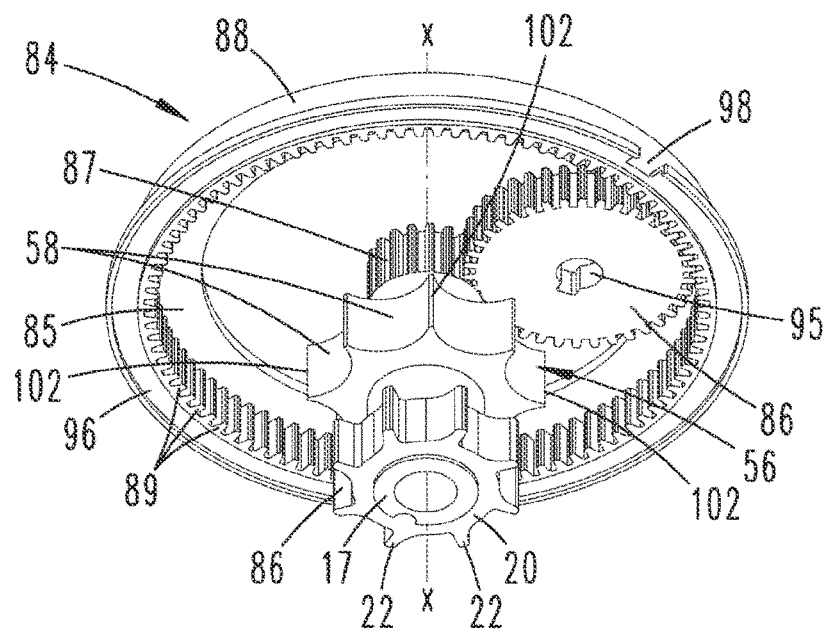
FIG. 17 shows the arrangement of a drive pinion, of a drive element, and of an actuating wheel arranged in a rotationally fixed manner on a drive shaft, further of a transfer gear and of a counting wheel, in perspective illustration.
Figure 18:
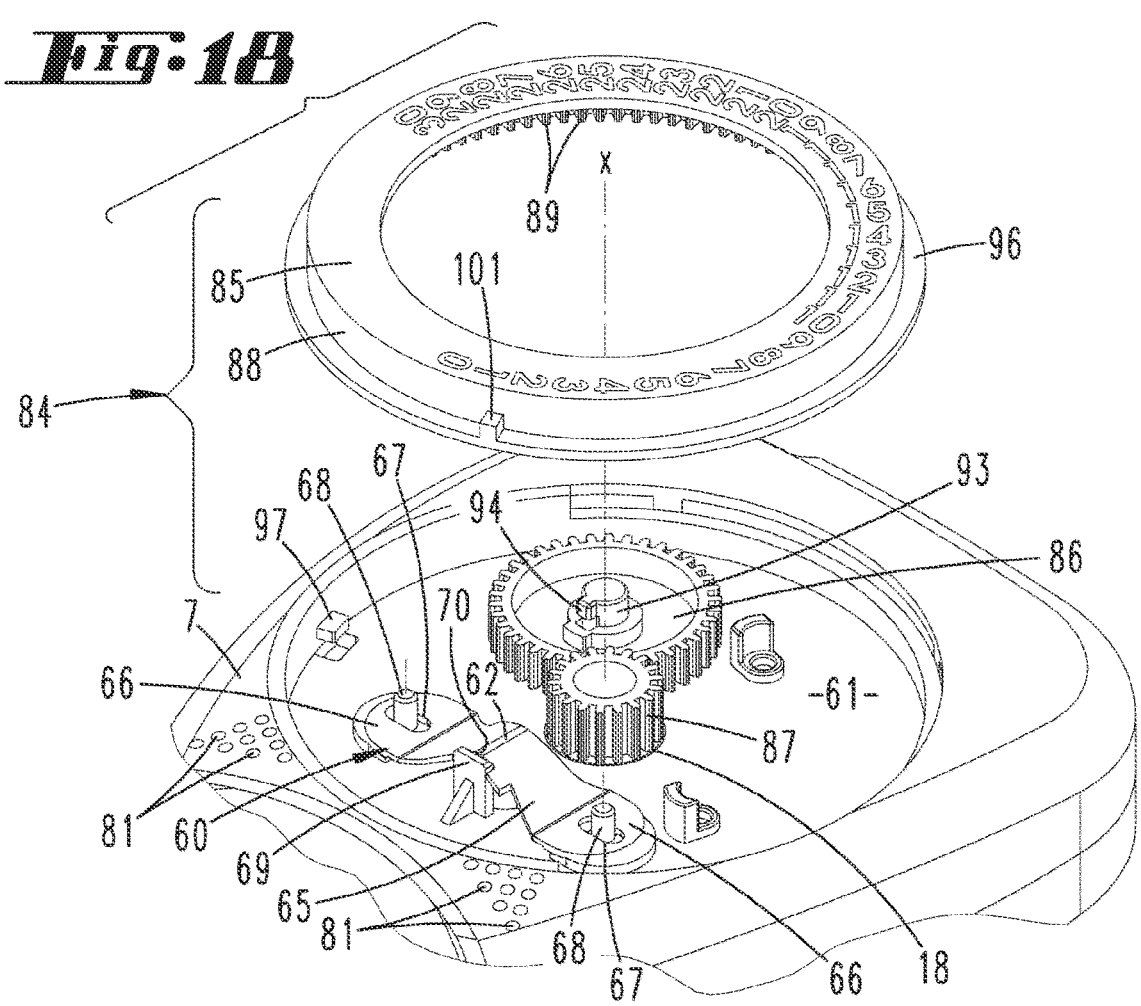
FIG. 18 shows the counting wheel and the transfer gear as well as the housing section accommodating the counting wheel and the transfer gear, in perspective exploded illustration.
Figure 19:
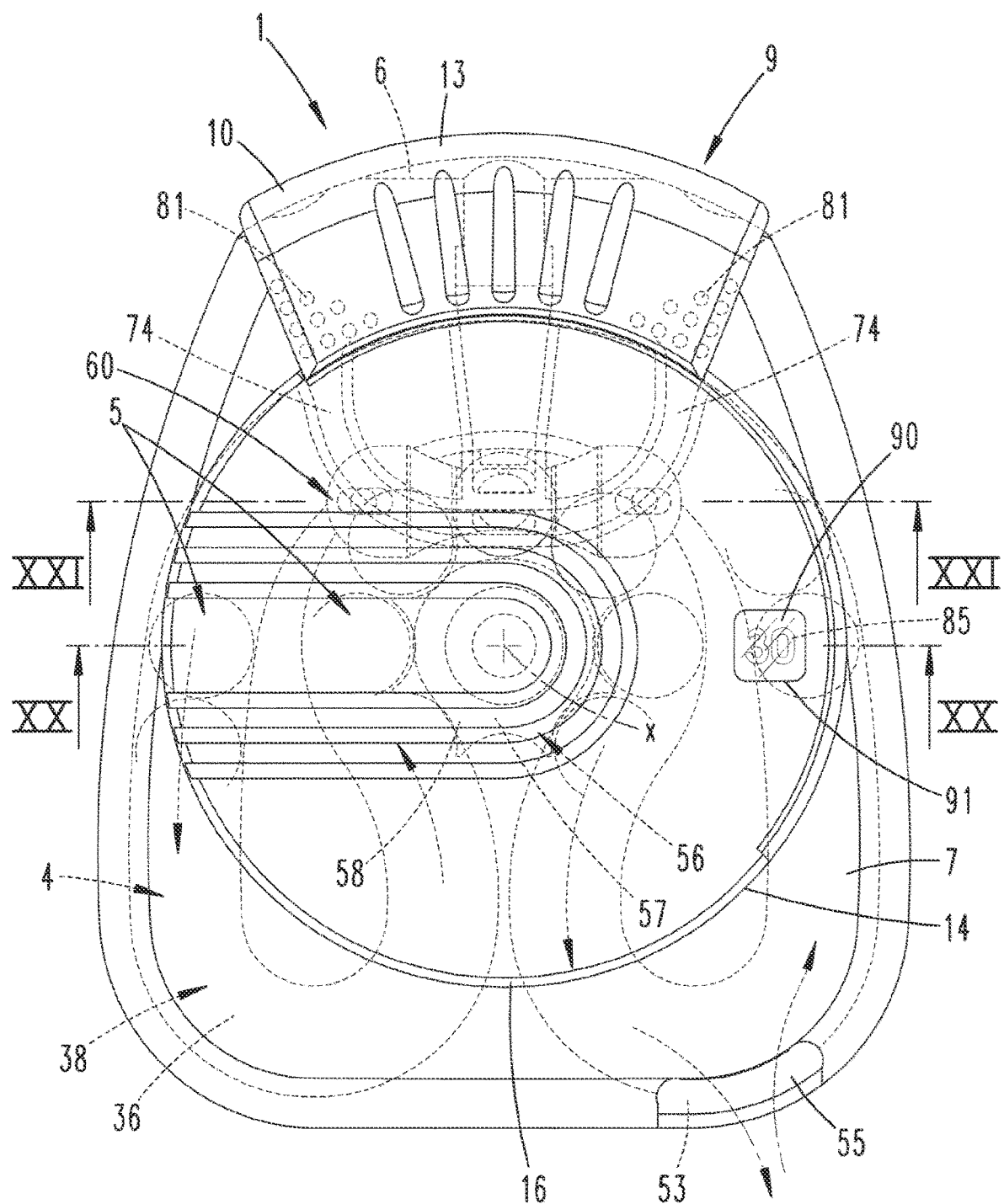
FIG. 19 shows the device in top view, relating to the closed non-use position.

The counter 84 essentially has a ring-shaped counting wheel 85, a transfer gear 86, and a drive pinion 87, as can be seen, for example from the detailed illustration in FIG. 17. The drive pinion 87 is arranged in a rotationally fixed manner on the drive shaft 17, and meshes with an external toothing of the transfer gear 86. The external toothing of the transfer gear 86, in turn, meshes with an internal toothing 89, which is formed on the inner side of a circumferential collar 88 of the counting wheel 85.

The gear-like counter 84 formed in this way is essentially arranged between the housing shell top part 7 and the assigned closure cap top part 10.

Symbols, in particular numerals, are applied in the region of a top-side, ring-shaped surface of the counting wheel 85. The number of the numerals preferably corresponds to the number of the substance containers 5, which can be accommodated in the guide mechanism 4 of the device 1. According to the illustrated exemplary embodiment, a numerical sequence of 0 to 30 can thus be provided.

The current rotational orientation of the counting wheel 85 and therefore the current number, which is to be displayed, of unused substance containers 5, which are still present, for example, or, in the alternative, of already used-up substance containers 5, is visible from the outside to the user via a transparent window 90 in the cover part 16. The window 90 closes an adapted aperture 91 in the cover part 16. The closure cap top part 10 also has such an aperture 92, which, in the mouthpiece closed position of the closure cap 9 in relation to the pivot axis x, is located one on top of the other so as to be aligned to the aperture 91 and the window 90 in the cover part 14. In addition, a further aperture 92' can be provided, which is formed in an offset manner in the circumferential direction and through which the display can also be recognized in the closure cap open position.

In the course of the closure cap pivoting movement, the numerals of the counting wheel 85 are no longer visible via the window 90, because the otherwise closed cover section 12 of the closure cap top part 10 moves between counting wheel 85 and window 90. Upon completed pivoting-back movement of the closure cap 9 into the closed position of the mouthpiece 6, the number, which is visible, compared to before the introduction of a pivoting of the closure cap 9 from the closed position into the open position, is increased by 1 or, in the alternative, is reduced by 1.

The closure cap pivoting movement therefore effects a displacement of the substance containers 5 within the guide mechanism 4 by one position, in order to move the next substance container 5 into the emptying position P in this way, as well as the opening of the covers 50 of both sub-regions 46 of the substance container 5, which is in the emptying position P, and additionally a change of the display of the counter 84.

The transfer gear 86 of the counter 84 is guided on an axle journal 93 of the housing shell top part 7. A geometric axis of rotation of the transfer gear 86 thereby extends in the same direction as the pivot axis x.

On the end side, therefore spaced apart from the depression base, in which the axle pin 93 is rooted, the axle journal 93 has a radial protrusion 94. The transfer gear 86 has a correspondingly adapted, key hole-like central aperture, which allows pushing the transfer gear 86 onto the axle journal 93 only in one rotational orientation. In the operating position, the hub of the transfer gear 86 circumvents the radial protrusion 94 of the axle journal 93, so that the transfer gear 86 can be rotated freely.

Along its circumferential collar 88, the counting wheel 85 has a radial collar 86 pointing to the outside. In the operating position, this radial collar 86 is covered by a web, which protrudes radially inwards, in the region of a housing wall encompassing the depression 61, and which forms a further alignment molding 97. A recess 98, which is open on the edge, is provided in the region of the radial collar 96 of the counting wheel 85.

As a result of the above-described designs, the counting wheel 85 as well as the transfer gear 86 can be assembled only in a specified angular alignment relative to one another and/or relative to the drive pinion 87.

The installation position in particular of the counting wheel 85 can thereby be such that only after inserting the substance containers 5 into the otherwise operational device 1, the counting wheel 85 is aligned in such a way that for example the maximal number of inhalation, which can then still be performed, or unused substance containers, respectively, can be recognized through the window 90, for instance the numeral 30 according to the shown exemplary embodiment. By means of the substance containers 5, which are inserted successively into the guide mechanism 4, for example via the insertion rail 54, the counting wheel 85, which is inserted in a specified rotational position, is entrained via the above-described gear arrangement and is moved into the exact initial position.

After opening the cavities of the last substance container 5 in the continuous row—and preferably an inhalation performed thereafter—the device 1 can be blocked in order to prepare a presumed next inhalation.

In this position, the counter 84 can thus, and preferably, display zero. The counting wheel 85 rotated accordingly into this position can thereby move against a section, which is attached to the device, for example against the alignment molding 97, in a blocking manner with a stop rib 101, which is molded in the region of the radial collar 96.

A blocking of the gear-like counter 84 and, via the latter, of the drive shaft 17, can be attained thereby, so that when an attempt is made to pivot open the closure cap 9 out of the closed position in the direction of the open position, the drive part 25 moves against the blocked drive shaft 17 or the actuating wheel 20, respectively, which is connected thereto in a rotationally fixed manner.

After emptying all substance containers 5, the device 1 is blocked and can preferably not be used further. By means of the preferred continuous stringing-together of the substance containers 5 in the guide mechanism 4, the first, already emptied substance container would be move into the emptying position P again without such a blocking after the last substance container 5. Such an incorrect operation is counteracted by means of the above-described blocking.

Figure 50:
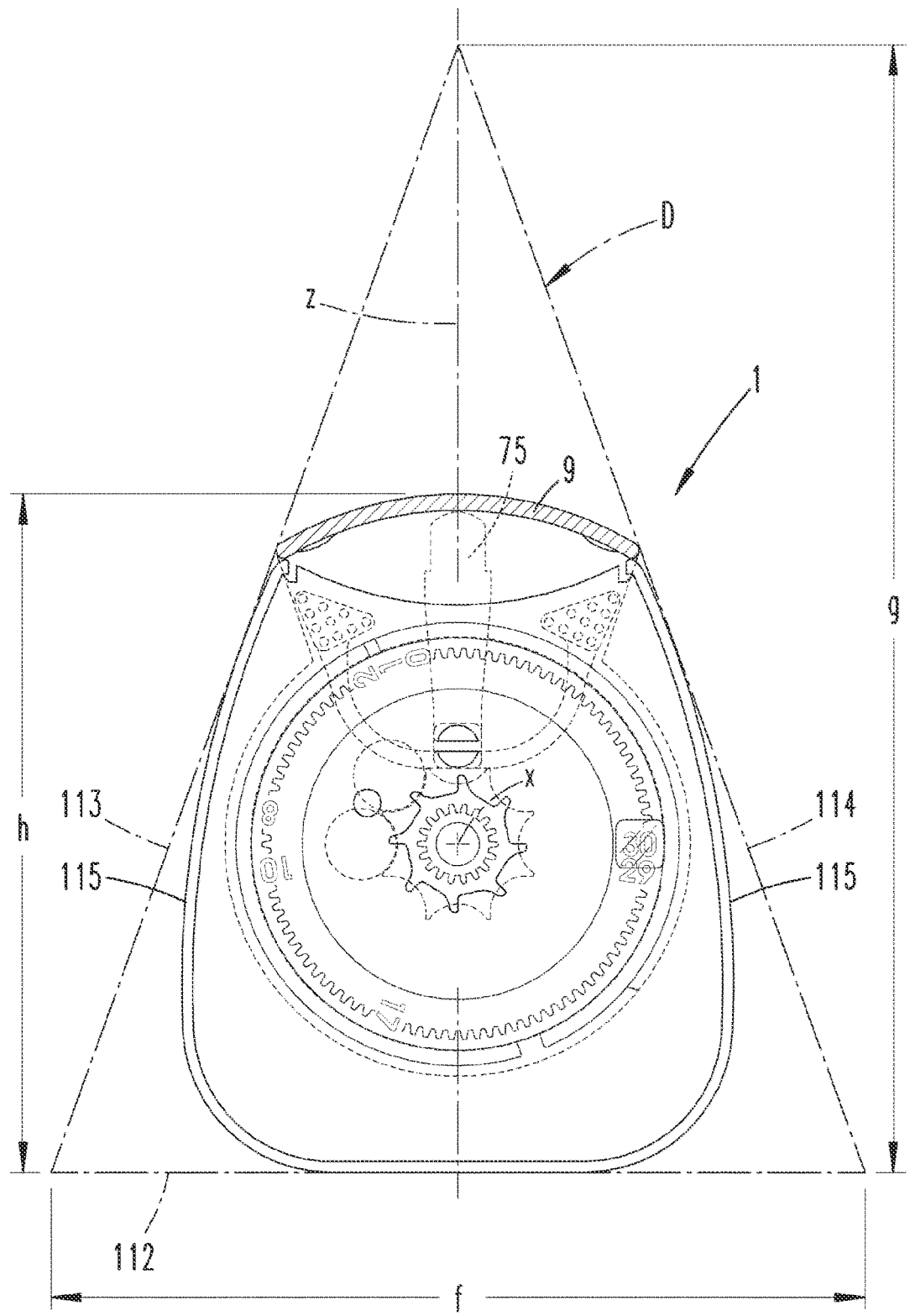
FIG. 50 shows a schematic illustration of the device in top view, for explanation of a geometric basic contour of the device and the dimensions thereof.

As can further also be seen, for example, from the schematic illustration in FIG. 50, the outer layout shape of the device, in which layout the pivot axis x presents itself as point, can essentially result of an acute-angled, isosceles triangle D, having a base line 112 with a base width f and an axis of symmetry z, which accommodates the pivot axis x of the device 1 and permeates the discharge channel 75 in the longitudinal alignment thereof in the center.

The height g of the triangle D along the axis of symmetry z can correspond to approximately 1.2- to 3-times or more, further for example approximately 1.5- to 2-times the base width f.

The base line 112 of the triangle D is thereby preferably tangent to the layout line of the device 1, which is given by the floor space 45, while the legs 113 and 114 of the triangle D tangentially touch the side wall sections 115 of the housing shell top part 7 and of the housing shell bottom part 8, which connect the floor space region to the mouthpiece region.

The height h of the device 1, starting at the floor space 45 and lying inside the triangle D, viewed along the axis of symmetry z to the closure cap 9, can corresponds to approximately 0.7- to 1.3-times or more, further for example to 0.8- to 1-times the base width f of the triangle D.

The above remarks serve to describe the inventions, which are captured as a whole by the application and which further develop the prior art at least by means of the following feature combinations, in each case also independently, wherein two, several, or all of these feature combinations can also be combined, namely:

A device 1, which is characterized in that two insertion mechanisms 60 are provided, comprising preferably two retaining parts 62, which are separate from one another, which each have an insertion means 63, and by means of which the substance container 5 can be opened in intersecting or opposing insertion directions b, c.

A device 1, which is characterized in that the number of the emptied or not emptied substance containers 5 can be displayed via a counter 84.

A device 1, which is characterized in that an insertion means 63 has two insertion regions 104, which are separate from one another.

A device 1, which is characterized in that a free space 64, which extends in the transport direction r of the substance containers 5, is provided between the insertion regions 104.

A device 1, which is characterized in that two or more insertion tips 105 are formed at an insertion region 104 assigned to the substance container 5.

A device 1, which is characterized in that an insertion tip 105 is formed in a mandrel-like manner, comprising a tip region 107 adjacent to a cylindrical region 106.

A device 1, which is characterized in that the retaining part 62 is formed combined with a plastic spring 65.

A device 1, which is characterized in that the plastic spring 65 forms two spring arms 66, which are directed oppositely.

A device 1, which is characterized in that the spring arms 66 simultaneously serve to guide the retaining part 62 in response to an insertion process.

A device 1, which is characterized in that, starting at their free ends, the spring arms 66 have a guide recess 67, which interacts with a journal 68 attached to the housing.

A device 1, which is characterized in that in a side view, in which an insertion direction b, c presents itself in a line-shaped manner and both spring arms 66 are displayed in their longitudinal extension L, the spring arms 66 are formed concavely, with the retaining part 62 assigned to a longitudinal center of the combined spring arms 66.

A device 1, which is characterized in that two discharge channels 75 are provided and that the discharge channels 75 are merged upstream of the mouthpiece 6 in the flow direction s.

A device 1, which is characterized in that two suction channels 74 are provided.

A device 1, which is characterized in that in a flow direction s upstream of the substance container 5, one or both suction channels 74 are connected to the discharge channel 75 via a bypass 103.

A device 1, which is characterized in that a plurality of substance containers 5 can be accommodated simultaneously in the device 1.

A device 1, which is characterized in that the counter 84 has a drive pinion 87, which can be driven via a drive shaft 17 and which acts on a counting wheel 85 via a transfer gear 86.

A device 1, which is characterized in that alignment moldings 94, 97 for the transfer gear 86 and the counting wheel 85 are provided at the housing 52 and/or between the transfer gear 86 and the counting wheel 85, which provide for an assembly of the transfer gear 86 and of the counting wheel 85 in a specified angular alignment.

A device 1, which is characterized in that the device 1 has a pivotable closure cap 9 and that both insertion mechanisms 60 are acted on simultaneously with the pivoting of the closure cap 9.

A device 1, which is characterized in that the insertion mechanisms 60 are moved out of the substance container 5 again at the end of the pivoting movement of the closure cap 9.

All of the disclosed features (alone, but also in combination with one another) are essential for the invention. The disclosure content of the corresponding/enclosed priority documents (copy of the prior application) is hereby also included in its entirety into the disclosure of the application, also for the purpose of adding features of these documents into claims of the present application. With their features, the subclaims, also without the features of a referenced claim, characterize independent inventive further developments of the prior art, in particular to file divisional applications on the basis of these claims. The invention specified in each claim can additionally have one or several of the features specified in the above description, in particular provided with reference numerals and/or specifiedin the list of reference numerals. The invention also relates to designs, in the case of which individual features, which are mentioned in the above description, are not realized, in particular insofar as they are discernibly expendable for the respective intended purpose or can be replaced by other technically identical means.

LIST OF REFERENCE NUMERALS

| | |
|---|---|
| 1 | device |
| 2 | housing inner top part |
| 3 | housing inner bottom part |
| 4 | guide mechanism |
| 5 | substance container |
| 6 | mouthpiece |
| 7 | housing shell top part |
| 8 | housing shell bottom part |
| 9 | closure cap |
| 10 | closure cap top part |
| 11 | closure cap bottom part |
| 12 | cover section |
| 13 | cap section |
| 14 | cover part |
| 15 | base part |
| 16 | collar |
| 17 | drive shaft |
| 18 | bore |
| 19 | bore |
| 20 | actuating wheel |
| 21 | depression |
| 22 | entrainment protrusion |
| 23 | non-return device |
| 24 | locking lug |
| 25 | drive part |
| 26 | spring arm |
| 27 | entrainment lug |
| 28 | slotted guide |
| 29 | control surface |
| 30 | control journal |
| 31 | first contact surface |
| 32 | recess |
| 33 | second contact surface |
| 34 | control surface |
| 35 | third contact surface |
| 36 | storage chamber |
| 37 | side wall |

-continued

| | |
|---|---|
| 38 | guideway |
| 39 | web base |
| 40 | web ceiling |
| 41 | longitudinal groove |
| 42 | transverse groove |
| 43 | collection chamber |
| 44 | branch |
| 45 | floor space |
| 46 | sub-region |
| 47 | front wall |
| 48 | substance |
| 48' | substance |
| 49 | bottom |
| 50 | cover |
| 51 | rib |
| 52 | housing |
| 53 | insertion or housing opening, respectively |
| 54 | insertion rail |
| 55 | closure part |
| 56 | drive element |
| 57 | drive wheel |
| 58 | accommodating molding |
| 59 | groove |
| 60 | insertion mechanism |
| 61 | depression |
| 62 | retaining part |
| 63 | insertion means |
| 64 | slit-like free space |
| 65 | plastic spring |
| 66 | spring arm |
| 67 | guide recess |
| 68 | journal |
| 69 | guide appendage |
| 70 | guide notch |
| 71 | guide aperture |
| 72 | aperture |
| 73 | web |
| 74 | suction channel |
| 75 | discharge channel |
| 76 | punching section |
| 77 | cover web |
| 78 | opening |
| 79 | opening |
| 80 | cam |
| 81 | suction opening |
| 82 | mouthpiece channel |
| 83 | merging region |
| 84 | counter |
| 85 | counting wheel |
| 86 | transfer gear |
| 87 | drive pinion |
| 88 | collar |
| 89 | internal toothing |
| 90 | window |
| 91 | aperture |
| 92 | aperture |
| 92' | aperture |
| 93 | axle journal |
| 94 | alignment molding |
| 95 | aperture |
| 96 | radial collar |
| 97 | alignment molding |
| 98 | recess |
| 99 | hollow journal |
| 100 | axle body |
| 101 | stop rib extension |
| 102 | drive tooth |
| 103 | bypass |
| 104 | insertion region |
| 105 | insertion tip |
| 106 | cylindrical region |
| 107 | tip region |
| 108 | pedestal |
| 109 | longitudinal web |
| 110 | zenith region |
| 111 | bridge section |
| 112 | base line |
| 113 | leg |

-continued

| 114 | leg |
| --- | --- |
| 115 | side wall section |
| a | direction of rotation |
| b | insertion direction |
| c | insertion direction |
| d | outer diameter |
| e | height |
| f | base width |
| g | height |
| r | transport direction |
| s | air flow |
| x | pivot axis |
| y | cylinder axis |
| z | axis of symmetry |
| D | triangle |
| E | bearing plane |
| L | longitudinal |
| P | emptying position |

The invention claimed is:

1. A device for inhaling powder-type substances, comprising;
a mouthpiece,
two insertion mechanisms, each insertion mechanism comprising a separate retaining part having an insertion means for opening a sub-region in a substance container containing substance,
a discharge channel leading to the mouthpiece for discharging the substance, and
a pivotable closure cap,
wherein the insertion mechanisms are arranged such that the substance container can be opened in opposing insertion directions, and wherein both insertion mechanisms are acted on simultaneously with pivoting of the closure cap.

2. The device according to claim 1, further comprising a plurality of substance containers that can be moved successively into an emptying position, wherein the substance containers can be moved via a drive shaft of the device, which is accessible for a user from an outside, and wherein the drive shaft acts on a counting wheel of a counter for displaying a number of emptied or non-emptied substance containers or of performed inhalations.

3. The device according to claim 2, wherein the counter has a drive pinion that is configured to be driven via the drive shaft and which acts on the counting wheel via a transfer gear.

4. The device according to claim 3, wherein alignment moldings for the transfer gear and the counting wheel are provided at a housing of the device and/or between the transfer gear and the counting wheel, wherein the moldings provide for an assembly of the transfer gear and of the counting wheel in a specified angular alignment.

5. The device according to claim 3, wherein the device is configured such that the insertion mechanisms are moved out of the substance container again at an end of a pivoting movement of the closure cap.

6. The device according to claim 1, wherein each insertion means has two insertion regions, which are separate from one another.

7. The device according to claim 6, wherein a free space, which extends in a transport direction (r) of the substance container, is provided between the insertion regions of each insertion means.

8. The device according to claim 6, wherein two or more insertion tips are formed at each insertion region assigned to the substance container.

9. The device according to claim 8, wherein each insertion tip is formed in a mandrel-like manner, comprising a tip region adjacent to a cylindrical region.

10. The device according to claim 1, wherein each of the retaining parts is formed combined with a plastic spring.

11. The device according to claim 10, wherein the plastic spring forms two oppositely-directed spring arms.

12. The device according to claim 11, wherein the spring arms simultaneously guide the retaining parts in response to an insertion process.

13. The device according to claim 11, wherein the spring arms have free ends and wherein a guide recess is formed in the spring arms, starting at the free ends, which interacts with a journal attached to a housing of the device.

14. The device according to claim 11, wherein in a side view, in which an insertion direction presents itself in a line-shaped manner and both spring arms are displayed in a longitudinal extension (L), the spring arms are formed concavely, with the retaining part assigned to a longitudinal center of the combined spring arms.

15. The device according to claim 1, further comprising two suction channels comprising suction channels that are merged upstream of the mouthpiece in a flow direction.

16. The device according to claim 15, wherein in the flow direction upstream of the substance container, one of the suction channels is connected to one of the discharge channels via a bypass.

17. The device according to claim 16, wherein in the flow direction upstream of the substance container, one of the suction channels is connected to one of the discharger channels via a bypass.

18. The device according to claim 1, wherein the device is configured to accommodate a plurality of substance containers simultaneously.

19. A device for inhaling powder-type substances, comprising:
a mouthpiece,
two insertion mechanisms, each insertion mechanism comprising a separate retaining part having an insertion means for opening a sub-region in a substance container containing substance,
a discharge channel leading to the mouthpiece for discharging the substance, and
a pivotable closure cap,
wherein the insertion mechanisms are arranged such that the substance container can be opened in opposing insertion directions, and wherein both insertion mechanisms are acted on simultaneously with pivoting of the closure cap, and
wherein an action means stresses the insertion mechanisms in such a way that the retaining parts together with the insertion means can be displaced into an insertion position against the restoring force of spring arms.

20. A device for inhaling powder-type substances, comprising;
a mouthpiece,
two insertion mechanisms, each insertion mechanism comprising a separate retaining part having an insertion means for opening a sub-region in a substance container containing substance, and a discharge channel leading to the mouthpiece for discharging the substance,
a pivotable closure cap;
wherein the insertion mechanisms are arranged such that the substance container can be opened in intersecting or opposing insertion directions, and wherein both insertion mechanisms are acted on simultaneously with the pivoting of the closure cap, and wherein each insertion mechanism is moved out of the substance container again at the end of a pivoting movement of the closure cap from a device closed position into a device open position.

* * * * *